US012758584B2

(12) United States Patent
Puri et al.

(10) Patent No.: US 12,758,584 B2
(45) Date of Patent: Oct. 13, 2026

(54) IL-13Rα2 CHIMERIC ANTIGEN RECEPTORS AND METHODS OF USE

(71) Applicant: The United States of America, as represented by the Secretary, Dept. of Health and Human Services, Silver Spring, MD (US)

(72) Inventors: Raj K. Puri, Urbana, MD (US); Bharatkumar H. Joshi, Rockville, MD (US)

(73) Assignee: The United States of America, as represented by the Secretary, Department of Health and Human Services, Silver Spring, MD (US)

( * ) Notice: Subject to any disclaimer, the term of this patent is extended or adjusted under 35 U.S.C. 154(b) by 558 days.

(21) Appl. No.: 18/285,218

(22) PCT Filed: Apr. 1, 2022

(86) PCT No.: PCT/US2022/023112
§ 371 (c)(1),
(2) Date: Sep. 29, 2023

(87) PCT Pub. No.: WO2022/212879
PCT Pub. Date: Oct. 6, 2022

(65) Prior Publication Data

US 2024/0189351 A1 Jun. 13, 2024

Related U.S. Application Data

(60) Provisional application No. 63/169,575, filed on Apr. 1, 2021.

(51) Int. Cl.
*A61K 35/17* (2025.01)
*A61K 40/11* (2025.01)
(Continued)

(52) U.S. Cl.
CPC .............. *A61K 35/17* (2013.01); *A61K 40/11* (2025.01); *A61K 40/31* (2025.01);
(Continued)

(58) Field of Classification Search
CPC ........ A61K 35/17; A61K 40/11; A61K 40/31; A61K 40/4217; A61K 2239/13
See application file for complete search history.

(56) References Cited

U.S. PATENT DOCUMENTS

| | | | | |
|---|---|---|---|---|
| 2016/0000868 | A1 | 1/2016 | Vallera | |
| 2017/0088620 | A1* | 3/2017 | Nioi | C07K 16/2851 |
| 2019/0359723 | A1 | 11/2019 | Wang et al. | |

FOREIGN PATENT DOCUMENTS

| | | | | |
|---|---|---|---|---|
| WO | WO-2016/123142 A1 | | 8/2016 | |
| WO | WO-2019067805 A1 | * | 4/2019 | A61P 37/02 |

(Continued)

OTHER PUBLICATIONS

Balyasnikova et al., Characterization and Immunotherapeutic Implications for a Novel Antibody Targeting Interleukin (IL)-13 Receptor α2. *Journal of Biological Chemistry*, 287(36): 30215-30227, 2012.

(Continued)

*Primary Examiner* — Joanne Hama
*Assistant Examiner* — Dasia A Aldarondo
(74) *Attorney, Agent, or Firm* — Klarquist Sparkman, LLP

(57) ABSTRACT

Immunotherapies, particularly chimeric antigen receptors targeting IL-13Rα2 and their use for treating cancer are provided. A single chain fragment variable (scFv) that specifically binds IL-13Rα2, chimeric antigen receptors (CARs) including the IL-13Rα2 scFv, nucleic acids encoding the CARs, vectors including the nucleic acids encoding the CARs, and immune cells expressing the CARs are provided. Also provided are methods of treating a subject
(Continued)

with cancer, including administering to the subject an immune cell expressing an IL-13Rα2 scFv-CAR alone or in combination with other cancer therapies.

20 Claims, 22 Drawing Sheets

Specification includes a Sequence Listing.

(51) Int. Cl.

| | |
|---|---|
| ***A61K 40/31*** | (2025.01) |
| ***A61K 40/42*** | (2025.01) |
| ***A61K 45/06*** | (2006.01) |
| ***A61P 35/00*** | (2006.01) |
| ***C07K 16/28*** | (2006.01) |
| ***C12N 5/0783*** | (2010.01) |
| ***C12N 15/86*** | (2006.01) |

(52) U.S. Cl.

CPC .......... *A61K 40/4217* (2025.01); *A61K 45/06* (2013.01); *A61P 35/00* (2018.01); *C07K 16/2866* (2013.01); *C12N 5/0636* (2013.01); *C12N 15/86* (2013.01); *A61K 2239/13* (2023.05); *A61K 2239/17* (2023.05); *A61K 2239/21* (2023.05); *A61K 2239/22* (2023.05); *A61K 2239/47* (2023.05); *A61K 2239/54* (2023.05); *A61K 2239/58* (2023.05); *C12N 2740/15043* (2013.01)

(56) References Cited

FOREIGN PATENT DOCUMENTS

| | | | |
|---|---|---|---|
| WO | WO-2019/178078 | A1 | 9/2019 |
| WO | WO 2019/239213 | A2 | 12/2019 |
| WO | WO 2020/160639 | A1 | 8/2020 |
| WO | WO-2020/210665 | A1 | 10/2020 |
| WO | WO 2022/246052 | | 11/2022 |

OTHER PUBLICATIONS

Fujisawa et al., Histone modification enhances the effectiveness of IL-13 receptor targeted immunotoxin in murine models of human pancreatic cancer. *Journal of Translational Medicine*, 9:37, 2011 (13 pages).

International Search Report and Written Opinion for PCT/US2022/023112, dated Jun. 28, 2022 (12 pages).

Joshi et al., Human Adrenomedullin Up-regulates Interleukin-13 Receptor A2 Chain in Prostate Cancer In vitro and In vivo: A Novel Approach to Sensitize Prostate Cancer to Anticancer Therapy. *Cancer Res*, 68(22): 9311-9317, 2008.

Kioi et al., Targeting IL-13RA2-positive cancer with a novel recombinant immunotoxin composed of a single-chain antibody and mutated Pseudomonas exotoxin. *Mol Cancer Ther*, 7(6):1579-1587, 2008.

Krenciute et al., Characterization and Functional Analysis of scFv-based Chimeric Antigen Receptors to Redirect T Cells to IL 13Rα2-positive Glioma. *Molecular Therapy*, 24(2): 354-363, 2016.

Nakashima et al. A Novel Combination Immunotherapy for Cancer by IL-13Ra2—Targeted DNA Vaccine and Immunotoxin in Murine Tumor Models. *The Journal of Immunology*, 187(10): 4935-4946, 2011.

Song et al. Chimeric NKG2D CAR-expressing T cell-mediated attack of human ovarian cancer is enhanced by histone deacetylase inhibition. *Hum Gene Ther*, 24(3):295-305, 2013.

Brown et al., "Optimization of IL13Rα2-Targeted Chimeric Antigen Receptor T Cells for Improved Anti-tumor Efficacy against Glioblastoma," *Molecular Therapy* 26(1):31-44, 2018.

Sengupta et al., "Interleukin-13 Receptor Alpha 2-Targeted Glioblastoma Immunotherapy," *BioMed Research International* 2014:952128, 2014, 8 pages.

Fujisawa et al., "A Novel Role of Interleukin 13 Receptor alpha2 in Perineural Invasion and its Association with Poor Prognosis of Patients with Pancreatic Ductal Adenocarcinoma," *Cancers* (*Basel*), 12(5): 1294, published online May 20, 2020.

Ho et al., "*FasL* and *FADD* delivery by a glioma-specific and cell cycle-dependent HSV-1 amplicon virus enhanced apoptosis in primary human brain tumors," *Molecular Cancer*, 9(1):270, 15 pages. 2010.

* cited by examiner

FIG. 2

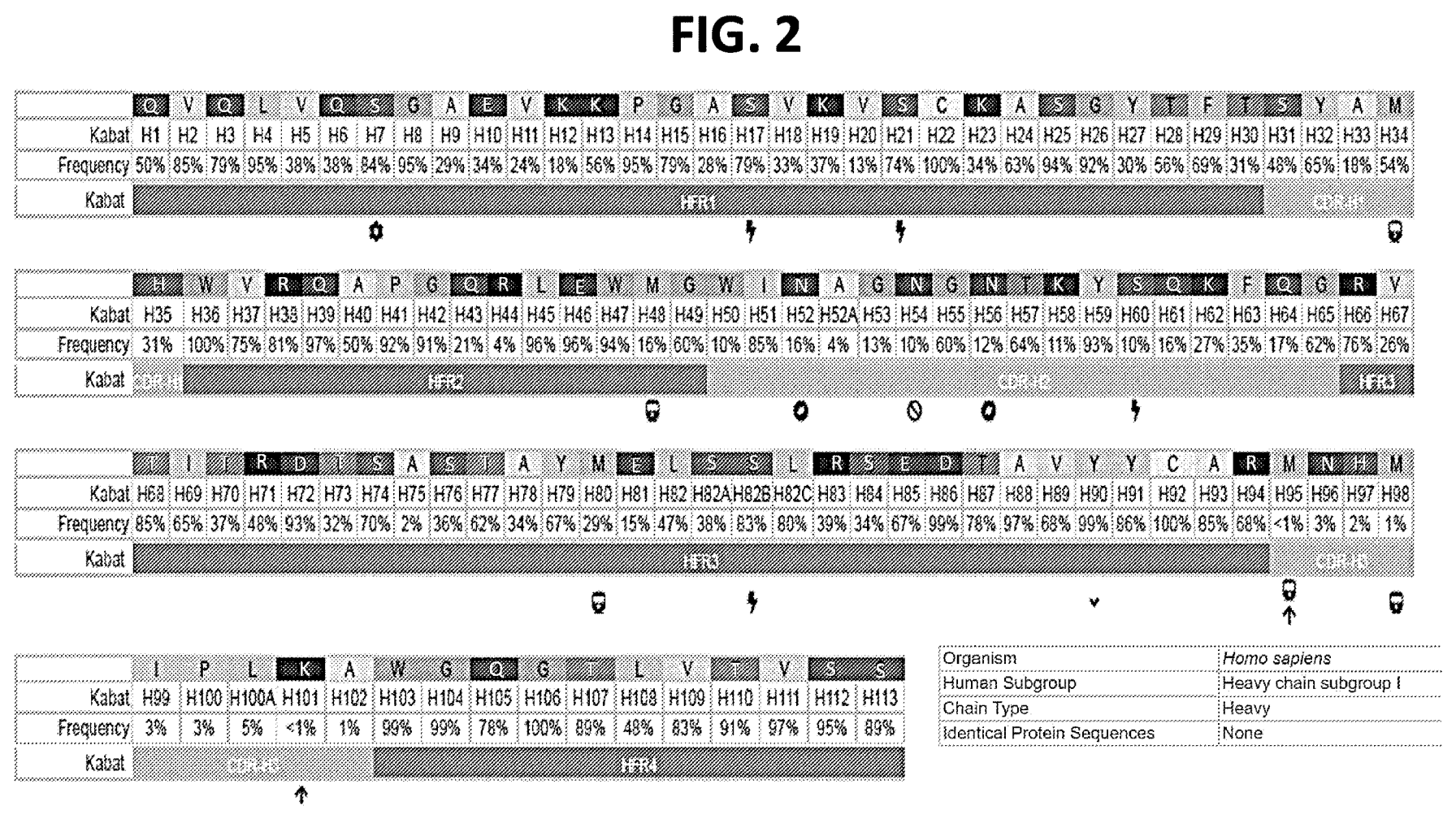

| | Q | V | Q | L | V | Q | S | G | A | E | V | K | K | P | G | A | S | V | K | V | S | C | K | A | S | G | Y | T | F | T | S | Y | A | M |
|---|---|---|---|---|---|---|---|---|---|---|---|---|---|---|---|---|---|---|---|---|---|---|---|---|---|---|---|---|---|---|---|---|---|---|
| Kabat | H1 | H2 | H3 | H4 | H5 | H6 | H7 | H8 | H9 | H10 | H11 | H12 | H13 | H14 | H15 | H16 | H17 | H18 | H19 | H20 | H21 | H22 | H23 | H24 | H25 | H26 | H27 | H28 | H29 | H30 | H31 | H32 | H33 | H34 |
| Frequency | 50% | 85% | 79% | 95% | 38% | 38% | 84% | 95% | 29% | 34% | 24% | 18% | 56% | 95% | 79% | 28% | 79% | 33% | 37% | 13% | 74% | 100% | 34% | 63% | 94% | 92% | 30% | 56% | 69% | 31% | 48% | 65% | 18% | 54% |
| Kabat | HFR1 | | | | | | | | | | | | | | | | | | | | | | | | | | | | | | CDR-H1 | | | |

| | H | W | V | R | Q | A | P | G | Q | R | L | E | W | M | G | W | I | N | A | G | N | G | N | T | K | Y | S | Q | K | F | Q | G | R | V |
|---|---|---|---|---|---|---|---|---|---|---|---|---|---|---|---|---|---|---|---|---|---|---|---|---|---|---|---|---|---|---|---|---|---|---|
| Kabat | H35 | H36 | H37 | H38 | H39 | H40 | H41 | H42 | H43 | H44 | H45 | H46 | H47 | H48 | H49 | H50 | H51 | H52 | H52A | H53 | H54 | H55 | H56 | H57 | H58 | H59 | H60 | H61 | H62 | H63 | H64 | H65 | H66 | H67 |
| Frequency | 31% | 100% | 75% | 81% | 97% | 50% | 92% | 91% | 21% | 4% | 96% | 96% | 94% | 16% | 60% | 10% | 85% | 16% | 4% | 13% | 10% | 60% | 12% | 64% | 11% | 93% | 10% | 16% | 27% | 35% | 17% | 62% | 76% | 26% |
| Kabat | CDR-H1 | HFR2 | | | | | | | | | | | | | | CDR-H2 | | | | | | | | | | | | | | | | | HFR3 | |

| | T | I | T | R | D | T | S | A | S | T | A | Y | M | E | L | S | S | L | R | S | E | D | T | A | V | Y | Y | C | A | R | M | N | H | M |
|---|---|---|---|---|---|---|---|---|---|---|---|---|---|---|---|---|---|---|---|---|---|---|---|---|---|---|---|---|---|---|---|---|---|---|
| Kabat | H68 | H69 | H70 | H71 | H72 | H73 | H74 | H75 | H76 | H77 | H78 | H79 | H80 | H81 | H82 | H82A | H82B | H82C | H83 | H84 | H85 | H86 | H87 | H88 | H89 | H90 | H91 | H92 | H93 | H94 | H95 | H96 | H97 | H98 |
| Frequency | 85% | 65% | 37% | 48% | 93% | 32% | 70% | 2% | 36% | 62% | 34% | 67% | 29% | 15% | 47% | 38% | 83% | 80% | 39% | 34% | 67% | 99% | 78% | 97% | 68% | 99% | 86% | 100% | 85% | 68% | <1% | 3% | 2% | 1% |
| Kabat | HFR3 | | | | | | | | | | | | | | | | | | | | | | | | | | | | | | CDR-H3 | | | |

| | I | P | L | K | A | W | G | Q | G | T | L | V | T | V | S | S |
|---|---|---|---|---|---|---|---|---|---|---|---|---|---|---|---|---|
| Kabat | H99 | H100 | H100A | H101 | H102 | H103 | H104 | H105 | H106 | H107 | H108 | H109 | H110 | H111 | H112 | H113 |
| Frequency | 3% | 3% | 5% | <1% | 1% | 99% | 99% | 78% | 100% | 89% | 48% | 83% | 91% | 97% | 95% | 89% |
| Kabat | CDR-H3 | | | | | HFR4 | | | | | | | | | | |

| | |
|---|---|
| Organism | *Homo sapiens* |
| Human Subgroup | Heavy chain subgroup I |
| Chain Type | Heavy |
| Identical Protein Sequences | None |

FIG. 3A

Regions Definition: Kabat

| SEQ ID NO (residues) | Region | Sequence Fragment | Residues | Length |
|---|---|---|---|---|
| SEQ ID NO: 3 (1-21) | Leader | MALPVTALLLPLALLLHAARP | 1 - 21 | 21 |
| SEQ ID NO: 3 (22-51) | HFR1 | QVQLVQSGAEVKKPGASVKVSCKASGYTFT | 22 - 51 | 30 |
| SEQ ID NO: 3 (52-56) | CDR-H1 | SYAMH | 52 - 56 | 5 |
| SEQ ID NO: 3 (57-70) | HFR2 | WVRQAPGQRLEWMG | 57 - 70 | 14 |
| SEQ ID NO: 3 (71-87) | CDR-H2 | WINAGNGNTKYSQKFQG | 71 - 87 | 17 |
| SEQ ID NO: 3 (88-119) | HFR3 | RVTITRDTSASTAYMELSSLRSEDTAVYYCAR | 88 - 119 | 32 |
| SEQ ID NO: 3 (120-128) | CDR-H3 | MNHMIPLKA | 120 - 128 | 9 |
| SEQ ID NO: 3 (129-139) | HFR4 | WGQGTLVTVSS | 129 - 139 | 11 |
| | | | | 139 |

FIG. 4

| | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|
| | A | I | Q | M | T | Q | S | P | S | S | L | S | A | S | V | G | D | R | V | T | I | T | C | R | A | S | Q | G | I | R | N | D | L | G |
| Kabat | L1 | L2 | L3 | L4 | L5 | L6 | L7 | L8 | L9 | L10 | L11 | L12 | L13 | L14 | L15 | L16 | L17 | L18 | L19 | L20 | L21 | L22 | L23 | L24 | L25 | L26 | L27 | L28 | L29 | L30 | L31 | L32 | L33 | L34 |
| Frequency | 5% | 45% | 15% | 34% | 90% | 93% | 48% | 80% | 58% | 59% | 50% | 80% | 39% | 68% | 21% | 98% | 24% | 43% | 63% | 71% | 71% | 41% | 99% | 40% | 43% | 79% | 47% | 16% | 23% | 4% | 36% | 5% | 50% | 5% |
| Kabat | LFR1 | | | | | | | | | | | | | | | | | | | | | | | [illegible] | | | | | | | | | | |

| | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|
| | W | Y | Q | Q | K | P | G | K | A | P | K | L | L | I | Y | A | A | S | S | L | Q | S | G | V | P | S | R | F | S | G | S | G | S | G |
| Kabat | L35 | L36 | L37 | L38 | L39 | L40 | L41 | L42 | L43 | L44 | L45 | L46 | L47 | L48 | L49 | L50 | L51 | L52 | L53 | L54 | L55 | L56 | L57 | L58 | L59 | L60 | L61 | L62 | L63 | L64 | L65 | L66 | L67 | L68 |
| Frequency | 100% | 86% | 89% | 90% | 67% | 89% | 92% | 23% | 57% | 95% | 57% | 75% | 76% | 89% | 85% | 11% | 40% | 87% | 15% | 32% | 11% | 75% | 95% | 64% | 93% | 26% | 99% | 99% | 89% | 97% | 96% | 58% | 94% | 93% |
| Kabat | LFR2 | | | | | | | | | | | | | | | [illegible] | | | | | | | LFR3 | | | | | | | | | | | |

| | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|
| | T | D | F | T | L | T | I | S | S | L | Q | P | E | D | F | A | T | Y | Y | C | L | Q | M | Y | N | Y | R | T | F | G | Q | G | T | K |
| Kabat | L69 | L70 | L71 | L72 | L73 | L74 | L75 | L76 | L77 | L78 | L79 | L80 | L81 | L82 | L83 | L84 | L85 | L86 | L87 | L88 | L89 | L90 | L91 | L92 | L93 | L94 | L96 | L97 | L98 | L99 | L100 | L101 | L102 | L103 |
| Frequency | 71% | 43% | 50% | 66% | 98% | 71% | 97% | 71% | 34% | 59% | 60% | 25% | 78% | 99% | 25% | 85% | 26% | 99% | 85% | 100% | 6% | 50% | <1% | 17% | 11% | 10% | 7% | 54% | 99% | 99% | 22% | 99% | 98% | 80% |
| Kabat | LFR3 | | | | | | | | | | | | | | | | | | | | [illegible] | | | | | | | | LFR4 | | | | | |

| | | | | | | | |
|---|---|---|---|---|---|---|---|
| | L | E | I | K | R | A | A |
| Kabat | L104 | L105 | L106 | L107 | L108 | L109 | L110 |
| Frequency | 61% | 51% | 48% | 69% | 60% | 25% | 10% |
| Kabat | LFR4 | | | | | | |

| | |
|---|---|
| Organism | *Homo sapiens* |
| Human Subgroup | Kappa Light chain subgroup I |
| Chain Type | Light |
| Identical Protein Sequences | None |

FIG. 5A

Regions Definition: Kabat

| SEQ ID NO (residues) | Region | Sequence Fragment | Residues | Length |
|---|---|---|---|---|
| SEQ ID NO: 3 (153-154) | Leader | AL | 1 - 2 | 2 |
| SEQ ID NO: 3 (155-177) | LFR1 | AIQMTQSPSSLSASVGDRVTITC | 3 - 25 | 23 |
| SEQ ID NO: 3 (178-188) | CDR-L1 | RASQGIRNDLG | 26 - 36 | 11 |
| SEQ ID NO: 3 (189-203) | LFR2 | WYQQKPGKAPKLLIY | 37 - 51 | 15 |
| SEQ ID NO: 3 (204-210) | CDR-L2 | AASSLQS | 52 - 58 | 7 |
| SEQ ID NO: 3 (211-242) | LFR3 | GVPSRFSGSGSGTDFTLTISSLQPEDFATYYC | 59 - 90 | 32 |
| SEQ ID NO: 3 (243-250) | CDR-L3 | LQMYNYRT | 91 - 98 | 8 |
| SEQ ID NO: 3 (251-263) | LFR4 | FGQGTKLEIKRAA | 99 - 111 | 13 |
| SEQ ID NO: 3 (264-538) | Tail | KPTTTPAPRPPTPAPTIASQPLSLRPEACRPAAGGAVHTRGLDFACDFWVLVVVGGVLAC<br>YSLLVTVAFIIFWVRSKRSRGGHSDYMNMTPRRPGPTRKHYQPYAPPRDFAAYRSVDKRG<br>RKKLLYIFKQPFMRPVQTTQEEDGCSCRFPEEEEGGCELGGRVKFSRSADAPAYQQGQN<br>QLYNELNLGRREEYDVLDKRRGRDPEMGGKPQRRKNPQEGLYNELQKDKMAEAYSEIGMK<br>GERRRGKGHDGLYQGLSTATKDTYDALHMQALPPR | 111 - 386 | 275 |
| | | | | 386 |

Distribution for Kabat position H1

| AA | Sequences | Frequency | AA | Sequences | Frequency |
|---|---|---|---|---|---|
| A | 655 | 1% | N | 46 | <1% |
| C | 877 | 2% | P | 121 | <1% |
| D | 1416 | 3% | Q | 26448 | 50% |
| E | 20608 | 39% | R | 365 | <1% |
| F | 4 | <1% | S | 359 | <1% |
| G | 977 | 2% | T | 146 | <1% |
| H | 99 | <1% | V | 149 | <1% |
| I | 45 | <1% | W | 4 | <1% |
| K | 136 | <1% | Y | 14 | <1% |
| L | 433 | <1% | - | 124 | <1% |
| M | 21 | <1% | Total | 53047 | 100% |

CSV

Distribution for Kabat position L1

| AA | Sequences | Frequency | AA | Sequences | Frequency |
|---|---|---|---|---|---|
| A | 1499 | 5% | N | 408 | 1% |
| C | 6 | <1% | P | 47 | <1% |
| D | 10141 | 36% | Q | 8768 | 31% |
| E | 4689 | 16% | R | 43 | <1% |
| F | 31 | <1% | S | 2032 | 7% |
| G | 203 | <1% | T | 50 | <1% |
| H | 136 | <1% | V | 41 | <1% |
| I | 39 | <1% | W | 4 | <1% |
| K | 72 | <1% | Y | 141 | <1% |
| L | 55 | <1% | - | 20 | <1% |
| M | 41 | <1% | Total | 28466 | 100% |

CSV

FIG. 8

Heavy chain

| IMGT | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|---|---|---|---|---|---|---|---|---|---|---|---|---|---|
| Kabat | 1 | 2 | 3 | 4 | 5 | 6 | 7 | 8 | 9 | - | 10 | 11 | 12 | 13 | 14 | 15 | 16 | 17 | 18 | 19 | 20 | 21 | 22 | 23 | 24 | 25 | 26 | 27 | 28 | 29 |
| Chotia | 1 | 2 | 3 | 4 | 5 | 6 | 7 | 8 | 9 | - | 10 | 11 | 12 | 13 | 14 | 15 | 16 | 17 | 18 | 19 | 20 | 21 | 22 | 23 | 24 | 25 | 26 | 27 | 28 | 29 |
| Martin | 1 | 2 | 3 | 4 | 5 | 6 | 7 | 8 | 9 | - | 10 | 11 | 12 | 13 | 14 | 15 | 16 | 17 | 18 | 19 | 20 | 21 | 22 | 23 | 24 | 25 | 26 | 27 | 28 | 29 |
| AA | Q | V | Q | L | V | Q | S | G | A | . | E | V | K | K | P | G | A | S | V | K | V | S | C | K | A | S | G | Y | T | F |

| IMGT | 31 | 32 | 33 | 34 | 35 | 36 | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 |
|---|---|---|---|---|---|---|---|---|---|---|---|---|---|---|---|---|---|---|---|---|---|---|---|---|---|---|---|---|---|---|
| Kabat | - | - | - | - | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 | 52A | 53 | - |
| Chotia | - | - | - | - | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 | 52A | 53 | - |
| Martin | - | - | - | - | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 | 52A | 53 | - |
| AA | . | . | . | . | T | S | Y | A | M | H | W | V | R | Q | A | P | G | Q | R | L | E | W | M | G | W | I | N | A | G | . |

| IMGT | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 | 89 | 90 |
|---|---|---|---|---|---|---|---|---|---|---|---|---|---|---|---|---|---|---|---|---|---|---|---|---|---|---|---|---|---|---|
| Kabat | - | 54 | 55 | 56 | 57 | 58 | 59 | 60 | 61 | 62 | 63 | 64 | - | 65 | 66 | 67 | 68 | 69 | 70 | 71 | 72 | 73 | 74 | 75 | 76 | 77 | 78 | 79 | 80 | 81 |
| Chotia | - | 54 | 55 | 56 | 57 | 58 | 59 | 60 | 61 | 62 | 63 | 64 | - | 65 | 66 | 67 | 68 | 69 | 70 | 71 | 72 | 73 | 74 | 75 | 76 | 77 | 78 | 79 | 80 | 81 |
| Martin | - | 54 | 55 | 56 | 57 | 58 | 59 | 60 | 61 | 62 | 63 | 64 | - | 65 | 66 | 67 | 68 | 69 | 70 | 71 | 72 | 72A | 72B | 72C | 73 | 74 | 75 | 76 | 77 | 78 |
| AA | . | N | G | N | T | K | Y | S | Q | K | F | Q | . | G | R | V | T | I | T | R | D | T | S | A | S | T | A | Y | M | E |

| IMGT | 91 | 92 | 93 | 94 | 95 | 96 | 97 | 98 | 99 | 100 | 101 | 102 | 103 | 104 | 105 | 106 | 107 | 108 | 109 | 110 | 111 | 112 | 113 | 114 | 115 | 116 | 117 | 118 | 119 | 120 |
|---|---|---|---|---|---|---|---|---|---|---|---|---|---|---|---|---|---|---|---|---|---|---|---|---|---|---|---|---|---|---|
| Kabat | 82 | 82A | 82B | 82C | 83 | 84 | 85 | 86 | 87 | 88 | 89 | 90 | 91 | 92 | 93 | 94 | 95 | 96 | 97 | 98 | - | - | 99 | 100 | 100A | 101 | 102 | 103 | 104 | 105 |
| Chotia | 82 | 82A | 82B | 82C | 83 | 84 | 85 | 86 | 87 | 88 | 89 | 90 | 91 | 92 | 93 | 94 | 95 | 96 | 97 | 98 | - | - | 99 | 100 | 100A | 101 | 102 | 103 | 104 | 105 |
| Martin | 79 | 80 | 81 | 82 | 83 | 84 | 85 | 86 | 87 | 88 | 89 | 90 | 91 | 92 | 93 | 94 | 95 | 96 | 97 | 98 | - | - | 99 | 100 | 100A | 101 | 102 | 103 | 104 | 105 |
| AA | L | S | S | L | R | S | E | D | T | A | V | Y | Y | C | A | R | M | N | H | M | . | . | I | P | L | K | A | W | G | Q |

| IMGT | 121 | 122 | 123 | 124 | 125 | 126 | 127 | 128 |
|---|---|---|---|---|---|---|---|---|
| Kabat | 106 | 107 | 108 | 109 | 110 | 111 | 112 | 113 |
| Chotia | 106 | 107 | 108 | 109 | 110 | 111 | 112 | 113 |
| Martin | 106 | 107 | 108 | 109 | 110 | 111 | 112 | 113 |
| AA | G | T | L | V | T | V | S | S |

= CDR1 (Heavy)
^ CDR2 (Heavy)
X CDR3 (Heavy)

FIG. 9

Light chain (Kappa chain)

| | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
| IMGT | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
| Kabat | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | - |
| Chotia | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | - |
| Martin | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | - |
| AA | A | I | Q | M | T | Q | S | P | S | S | L | S | A | S | V | G | D | R | V | T | I | T | C | R | A | S | Q | G | I | . |

| | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
| IMGT | 31 | 32 | 33 | 34 | 35 | 36 | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 |
| Kabat | - | - | - | - | - | 30 | 31 | 32 | 33 | 34 | 35 | 36 | 37 | 38 | 39 | 40 | 41 | 42 | 43 | 44 | 45 | 46 | 47 | 48 | 49 | 50 | 51 | - | - | - |
| Chotia | - | - | - | - | - | 30 | 31 | 32 | 33 | 34 | 35 | 36 | 37 | 38 | 39 | 40 | 41 | 42 | 43 | 44 | 45 | 46 | 47 | 48 | 49 | 50 | 51 | - | - | - |
| Martin | - | - | - | - | - | 30 | 31 | 32 | 33 | 34 | 35 | 36 | 37 | 38 | 39 | 40 | 41 | 42 | 43 | 44 | 45 | 46 | 47 | 48 | 49 | 50 | 51 | - | - | - |
| AA | . | . | . | . | . | R | N | D | L | G | W | Y | Q | Q | K | P | G | K | A | P | K | L | L | I | Y | A | A | . | . | . |

| | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
| IMGT | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 | 89 | 90 |
| Kabat | - | - | - | - | 52 | 53 | 54 | 55 | 56 | 57 | 58 | 59 | - | 60 | 61 | 62 | 63 | 64 | 65 | 66 | - | - | 67 | 68 | 69 | 70 | 71 | 72 | 73 | 74 |
| Chotia | - | - | - | - | 52 | 53 | 54 | 55 | 56 | 57 | 58 | 59 | - | 60 | 61 | 62 | 63 | 64 | 65 | 66 | - | - | 67 | 68 | 69 | 70 | 71 | 72 | 73 | 74 |
| Martin | - | - | - | - | 52 | 53 | 54 | 55 | 56 | 57 | 58 | 59 | - | 60 | 61 | 62 | 63 | 64 | 65 | 66 | - | - | 67 | 68 | 69 | 70 | 71 | 72 | 73 | 74 |
| AA | . | . | . | . | S | S | L | Q | S | G | V | P | . | S | R | F | S | G | S | G | . | . | S | G | T | D | F | T | L | T |

| | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
| IMGT | 91 | 92 | 93 | 94 | 95 | 96 | 97 | 98 | 99 | 100 | 101 | 102 | 103 | 104 | 105 | 106 | 107 | 108 | 109 | 110 | 111 | 112 | 113 | 114 | 115 | - | 116 | 117 | 118 | 119 |
| Kabat | 75 | 76 | 77 | 78 | 79 | 80 | 81 | 82 | 83 | 84 | 85 | 86 | 87 | 88 | 89 | 90 | 91 | 92 | - | - | - | - | - | 93 | 94 | 95 | 96 | 97 | 98 | 99 |
| Chotia | 75 | 76 | 77 | 78 | 79 | 80 | 81 | 82 | 83 | 84 | 85 | 86 | 87 | 88 | 89 | 90 | 91 | 92 | - | - | - | - | - | 93 | 94 | 95 | 96 | 97 | 98 | 99 |
| Martin | 75 | 76 | 77 | 78 | 79 | 80 | 81 | 82 | 83 | 84 | 85 | 86 | 87 | 88 | 89 | 90 | 91 | 92 | - | - | - | - | - | 93 | 94 | 95 | 96 | 97 | 98 | 99 |
| AA | I | S | S | L | Q | P | E | D | F | A | T | Y | Y | C | L | Q | M | Y | . | . | . | . | . | N | Y | | R | T | F | G |

| | | | | | | | | | |
|---|---|---|---|---|---|---|---|---|---|
| IMGT | 120 | 121 | 122 | 123 | 124 | 125 | 126 | 127 | 128 |
| Kabat | 100 | 101 | 102 | 103 | 104 | 105 | 106 | 107 | - |
| Chotia | 100 | 101 | 102 | 103 | 104 | 105 | 106 | 107 | - |
| Martin | 100 | 101 | 102 | 103 | 104 | 105 | 106 | 107 | - |
| AA | Q | G | T | K | L | E | I | K | . |

= CDR1 (Light)
^ CDR2 (Light)
X CDR3 (Light)

FIG. 10

CD8 Signal Peptide scFv IL-13Ra2 Transgene

```
        10        20        30        40        50        60        70        80        90       100
GSMALPVTALLLPLALLLHAARPQVQLVQSGAEVKKPGASVKVSCKASGYTFTSYAMHWVRQAPGQRLEWMGWINAGNGNTKYSQKFQGRVTITRDTSAS

       110       120       130       140       150       160       170       180       190       200
TAYMELSSLRSEDTAVYYCARMNHMIPLKAWGQGTLVTVSSGGGGSGGGGSGGSALAIQMTQSPSSLSASVGDRVTITCRASQGIRNDLGWYQQKPGKAP
```

CD8 Hinge

```
       210       220       230       240       250       260       270       280       290       300
KLLIYAASSLQSGVPSRFSGSGSGTDFTLTISSLQPEDFATYYCLQMYNYRTFGQGTKLEIKRAAKPTTTPAPRPPTPAPTIASQPLSLRPEACRPAAGG
```

CD28 TM

CD28Cyto 4-1BB Domain

```
       310       320       330       340       350       360       370       380       390       400
AVHTRGLDFACDFWVLVVVGGVLACYSLLVTVAFIIFWVRSKRSRGGHSDYMNMTPRRPGPTRKHYQPYAPPRDFAAYRSVDKRGRKKLLYIFKQPFMRP
```

CD3ζ Domain

```
       410       420       430       440       450       460       470       480       490       500
VQTTQEEDGCSCRFPEEEEGGCELGGGRVKFSRSADAPAYQQGQNQLYNELNLGRREEYDVLDKRRGRDPEMGGKPQRRKNPQEGLYNELQKDKMAEAYS

       510       520       530       540
EIGMKGERRRGKGHDGLYQGLSTATKDTYDALHMQALPPR*AA
```

GS= BamH1 site
VD = SalI restriction site
GGG = three glycine AAs linker

M = start codon
* = stop codon

SEQUENCE LISTING

```
<160> NUMBER OF SEQ ID NOS: 18

<210> SEQ ID NO 1
<211> LENGTH: 241
<212> TYPE: PRT
<213> ORGANISM: Artificial Sequence
<220> FEATURE:
<223> OTHER INFORMATION: An exemplary IL-13Ra2 scFv

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Met Asn His Met Ile Pro Leu Lys Ala Trp Gly Gln Gly Thr
            100                 105                 110

Leu Val Thr Val Ser Ser Gly Gly Gly Gly Ser Gly Gly Gly Gly Ser
        115                 120                 125

Gly Gly Ser Ala Leu Ala Ile Gln Met Thr Gln Ser Pro Ser Ser Leu
    130                 135                 140

Ser Ala Ser Val Gly Asp Arg Val Thr Ile Thr Cys Arg Ala Ser Gln
145                 150                 155                 160

Gly Ile Arg Asn Asp Leu Gly Trp Tyr Gln Gln Lys Pro Gly Lys Ala
                165                 170                 175

Pro Lys Leu Leu Ile Tyr Ala Ala Ser Ser Leu Gln Ser Gly Val Pro
            180                 185                 190

Ser Arg Phe Ser Gly Ser Gly Ser Gly Thr Asp Phe Thr Leu Thr Ile
        195                 200                 205

Ser Ser Leu Gln Pro Glu Asp Phe Ala Thr Tyr Tyr Cys Leu Gln Met
    210                 215                 220

Tyr Asn Tyr Arg Thr Phe Gly Gln Gly Thr Lys Leu Glu Ile Lys Arg
225                 230                 235                 240

Ala


<210> SEQ ID NO 2
<211> LENGTH: 722
<212> TYPE: DNA
<213> ORGANISM: Artificial Sequence
<220> FEATURE:
<223> OTHER INFORMATION: An exemplary nucleic acid sequence encoding an
      IL-13Ra2 scFv

<400> SEQUENCE: 2

aggtgcagct ggtgcagagc ggagcagagg tgaagaagcc aggagcctct gtgaaggtga      60

gctgcaaggc ctccggctac acattcacct cctatgccat gcactgggtg agacaggcac     120

ctggacagag gctggagtgg atgggctgga tcaacgccgg caacggcaat acaaagtact     180
```

-continued

```
ctcagaagtt tcagggccgc gtgacaatca cccgggacac atccgcctct accgcctata    240

tggagctgag ctccctgcgg tccgaggata ccgccgtgta ctattgcgcc agaatgaatc    300

acatgatccc actgaaggca tggggacagg gcacactggt gaccgtgtct agcggaggag    360

gaggcagcgg aggaggaggc tccggcggct ctgccctggc catccagatg acccagtccc    420

catcctctct gagcgcctcc gtgggcgacc gcgtgacaat cacctgtcgg gccagccagg    480

gcatcagaaa cgatctgggc tggtaccagc agaagcccgg caaggcccct aagctgctga    540

tctatgcagc aagctccctg cagtctggag tgcctagccg gttctctggc agcggctccg    600

gaacagactt tacactgacc atctctagcc tgcagccaga ggatttcgcc acctactatt    660

gcctgcagat gtacaattat agaacatttg gccagggcac caagctggag atcaagaggg    720

cc                                                                    722


<210> SEQ ID NO 3
<211> LENGTH: 538
<212> TYPE: PRT
<213> ORGANISM: Artificial Sequence
<220> FEATURE:
<223> OTHER INFORMATION: An exemplary IL-13Ra2-CAR

<400> SEQUENCE: 3

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Lys Pro Gly Ala Ser Val Lys Val Ser Cys Lys Ala Ser Gly Tyr
        35                  40                  45

Thr Phe Thr Ser Tyr Ala Met His Trp Val Arg Gln Ala Pro Gly Gln
    50                  55                  60

Arg Leu Glu Trp Met Gly Trp Ile Asn Ala Gly Asn Gly Asn Thr Lys
65                  70                  75                  80

Tyr Ser Gln Lys Phe Gln Gly Arg Val Thr Ile Thr Arg Asp Thr Ser
                85                  90                  95

Ala Ser Thr Ala Tyr Met Glu Leu Ser Ser Leu Arg Ser Glu Asp Thr
            100                 105                 110

Ala Val Tyr Tyr Cys Ala Arg Met Asn His Met Ile Pro Leu Lys Ala
        115                 120                 125

Trp Gly Gln Gly Thr Leu Val Thr Val Ser Ser Gly Gly Gly Gly Ser
    130                 135                 140

Gly Gly Gly Gly Ser Gly Gly Ser Ala Leu Ala Ile Gln Met Thr Gln
145                 150                 155                 160

Ser Pro Ser Ser Leu Ser Ala Ser Val Gly Asp Arg Val Thr Ile Thr
                165                 170                 175

Cys Arg Ala Ser Gln Gly Ile Arg Asn Asp Leu Gly Trp Tyr Gln Gln
            180                 185                 190

Lys Pro Gly Lys Ala Pro Lys Leu Leu Ile Tyr Ala Ala Ser Ser Leu
        195                 200                 205

Gln Ser Gly Val Pro Ser Arg Phe Ser Gly Ser Gly Ser Gly Thr Asp
    210                 215                 220

Phe Thr Leu Thr Ile Ser Ser Leu Gln Pro Glu Asp Phe Ala Thr Tyr
225                 230                 235                 240

Tyr Cys Leu Gln Met Tyr Asn Tyr Arg Thr Phe Gly Gln Gly Thr Lys
                245                 250                 255

Leu Glu Ile Lys Arg Ala Ala Lys Pro Thr Thr Thr Pro Ala Pro Arg
```

-continued

```
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
    290                 295                 300

Leu Asp Phe Ala Cys Asp Phe Trp Val Leu Val Val Val Gly Gly Val
305                 310                 315                 320

Leu Ala Cys Tyr Ser Leu Leu Val Thr Val Ala Phe Ile Ile Phe Trp
                325                 330                 335

Val Arg Ser Lys Arg Ser Arg Gly Gly His Ser Asp Tyr Met Asn Met
            340                 345                 350

Thr Pro Arg Arg Pro Gly Pro Thr Arg Lys His Tyr Gln Pro Tyr Ala
        355                 360                 365

Pro Pro Arg Asp Phe Ala Ala Tyr Arg Ser Val Asp Lys Arg Gly Arg
    370                 375                 380

Lys Lys Leu Leu Tyr Ile Phe Lys Gln Pro Phe Met Arg Pro Val Gln
385                 390                 395                 400

Thr Thr Gln Glu Glu Asp Gly Cys Ser Cys Arg Phe Pro Glu Glu Glu
                405                 410                 415

Glu Gly Gly Cys Glu Leu Gly Gly Gly Arg Val Lys Phe Ser Arg Ser
            420                 425                 430

Ala Asp Ala Pro Ala Tyr Gln Gln Gly Gln Asn Gln Leu Tyr Asn Glu
        435                 440                 445

Leu Asn Leu Gly Arg Arg Glu Glu Tyr Asp Val Leu Asp Lys Arg Arg
    450                 455                 460

Gly Arg Asp Pro Glu Met Gly Gly Lys Pro Gln Arg Arg Lys Asn Pro
465                 470                 475                 480

Gln Glu Gly Leu Tyr Asn Glu Leu Gln Lys Asp Lys Met Ala Glu Ala
                485                 490                 495

Tyr Ser Glu Ile Gly Met Lys Gly Glu Arg Arg Arg Gly Lys Gly His
            500                 505                 510

Asp Gly Leu Tyr Gln Gly Leu Ser Thr Ala Thr Lys Asp Thr Tyr Asp
        515                 520                 525

Ala Leu His Met Gln Ala Leu Pro Pro Arg
    530                 535
```

<210> SEQ ID NO 4
<211> LENGTH: 1625
<212> TYPE: DNA
<213> ORGANISM: Artificial Sequence
<220> FEATURE:
<223> OTHER INFORMATION: An exemplary nucleic acid sequence encoding an IL-13Ra2-CAR

<400> SEQUENCE: 4

```
atggcactgc ctgtgaccgc cctgctgctg ccactggccc tgctgctgca cgcagcccgg      60

ccacaggtgc agctggtgca gagcggagca gaggtgaaga agccaggagc ctctgtgaag     120

gtgagctgca aggcctccgg ctacacattc acctcctatg ccatgcactg ggtgagacag     180

gcacctggac agaggctgga gtggatgggc tggatcaacg ccggcaacgg caatacaaag     240

tactctcaga agtttcaggg ccgcgtgaca atcacccggg acacatccgc ctctaccgcc     300

tatatggagc tgagctccct gcggtccgag gataccgccg tgtactattg cgccagaatg     360

aatcacatga tcccactgaa ggcatgggga cagggcacac tggtgaccgt gtctagcgga     420

ggaggaggca gcggaggagg aggctccggc ggctctgccc tggccatcca gatgacccag     480
```

tccccatcct ctctgagcgc ctccgtgggc gaccgcgtga caatcacctg tcgggccagc 540
cagggcatca gaaacgatct gggctggtac cagcagaagc ccggcaaggc ccctaagctg 600
ctgatctatg cagcaagctc cctgcagtct ggagtgccta gccggttctc tggcagcggc 660
tccggaacag actttacact gaccatctct agcctgcagc cagaggattt cgccacctac 720
tattgcctgc agatgtacaa ttatagaaca tttggccagg gcaccaagct ggagatcaag 780
agggccgcca agccaaccac aaccccagca cctcgccccc ctacaccagc accaaccatc 840
gcatcccagc ctctgtctct gagaccagag gcatgtaggc cagcagcagg aggagcagtg 900
cacacaaggg gcctggactt cgcctgcgat ttttgggtgc tggtggtggt gggaggcgtg 960
ctggcctgtt actctctgct ggtgaccgtg gccttcatca tcttttgggt gaggagcaag 1020
cggagcaggg gaggacacag cgactacatg aacatgacac cacggagacc tggaccaacc 1080
aggaagcact accagcctta tgcaccacca agggacttcg cagcataccg cagcgtggat 1140
aagagaggca ggaagaagct gctgtatatc ttcaagcagc ccttcatgcg gcccgtgcag 1200
acaacccagg aggaggacgg ctgctcctgt agattccccg aggaggagga gggaggatgt 1260
gagctgggag gcggcagagt gaagttttct cggagcgccg atgcacctgc ataccagcag 1320
ggacagaatc agctgtataa cgagctgaat ctgggcaggc gcgaggagta cgacgtgctg 1380
gataagaggc ggggccggga ccccgagatg ggaggcaagc cacagaggcg caagaacccc 1440
caggagggcc tgtacaatga gctgcagaag gacaagatgg ccgaggccta ttccgagatc 1500
ggcatgaagg gagagcggag aaggggcaag ggacacgatg gcctgtacca gggcctgtct 1560
acagccacca aggacaccta tgatgccctg cacatgcagg ccctgcctcc acgctaagcg 1620
gccgc 1625

<210> SEQ ID NO 5
<211> LENGTH: 21
<212> TYPE: PRT
<213> ORGANISM: Artificial Sequence
<220> FEATURE:
<223> OTHER INFORMATION: An exemplary CD8a signal peptide

<400> SEQUENCE: 5

Met Ala Leu Pro Val Thr Ala Leu Leu Leu Pro Leu Ala Leu Leu Leu
1 5 10 15

His Ala Ala Arg Pro
20

<210> SEQ ID NO 6
<211> LENGTH: 47
<212> TYPE: PRT
<213> ORGANISM: Artificial Sequence
<220> FEATURE:
<223> OTHER INFORMATION: An exemplary CD8a hinge domain

<400> SEQUENCE: 6

Ala Lys Pro Thr Thr Thr Pro Ala Pro Arg Pro Pro Thr Pro Ala Pro
1 5 10 15

Thr Ile Ala Ser Gln Pro Leu Ser Leu Arg Pro Glu Ala Cys Arg Pro
20 25 30

Ala Ala Gly Gly Ala Val His Thr Arg Gly Leu Asp Phe Ala Cys
35 40 45

<210> SEQ ID NO 7
<211> LENGTH: 29

<212> TYPE: PRT
<213> ORGANISM: Artificial Sequence
<220> FEATURE:
<223> OTHER INFORMATION: An exemplary CD28 transmembrane domain

<400> SEQUENCE: 7

```
Asp Phe Trp Val Leu Val Val Val Gly Gly Val Leu Ala Cys Tyr Ser
1               5                   10                  15

Leu Leu Val Thr Val Ala Phe Ile Ile Phe Trp Val Arg
            20                  25
```

<210> SEQ ID NO 8
<211> LENGTH: 42
<212> TYPE: PRT
<213> ORGANISM: Artificial Sequence
<220> FEATURE:
<223> OTHER INFORMATION: An exemplary CD28 cytoplasmic signaling domain

<400> SEQUENCE: 8

```
Ser Lys Arg Ser Arg Gly Gly His Ser Asp Tyr Met Asn Met Thr Pro
1               5                   10                  15

Arg Arg Pro Gly Pro Thr Arg Lys His Tyr Gln Pro Tyr Ala Pro Pro
            20                  25                  30

Arg Asp Phe Ala Ala Tyr Arg Ser Val Asp
        35                  40
```

<210> SEQ ID NO 9
<211> LENGTH: 42
<212> TYPE: PRT
<213> ORGANISM: Artificial Sequence
<220> FEATURE:
<223> OTHER INFORMATION: An exemplary 4-1BB cytoplasmic signaling domain

<400> SEQUENCE: 9

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 10
<211> LENGTH: 113
<212> TYPE: PRT
<213> ORGANISM: Artificial Sequence
<220> FEATURE:
<223> OTHER INFORMATION: An exemplary CD3z cytoplasmic signaling domain

<400> SEQUENCE: 10

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95
```

```
Ala Thr Lys Asp Thr Tyr Asp Ala Leu His Met Gln Ala Leu Pro Pro
            100                 105                 110

Arg


<210> SEQ ID NO 11
<211> LENGTH: 64
<212> TYPE: DNA
<213> ORGANISM: Artificial Sequence
<220> FEATURE:
<223> OTHER INFORMATION: An exemplary nucleic acid sequence encoding a
      CD8a signal peptide

<400> SEQUENCE: 11

atggcactgc ctgtgaccgc cctgctgctg ccactggccc tgctgctgca cgcagcccgg     60

ccac                                                                  64


<210> SEQ ID NO 12
<211> LENGTH: 141
<212> TYPE: DNA
<213> ORGANISM: Artificial Sequence
<220> FEATURE:
<223> OTHER INFORMATION: An exemplary nucleic acid sequence encoding a
      CD8a hinge domain

<400> SEQUENCE: 12

gccaagccaa ccacaacccc agcacctcgc ccccctacac cagcaccaac catcgcatcc     60

cagcctctgt ctctgagacc agaggcatgt aggccagcag caggaggagc agtgcacaca    120

aggggcctgg acttcgcctg c                                              141


<210> SEQ ID NO 13
<211> LENGTH: 87
<212> TYPE: DNA
<213> ORGANISM: Artificial Sequence
<220> FEATURE:
<223> OTHER INFORMATION: An exemplary nucleic acid sequence encoding a
      CD28 transmembrane domain

<400> SEQUENCE: 13

gatttttggg tgctggtggt ggtgggaggc gtgctggcct gttactctct gctggtgacc     60

gtggccttca tcatcttttg ggtgagg                                         87


<210> SEQ ID NO 14
<211> LENGTH: 120
<212> TYPE: DNA
<213> ORGANISM: Artificial Sequence
<220> FEATURE:
<223> OTHER INFORMATION: An exemplary nucleic acid sequence encoding a
      CD28 cytoplasmic signaling domain

<400> SEQUENCE: 14

agcaagcgga gcaggggagg acacagcgac tacatgaaca tgacaccacg gagacctgga     60

ccaaccagga agcactacca gccttatgca ccaccaaggg acttcgcagc ataccgcagc    120


<210> SEQ ID NO 15
<211> LENGTH: 126
<212> TYPE: DNA
<213> ORGANISM: Artificial Sequence
<220> FEATURE:
<223> OTHER INFORMATION: An exemplary nucleic acid sequence encoding a
      4-1BB cytoplasmic signaling domain

<400> SEQUENCE: 15

aagagaggca ggaagaagct gctgtatatc ttcaagcagc ccttcatgcg gcccgtgcag     60
```

acaacccagg aggaggacgg ctgctcctgt agattccccg aggaggagga gggaggatgt 120
gagctg 126

<210> SEQ ID NO 16
<211> LENGTH: 339
<212> TYPE: DNA
<213> ORGANISM: Artificial Sequence
<220> FEATURE:
<223> OTHER INFORMATION: An exemplary nucleic acid sequence encoding a CD3z cytoplasmic signaling domain

<400> SEQUENCE: 16
agagtgaagt tttctcggag cgccgatgca cctgcatacc agcagggaca gaatcagctg 60
tataacgagc tgaatctggg caggcgcgag gagtacgacg tgctggataa gaggcggggc 120
cgggaccccg agatgggagg caagccacag aggcgcaaga acccccagga gggcctgtac 180
aatgagctgc agaaggacaa gatggccgag gcctattccg agatcggcat gaagggagag 240
cggagaaggg gcaagggaca cgatggcctg taccagggcc tgtctacagc caccaaggac 300
acctatgatg ccctgcacat gcaggccctg cctccacgc 339

<210> SEQ ID NO 17
<211> LENGTH: 21
<212> TYPE: DNA
<213> ORGANISM: Artificial Sequence
<220> FEATURE:
<223> OTHER INFORMATION: An exemplary nucleic acid sequence encoding an siRNA

<400> SEQUENCE: 17
gctaccattt ggtttcatct t 21

<210> SEQ ID NO 18
<211> LENGTH: 538
<212> TYPE: PRT
<213> ORGANISM: Artificial Sequence
<220> FEATURE:
<223> OTHER INFORMATION: An exemplary scFv IL-13Ra2 CAR

<400> SEQUENCE: 18

Met Ala Leu Pro Val Thr Ala Leu Leu Leu Pro Leu Ala Leu Leu Leu
1 5 10 15

His Ala Ala Arg Pro Gln Val Gln Leu Val Gln Ser Gly Ala Glu Val
20 25 30

Lys Lys Pro Gly Ala Ser Val Lys Val Ser Cys Lys Ala Ser Gly Tyr
35 40 45

Thr Phe Thr Ser Tyr Ala Met His Trp Val Arg Gln Ala Pro Gly Gln
50 55 60

Arg Leu Glu Trp Met Gly Trp Ile Asn Ala Gly Asn Gly Asn Thr Lys
65 70 75 80

Tyr Ser Gln Lys Phe Gln Gly Arg Val Thr Ile Thr Arg Asp Thr Ser
85 90 95

Ala Ser Thr Ala Tyr Met Glu Leu Ser Ser Leu Arg Ser Glu Asp Thr
100 105 110

Ala Val Tyr Tyr Cys Ala Arg Met Asn His Met Ile Pro Leu Lys Ala
115 120 125

Trp Gly Gln Gly Thr Leu Val Thr Val Ser Ser Gly Gly Gly Gly Ser
130 135 140

Gly Gly Gly Gly Ser Gly Gly Ser Ala Leu Ala Ile Gln Met Thr Gln

-continued

```
145                 150                 155                 160

Ser Pro Ser Ser Leu Ser Ala Ser Val Gly Asp Arg Val Thr Ile Thr
                165                 170                 175

Cys Arg Ala Ser Gln Gly Ile Arg Asn Asp Leu Gly Trp Tyr Gln Gln
            180                 185                 190

Lys Pro Gly Lys Ala Pro Lys Leu Leu Ile Tyr Ala Ala Ser Ser Leu
        195                 200                 205

Gln Ser Gly Val Pro Ser Arg Phe Ser Gly Ser Gly Ser Gly Thr Asp
    210                 215                 220

Phe Thr Leu Thr Ile Ser Ser Leu Gln Pro Glu Asp Phe Ala Thr Tyr
225                 230                 235                 240

Tyr Cys Leu Gln Met Tyr Asn Tyr Arg Thr Phe Gly Gln Gly Thr Lys
                245                 250                 255

Leu Glu Ile Lys Arg Ala Ala Lys Pro Thr Thr Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
    290                 295                 300

Leu Asp Phe Ala Cys Asp Phe Trp Val Leu Val Val Val Gly Gly Val
305                 310                 315                 320

Leu Ala Cys Tyr Ser Leu Leu Val Thr Val Ala Phe Ile Ile Phe Trp
                325                 330                 335

Val Arg Ser Lys Arg Ser Arg Gly Gly His Ser Asp Tyr Met Asn Met
            340                 345                 350

Thr Pro Arg Arg Pro Gly Pro Thr Arg Lys His Tyr Gln Pro Tyr Ala
        355                 360                 365

Pro Pro Arg Asp Phe Ala Ala Tyr Arg Ser Val Asp Lys Arg Gly Arg
    370                 375                 380

Lys Lys Leu Leu Tyr Ile Phe Lys Gln Pro Phe Met Arg Pro Val Gln
385                 390                 395                 400

Thr Thr Gln Glu Glu Asp Gly Cys Ser Cys Arg Phe Pro Glu Glu Glu
                405                 410                 415

Glu Gly Gly Cys Glu Leu Gly Gly Gly Arg Val Lys Phe Ser Arg Ser
            420                 425                 430

Ala Asp Ala Pro Ala Tyr Gln Gln Gly Gln Asn Gln Leu Tyr Asn Glu
        435                 440                 445

Leu Asn Leu Gly Arg Arg Glu Glu Tyr Asp Val Leu Asp Lys Arg Arg
    450                 455                 460

Gly Arg Asp Pro Glu Met Gly Gly Lys Pro Gln Arg Arg Lys Asn Pro
465                 470                 475                 480

Gln Glu Gly Leu Tyr Asn Glu Leu Gln Lys Asp Lys Met Ala Glu Ala
                485                 490                 495

Tyr Ser Glu Ile Gly Met Lys Gly Glu Arg Arg Arg Gly Lys Gly His
            500                 505                 510

Asp Gly Leu Tyr Gln Gly Leu Ser Thr Ala Thr Lys Asp Thr Tyr Asp
        515                 520                 525

Ala Leu His Met Gln Ala Leu Pro Pro Arg
    530                 535
```

IL-13Rα2 CHIMERIC ANTIGEN RECEPTORS AND METHODS OF USE

CROSS REFERENCE TO RELATED APPLICATIONS

This is the U.S. National Stage of International Application No. PCT/US2022/023112, filed Apr. 1, 2022, which was published in English under PCT Article 21 (2), which in turn claims the benefit of U.S. Provisional Application No. 63/169,575, filed Apr. 1, 2021, both of which are incorporated by reference herein.

FIELD OF THE DISCLOSURE

This disclosure relates to immunotherapies, particularly chimeric antigen receptors targeting IL-13Rα2 and their use for treating cancer.

INCORPORATION OF ELECTRONIC SEQUENCE LISTING

The Sequence Listing is submitted as an ASCII text file named "Sequence.txt," created on Sep. 28, 2023, 24,576 bytes, which is incorporated by reference herein.

BACKGROUND

IL-13Rα2 is a high affinity receptor for cytokine interleukin-13 (IL-13) and a known tumor antigen. While the significance of IL-13Rα2 expression in cancer is not fully understood, it has been shown that IL-13Rα2 is overexpressed in a variety of human cancers, including malignant gliomas, head and neck cancer, Kaposi's sarcoma, renal cell carcinoma, ovarian carcinoma, breast cancer, and pancreatic cancer, making IL-13Rα2 a potential target for cancer immunotherapy.

Chimeric antigen receptor (CAR)-T cell therapy has become a promising immunotherapeutic strategy for the treatment of various blood cancers. While CAR-T cells are effective in hematological malignancies, such as leukemia and lymphoma, to date very limited activity has been seen in human solid cancers. Improving targeting of CAR-T cells in solid tumors, either alone or in combination with other agents targeting tumor stroma (the tumor microenvironment, including myeloid derived suppressor cells, tumor associated macrophages and fibroblasts), would signify a major advance in the field of CAR-T immunotherapy.

SUMMARY OF THE DISCLOSURE

IL-13Rα2 is significantly upregulated in several cancers, thus it is a target for immunotherapy for the treatment of a variety of cancers. Chimeric antigen receptors (CARs) specifically targeting cells expressing IL-13Rα2 are provided herein. These CARs can be used in immunotherapy to target cancers expressing or overexpressing IL-13Rα2.

Disclosed herein are single chain fragment variables (scFvs) that specifically bind IL-13Rα2. In some embodiments, the scFv has an amino acid sequence that includes the variable heavy chain (VH) domain complementarity determining region 1 (CDR1), CDR2 and CDR3 amino acid sequences of SEQ ID NO: 1 and the variable light chain (VL) domain CDR1, CDR2 and CDR3 amino acid sequences of SEQ ID NO: 1. In some examples, the scFv has at least 90% identity to the amino acid sequence of SEQ ID NO: 1, or includes or consists of the amino acid sequence of SEQ ID NO: 1. In some examples, the scFv specifically binds to cells expressing IL-13Rα2.

Also provided are nucleic acids encoding the IL-13Rα2 scFv and vectors comprising the nucleic acids (such as a viral vector). In some embodiments, the nucleic acid encoding the IL-13Rα2 scFv is codon-optimized. In some examples, the IL-13Rα2 scFv is encoded by a nucleic acid sequence with at least 90% identity to the nucleic acid sequence of SEQ ID NO: 2. In other examples, the IL-13Rα2 scFv is encoded by a nucleic acid that includes or consists of the nucleic acid sequence of SEQ ID NO: 2.

Also provided are CARs that include the IL-13Rα2 scFv, a hinge domain, a transmembrane domain, and an intracellular domain with one or more signaling domains. In some embodiments, the CAR further comprises a signal peptide. In some examples, the signal peptide is a CD8α signal peptide. In some examples, the transmembrane domain is a CD28 transmembrane domain. In some examples, the intracellular domain includes one or more of CD28, 4-1BB, and CD3ζ signaling domains, or any combination of two or more thereof. In a non-limiting embodiment, the IL-13Rα2-CAR includes the IL-13Rα2 scFv, a CD8α hinge domain, a CD28 transmembrane domain, and an intracellular domain including a CD28 domain, a 4-1BB domain, and a CD3ζ domain. In some examples, the IL-13Rα2-CAR includes an amino acid sequence with at least 90% identity to the amino acid sequence of SEQ ID NO: 3, or includes or consists of the amino acid sequence of SEQ ID NO: 3.

Nucleic acids encoding the IL-13Rα2-CARs disclosed herein, and vectors including the nucleic acids (such as a viral vector) are also provided. In some embodiments, the nucleic acid encoding the IL-13Rα2-CAR is codon-optimized for expression in a particular cell type (e.g., bacteria, yeast, insect, mouse, human). In some examples, the IL-13Rα2-CAR is encoded by a nucleic acid sequence with at least 90% identity to the nucleic acid sequence of SEQ ID NO: 4. In other examples, the IL-13Rα2-CAR is encoded by a nucleic acid that includes or consists of the nucleic acid sequence of SEQ ID NO: 4. Vectors including a nucleic acid molecule encoding an IL-13Rα2-CAR are also disclosed herein. In some examples, the vector is a viral vector, such as a lentiviral vector.

Immune cells expressing the disclosed IL-13Rα2-CARs, such as immune cells including a nucleic acid encoding a disclosed IL-13Rα2-CAR, or a vector encoding a disclosed IL-13Rα2-CAR, are also provided. In some examples, the cells are T cells, natural killer (NK) cells, natural killer T (NKT) cells, or macrophages. In specific, non-limiting examples, the immune cells are T cells. In some examples, the immune cells are obtained from peripheral blood. Methods of producing cells expressing the IL-13Rα2-CARs are provided. These methods include transducing or transfecting cells, such as T cells, NK cells, NKT cells, or macrophages, with a vector encoding a disclosed IL-13Rα2-CAR.

Also provided are methods for treating a subject with cancer, for example by administering a cell (such as a T cell, NK cell, NKT cell, or macrophage) expressing an IL-13Rα2-CAR, or including a vector encoding an IL-13Rα2-CAR. In some examples, the subject has a cancer that expresses or over-expresses IL-13Rα2. In particular non-limiting examples, the subject has pancreatic cancer, glioblastoma, head and neck squamous cell carcinoma, ovarian cancer, uterine cancer, prostate cancer, breast cancer, melanoma, non-small cell lung cancer (NSCLC), renal cell carcinoma, Kaposi sarcoma, or adrenal carcinoma. In some examples, the method further includes treating the subject with one or more of surgery, radiation, chemotherapy, or an additional immunotherapy. In further examples, a histone deacetylase (HDAC) inhibitor, a cell cycle and/or checkpoint inhibitor, adrenomedullin, an IL-13-PE immunotoxin, or any combination of two or more thereof, is administered to the subject in combination with IL-13Rα2-CAR immune cells.

The foregoing and other features of the disclosure will become more apparent from the following detailed description, which proceeds with reference to the accompanying figures.

BRIEF DESCRIPTION OF THE DRAWINGS

FIG. 2 shows amino acid numbering of heavy chain residues of the IL-13Rα2 antibody using the Kabat numbering scheme. The sequence shown is residues 22-139 of SEQ ID NO: 3.

FIGS. 3A-3B show analyses of the heavy chain of the IL-13Rα2 antibody. FIG. 3A is a table providing the region, sequence, residue number and length of heavy chain amino acids of scFv-IL-13Rα2. FIG. 3B is a loop structure of heavy chain CDRs with amino acid residue position number. The sequence shown is residues 22-139 of SEQ ID NO: 3.

FIG. 4 shows amino acid numbering of light chain residues of the IL-13Rα2 antibody using the Kabat numbering scheme. The sequence shown is residues 155-263 of SEQ ID NO: 3.

FIGS. 5A-5B show analyses of the light chain of the IL-13Rα2 antibody. FIG. 5A is a table providing the region, sequence, residue number and length of light chain amino acids of scFv-IL-13Rα2. FIG. 5B is a loop structure of light chain CDRs with amino acid residue position number. The sequence shown is residues 155-260 of SEQ ID NO: 3.

FIG. 8 is a comparative sequence alignment of the heavy chain residues of the IL-13Rα2 antibody according to IMGT, Kabat, Chothia and Martin numbering schemes (SEQ ID NO: 3, residues 22-139).

FIG. 9 is a comparative sequence alignment of the light chain residues of the IL-13Rα2 antibody according to IMGT, Kabat, Chothia and Martin numbering schemes (SEQ ID NO: 3, residues 155-260).

FIG. 10 shows the amino acid sequence of an exemplary scFv IL-13Rα2 CAR and location of each element (SEQ ID NO: 18).

FIG. 13B shows a representative IFA image of transduced Jurkat cells.

SEQUENCE LISTING

Figure 1:
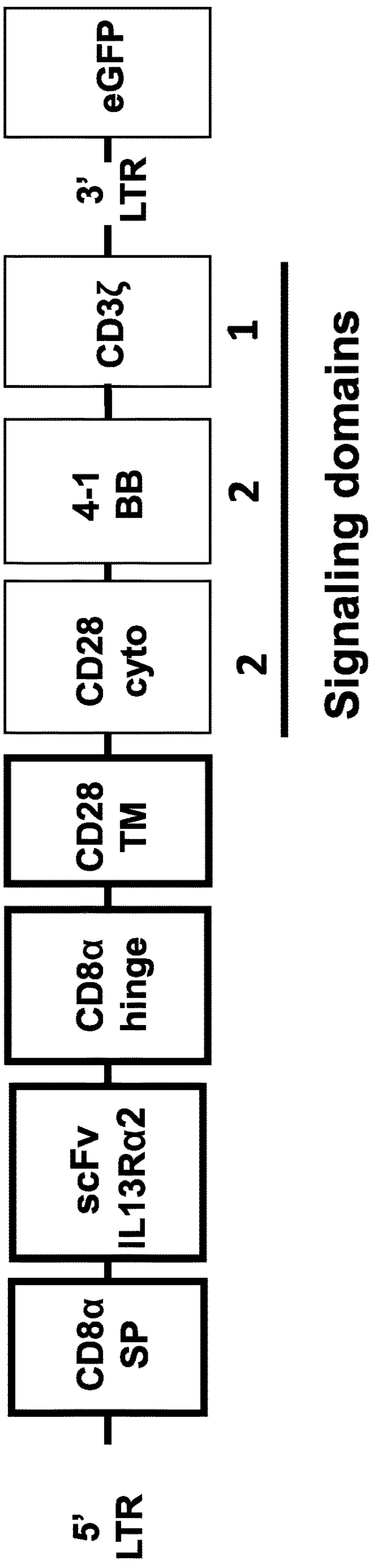
FIG. 1 shows a schematic diagram of an exemplary scFv-IL-13Rα2 CAR construct. The construct contains a 5'-CD8α signal peptide, scFv IL-13Rα2, CD8α hinge domain, CD28 transmembrane domain, and endodomains from CD28 cytoplasmic domain, 4-1BB and CD3ζ.

Any nucleic acid and amino acid sequences listed herein or in the accompanying Sequence Listing are shown using standard letter abbreviations for nucleotide bases and amino acids, as defined in 37 C.F.R. § 1.822. In at least some cases, only one strand of each nucleic acid sequence is shown, but the complementary strand is understood as included by any reference to the displayed strand. In the accompanying sequence listing:

SEQ ID NO: 1 is the amino acid sequence of an exemplary IL-13Rα2 scFv.
QVQLVQSGAEVKKPGASVKVSCKASGYTFTSYAMHWVRQAPGQRLEWMGWINAGNGN
TKYSQKFQGRVTITRDTSASTAYMELSSLRSEDTAVYYCARMNHMIPLKAWGQGTLVTVS
SGGGGSGGGGSGGSALAIQMTQSPSSLSASVGDRVTITCRASQGIRNDLGWYQQKPGKAP
KLLIYAASSLQSGVPSRFSGSGSGTDFTLTISSLQPEDFATYYCLQMYNYRTFGQGTKLEIK
RA SEQ ID NO: 2 is an exemplary nucleic acid sequence encoding the IL-13Rα2 scFv of SEQ ID NO: 1.
AGGTGCAGCTGGTGCAGAGCGGAGCAGAGGTGAAGAAGCCAGGAGCCTCTGTGAAGG
TGAGCTGCAAGGCCTCCGGCTACACATTCACCTCCTATGCCATGCACTGGGTGAGACA
GGCACCTGGACAGAGGCTGGAGTGGATGGGCTGGATCAACGCCGGCAACGGCAATAC
AAAGTACTCTCAGAAGTTTCAGGGCCGCGTGACAATCACCCGGGACACATCCGCCTCT
ACCGCCTATATGGAGCTGAGCTCCCTGCGGTCCGAGGATACCGCCGTGTACTATTGCG
CCAGAATGAATCACATGATCCCACTGAAGGCATGGGGACAGGGCACACTGGTGACCG
TGTCTAGCGGAGGAGGAGGCAGCGGAGGAGGAGGCTCCGGCGGCTCTGCCCTGGCCA
TCCAGATGACCCAGTCCCCATCCTCTCTGAGCGCCTCCGTGGGCGACCGCGTGACAAT
CACCTGTCGGGCCAGCCAGGGCATCAGAAACGATCTGGGCTGGTACCAGCAGAAGCC
CGGCAAGGCCCCTAAGCTGCTGATCTATGCAGCAAGCTCCCTGCAGTCTGGAGTGCCT
AGCCGGTTCTCTGGCAGCGGCTCCGGAACAGACTTTACACTGACCATCTCTAGCCTGC
AGCCAGAGGATTTCGCCACCTACTATTGCCTGCAGATGTACAATTATAGAACATTTGG
CCAGGGCACCAAGCTGGAGATCAAGAGGGCC SEQ ID NO: 3 is the amino acid sequence of an exemplary IL-13Rα2-CAR.
MALPVTALLLPLALLLHAARPQVQLVQSGAEVKKPGASVKVSCKASGYTFTSYAMHWVR
QAPGQRLEWMGWINAGNGNTKYSQKFQGRVTITRDTSASTAYMELSSLRSEDTAVYYCA
RMNHMIPLKAWGQGTLVTVSSGGGGSGGGGSGGSALAIQMTQSPSSLSASVGDRVTITCR
ASQGIRNDLGWYQQKPGKAPKLLIYAASSLQSGVPSRFSGSGSGTDFTLTISSLQPEDFATY
YCLQMYNYRTFGQGTKLEIKRAAKPTTTPAPRPPTPAPTIASQPLSLRPEACRPAAGGAVH
TRGLDFACDFWVLVVVGGVLACYSLLVTVAFIIFWVRSKRSRGGHSDYMNMTPRRPGPTR
KHYQPYAPPRDFAAYRSVDKRGRKKLLYIFKQPFMRPVQTTQEEDGCSCRFPEEEEGGCEL
GGGRVKFSRSADAPAYQQGQNQLYNELNLGRREEYDVLDKRRGRDPEMGGKPQRRKNP
QEGLYNELQKDKMAEAYSEIGMKGERRRGKGHDGLYQGLSTATKDTYDALHMQALPPR SEQ ID NO: 4 is an exemplary nucleic acid sequence encoding the IL-13Rα2-CAR construct of SEQ ID NO: 3.
ATGGCACTGCCTGTGACCGCCCTGCTGCTGCCACTGGCCCTGCTGCTGCACGCAGCCCG
GCCACAGGTGCAGCTGGTGCAGAGCGGAGCAGAGGTGAAGAAGCCAGGAGCCTCTGT
GAAGGTGAGCTGCAAGGCCTCCGGCTACACATTCACCTCCTATGCCATGCACTGGGTG
AGACAGGCACCTGGACAGAGGCTGGAGTGGATGGGCTGGATCAACGCCGGCAACGGC
AATACAAAGTACTCTCAGAAGTTTCAGGGCCGCGTGACAATCACCCGGGACACATCCG
CCTCTACCGCCTATATGGAGCTGAGCTCCCTGCGGTCCGAGGATACCGCCGTGTACTAT
TGCGCCAGAATGAATCACATGATCCCACTGAAGGCATGGGGACAGGGCACACTGGTG
ACCGTGTCTAGCGGAGGAGGAGGCAGCGGAGGAGGAGGCTCCGGCGGCTCTGCCCTG
GCCATCCAGATGACCCAGTCCCCATCCTCTCTGAGCGCCTCCGTGGGCGACCGCGTGA
CAATCACCTGTCGGGCCAGCCAGGGCATCAGAAACGATCTGGGCTGGTACCAGCAGA
AGCCCGGCAAGGCCCCTAAGCTGCTGATCTATGCAGCAAGCTCCCTGCAGTCTGGAGT
GCCTAGCCGGTTCTCTGGCAGCGGCTCCGGAACAGACTTTACACTGACCATCTCTAGCC
TGCAGCCAGAGGATTTCGCCACCTACTATTGCCTGCAGATGTACAATTATAGAACATTT
GGCCAGGGCACCAAGCTGGAGATCAAGAGGGCCGCCAAGCCAACCACAACCCCAGCA
CCTCGCCCCCCTACACCAGCACCAACCATCGCATCCCAGCCTCTGTCTCTGAGACCAGA
GGCATGTAGGCCAGCAGCAGGAGGAGCAGTGCACACAAGGGGCCTGGACTTCGCCTG
CGATTTTTGGGTGCTGGTGGTGGTGGGAGGCGTGCTGGCCTGTTACTCTCTGCTGGTGA
CCGTGGCCTTCATCATCTTTTGGGTGAGGAGCAAGCGGAGCAGGGGAGGACACAGCG
ACTACATGAACATGACACCACGGAGACCTGGACCAACCAGGAAGCACTACCAGCCTT
ATGCACCACCAAGGGACTTCGCAGCATACCGCAGCGTGGATAAGAGAGGCAGGAAGA
AGCTGCTGTATATCTTCAAGCAGCCCTTCATGCGGCCCGTGCAGACAACCCAGGAGGA
GGACGGCTGCTCCTGTAGATTCCCCGAGGAGGAGGAGGGAGGATGTGAGCTGGGAGG
CGGCAGAGTGAAGTTTTCTCGGAGCGCCGATGCACCTGCATACCAGCAGGGACAGAAT
CAGCTGTATAACGAGCTGAATCTGGGCAGGCGCGAGGAGTACGACGTGCTGGATAAG
AGGCGGGGCCGGGACCCCGAGATGGGAGGCAAGCCACAGAGGCGCAAGAACCCCCA
GGAGGGCCTGTACAATGAGCTGCAGAAGGACAAGATGGCCGAGGCCTATTCCGAGAT
CGGCATGAAGGGAGAGCGGAGAAGGGGCAAGGGACACGATGGCCTGTACCAGGGCCT
GTCTACAGCCACCAAGGACACCTATGATGCCCTGCACATGCAGGCCCTGCCTCCACGC
TAAGCGGCCGC SEQ ID NO: 5 is the amino acid sequence of an exemplary CD8α signal peptide.
MALPVTALLLPLALLLHAARP SEQ ID NO: 6 is the amino acid sequence of an exemplary CD8α hinge domain.
AKPTTTPAPRPPTPAPTIASQPLSLRPEACRPAAGGAVHTRGLDFAC SEQ ID NO: 7 is the amino acid sequence of an exemplary CD28 transmembrane domain (CD28TM).
DFWVLVVVGGVLACYSLLVTVAFIIFWVR -continued

```
SEQ ID NO: 8 is the amino acid sequence of an exemplary CD28 cytoplasmic signaling
domain.
SKRSRGGHSDYMNMTPRRPGPTRKHYQPYAPPRDFAAYRSVD

SEQ ID NO: 9 is the amino acid sequence of an exemplary 4-1BB cytoplasmic signaling
domain.
KRGRKKLLYIFKQPFMRPVQTTQEEDGCSCRFPEEEEGGCEL

SEQ ID NO: 10 is the amino acid sequence of an exemplary CD32 cytoplasmic signaling
domain.
RVKFSRSADAPAYQQGQNQLYNELNLGRREEYDVLDKRRGRDPEMGGKPQRRKNPQEGL
YNELQKDKMAEAYSEIGMKGERRRGKGHDGLYQGLSTATKDTYDALHMQALPPR

SEQ ID NO: 11 is an exemplary nucleic acid sequence encoding the CD8α signal peptide
of SEQ ID NO: 5.
ATGGCACTGCCTGTGACCGCCCTGCTGCTGCCACTGGCCCTGCTGCTGCACGCAGCCCGGCC
AC

SEQ ID NO: 12 is an exemplary nucleic acid sequence encoding the CD8α hinge domain
of SEQ ID NO: 6.
GCCAAGCCAACCACAACCCCAGCACCTCGCCCCCCTACACCAGCACCAACCATCGCATCCC
AGCCTCTGTCTCTGAGACCAGAGGCATGTAGGCCAGCAGCAGGAGGAGCAGTGCACACAA
GGGGCCTGGACTTCGCCTGC

SEQ ID NO: 13 is an exemplary nucleic acid sequence encoding the CD28 transmembrane
domain (CD28TM) of SEQ ID NO: 7.
GATTTTTGGGTGCTGGTGGTGGTGGGAGGCGTGCTGGCCTGTTACTCTCTGCTGGTGAC
CGTGGCCTTCATCATCTTTTGGGTGAGG

SEQ ID NO: 14 is an exemplary nucleic acid sequence encoding the CD28 cytoplasmic
signaling domain of SEQ ID NO: 8.
AGCAAGCGGAGCAGGGGAGGACACAGCGACTACATGAACATGACACCACGGAGACCTGG
ACCAACCAGGAAGCACTACCAGCCTTATGCACCACCAAGGGACTTCGCAGCATACCGCAG
C

SEQ ID NO: 15 is an exemplary nucleic acid sequence encoding the 4-1BB cytoplasmic
signaling domain of SEQ ID NO: 9.
AAGAGAGGCAGGAAGAAGCTGCTGTATATCTTCAAGCAGCCCTTCATGCGGCCCGTGCAGA
CAACCCAGGAGGAGGACGGCTGCTCCTGTAGATTCCCCGAGGAGGAGGAGGGAGGATGTG
AGCTG

SEQ ID NO: 16 is an exemplary nucleic acid sequence encoding the CD32 cytoplasmic
signaling domain of SEQ ID NO: 10.
AGAGTGAAGTTTTCTCGGAGCGCCGATGCACCTGCATACCAGCAGGGACAGAATCAGCTG
TATAACGAGCTGAATCTGGGCAGGCGCGAGGAGTACGACGTGCTGGATAAGAGGCGGGG
CCGGGACCCCGAGATGGGAGGCAAGCCACAGAGGCGCAAGAACCCCCAGGAGGGC
CTGTACAATGAGCTGCAGAAGGACAAGATGGCCGAGGCCTATTCCGAGATCGGCATG
AAGGGAGAGCGGAGAAGGGGCAAGGGACACGATGGCCTGTACCAGGGCCTGTCTACAGC
CACCAAGGACACCTATGATGCCCTGCACATGCAGGCCCTGCCTCCACGC

SEQ ID NO: 17 is the nucleic acid sequence of an exemplary siRNA for silencing IL-13Rα2.
GCTACCATTTGGTTTCATCTT

SEQ ID NO: 18 is the amino acid sequence of an exemplary scFv IL-13Ra2 CAR
MALPVTALLLPLALLLHAARPQVQLVQSGAEVKKPGASVKVSCKASGYTFTSYAMHWVRQAP
GQRLEWMGWINAGNGNTKYSQKFQGRVTITRDTSASTAYMELSSLRSEDTAVYYCARMNHMI
PLKAWGQGTLVTVSSGGGGSGGGGSGGSALAIQMTQSPSSLSASVGDRVTITCRASQGIRNDLG
WYQQKPGKAPKLLIYAASSLQSGVPSRFSGSGSGTDFTLTISSLQPEDFATYYCLQMYNYRTFG
QGTKLEIKRAAKPTTTPAPRPPTPAPTIASQPLSLRPEACRPAAGGAVHTRGLDFACDFWVLVVV
GGVLACYSLLVTVAFIIFWVRSKRSRGGHSDYMNMTPRRPGPTRKHYQPYAPPRDFAAYRSVD
KRGRKKLLYIFKQPFMRPVQTTQEEDGCSCRFPEEEEGGCELGGGRVKFSRSADAPAYQQGQN
QLYNELNLGRREEYDVLDKRRGRDPEMGGKPQRRKNPQEGLYNELQKDKMAEAYSEIGMKGE
RRRGKGHDGLYQGLSTATKDTYDALHMQALPPR
```

DETAILED DESCRIPTION

I. Terms

Unless otherwise noted, technical terms are used according to conventional usage. Definitions of common terms in molecular biology may be found in *Lewin's Genes X*, ed. Krebs et al., Jones and Bartlett Publishers, 2009 (ISBN 0763766321); Kendrew et al. (eds.), *The Encyclopedia of Molecular Biology*, published by Blackwell Publishers, 1994 (ISBN 0632021829); Robert A. Meyers (ed.), *Molecular Biology and Biotechnology: a Comprehensive Desk Reference*, published by Wiley, John & Sons, Inc., 1995 (ISBN 0471186341); and George P. Rédei, *Encyclopedic Dictionary of Genetics, Genomics, Proteomics and Informatics*, 3rd Edition, Springer, 2008 (ISBN: 1402067534), and other similar references.

Unless otherwise explained, all technical and scientific terms used herein have the same meaning as commonly understood by one of ordinary skill in the art to which this disclosure belongs. The singular terms "a," "an," and "the" include plural referents unless the context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description.

Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

In order to facilitate review of the various embodiments of the disclosure, the following explanations of specific terms are provided:

Antibody: A polypeptide ligand comprising at least one variable region that recognizes and binds (such as specifically recognizes and specifically binds) an epitope of an antigen. Mammalian immunoglobulin molecules are composed of a heavy (H) chain and a light (L) chain, each of which has a variable region, termed the variable heavy ($V_H$) region and the variable light ($V_L$) region, respectively. Together, the $V_H$ region and the $V_L$ region are responsible for binding the antigen recognized by the antibody. There are five main heavy chain classes (or isotypes) of mammalian immunoglobulin, which determine the functional activity of an antibody molecule: IgM, IgD, IgG, IgA and IgE.

Antibody variable regions contain "framework" regions and hypervariable regions, known as "complementarity determining regions" or "CDRs." The CDRs are primarily responsible for binding to an epitope of an antigen. The framework regions of an antibody serve to position and align the CDRs in three-dimensional space. The amino acid sequence boundaries of a given CDR can be readily determined using any of a number of well-known numbering schemes, including those described by Kabat et al. (*Sequences of Proteins of Immunological Interest*, U.S. Department of Health and Human Services, 1991; the "Kabat" numbering scheme), Chothia et al. (see Chothia and Lesk, *J Mol Biol* 196:901-917, 1987; Chothia et al., *Nature* 342:877, 1989; and Al-Lazikani et al., (JMB 273,927-948, 1997; the "Chothia" numbering scheme), and the ImMunoGeneTics (IMGT) database (see, Lefranc, *Nucleic Acids Res* 29:207-9, 2001; the "IMGT" numbering scheme). The Kabat and IMGT databases are maintained online.

A single-chain fragment variable (scFv) antibody is a genetically engineered molecule containing the $V_H$ and $V_L$ domains of one or more antibody(ies) linked by a suitable polypeptide linker as a genetically fused single chain molecule (see, for example, Bird et al., *Science,* 242:423-426, 1988; Huston et al., *Proc. Natl. Acad. Sci.,* 85:5879-5883, 1988; Ahmad et al., *Clin. Dev. Immunol.,* 2012, doi:10.1155/2012/980250; Marbry, *IDrugs,* 13:543-549, 2010). The intramolecular orientation of the $V_H$-domain and the $V_L$-domain in a scFv, is typically not decisive for scFvs. Thus, scFvs with both possible arrangements ($V_H$-domain-linker domain-$V_L$-domain; $V_L$-domain-linker domain-$V_H$-domain) may be used. In a dsFv the $V_H$ and $V_L$ have been mutated to introduce a disulfide bond to stabilize the association of the chains. Diabodies also are included, which are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., *Proc. Natl. Acad. Sci.,* 90:6444-6448, 1993; Poljak et al., *Structure,* 2:1121-1123, 1994).

Antibodies also include genetically engineered forms such as chimeric antibodies (such as humanized murine antibodies) and heteroconjugate antibodies (such as bispecific antibodies). See also, *Pierce Catalog and Handbook,* 1994-1995 (Pierce Chemical Co., Rockford, IL); Kuby, J., *Immunology,* 3rd Ed., W.H. Freeman & Co., New York, 1997.

Cancer: A disease characterized by abnormal or uncontrolled cell growth. Other features often associated with cancer include metastasis, interference with the normal functioning of neighboring cells, release of cytokines or other secretory products at abnormal levels, suppression or aggravation of inflammatory or immunological response, invasion of surrounding or distant tissues or organs, such as lymph nodes, etc. "Metastatic disease" refers to cancer cells that have left the original tumor site and migrated to other parts of the body, for example via the bloodstream or lymph system.

Checkpoint Inhibitor: Includes inhibitors of cell cycle checkpoints as well as immune checkpoints. Cell cycle checkpoints refer to safeguard mechanisms that ensure a cell correctly completes each cell cycle phase during mitotic division. Checkpoint inhibitors can sensitize cancer cells to DNA damaging drugs by causing cells with DNA damage to bypass the S and G2/M arrest and enter mitosis, leading to cell death by mitotic catastrophe. Cell cycle checkpoint inhibitors are described in more detail by Visconti et al., *J Exp Clin Cancer Res.* 35(1): 153, 2016. Immune checkpoints refer to safeguard mechanisms that prevent autoreactive immune cells. Immune checkpoints activate when an inhibitory receptor of an immune cell (such as a T cell) recognizes antigens on a cell as "self" antigens. While immune checkpoints are important mechanisms to prevent autoimmune disorders, cancerous cells can take advantage of immune checkpoints to suppress or evade immune recognition. Thus, checkpoint inhibitors can help immune cells recognize and eliminate cancerous cells.

Many checkpoint inhibitors are known in the art. Some non-limiting examples include ipilimumab (Yervoy®), nivolumab (Opdivo®), pembrolizumab (Keytruda®), atezolizumab (Tencentriq®), avelumab (Bavencio®), durvalumab (Imfinzi®), cemiplimab (Libtayo®), palbociclib (Ibrance®), ribociclib (Kisquali®), and abemaciclib (Verzenio®). Further examples are provided in Qiu et al., *Journal of the European Society for Therapeutic Radiology and Oncology,* 126(3):450-464, 2018; Visconti et al., *J Exp Clin Cancer Res.* 35(1): 153, 2016; and Mills et al. *Cancer Res.* 77(23): 6489-6498, 2017.

A checkpoint inhibitor may also include a spindle assembly checkpoint inhibitor. For example, spindle assembly checkpoint inhibitors include MK-1775 (AZD1775), taxanes, or *vinca* alkaloids (see Zhou and Giannakakou. *Curr Med Chem Anticancer Agents.* 5:65-71, 2005; and Visconti et al., *J Exp Clin Cancer Res.* 35(1): 153, 2016).

Chimeric antigen receptor (CAR): A chimeric molecule that includes an antigen-binding portion (such as a single domain antibody or scFv) and a signaling domain, such as a signaling domain from a T cell receptor (e.g., CD3ζ). Typically, CARs include an antigen-binding portion, a transmembrane domain, and an intracellular domain. The intracellular domain typically includes a signaling chain having an immunoreceptor tyrosine-based activation motif (ITAM), such as CD3ζ or FcεRIγ. In some instances, the intracellular domain also includes the intracellular portion of at least one additional co-stimulatory domain, such as CD28, 4-1BB (CD137), ICOS, OX40 (CD134), CD27 and/or DAP10.

Complementarity determining region (CDR): A region of hypervariable amino acid sequence that defines the binding affinity and specificity of an antibody. The light and heavy chains of a mammalian immunoglobulin each have three CDRs, designated VL-CDR1, VL-CDR2, VL-CDR3 and VH-CDR1, VH-CDR2, VH-CDR3, respectively.

Effective Amount: The amount of an agent, such as the disclosed IL-13Rα2-CAR-T cells or IL-13Rα2-CAR-NK cells, that is sufficient to treat, reduce, and/or ameliorate the symptoms and/or underlying cause of a disease or pathological condition, such as cancer in a subject. In a non-limiting example, an effective amount is an amount sufficient to inhibit or reduce tumor growth in the subject.

Histone Deacetylase (HDAC) Inhibitors: Several HDAC inhibitors have been shown to induce cell growth arrest and apoptosis, and thus are potential anti-cancer therapeutics. Some non-limiting examples of HDAC inhibitors include trichostatin A (TSA), suberoylanilide hydroxamic acid (SAHA), sodium butyrate (NaB), SP600125 (Sigma-Aldrich), SRi1302 (Tocris Bioscience), and romidepsin (see Marks and Jiang, *Cell Cycle* 2005, 4:549-551; Duvic et al. *Blood* 109:31-39, 2007; and Fujisawa et al. *Journal of Translational Medicine* 9:37, 2011).

IL-13-PE Immunotoxin: IL-13-PE is a recombinant immunotoxin consisting of IL-13 and a truncated *Pseudomonas* exotoxin. IL-13-PE has been shown to be highly cytotoxic to tumor cells expressing high levels of IL-13Rα2 both in vitro and in vivo. (see Debinski et al., *Clin Cancer Res.* 1:1253-1258, 1995; Debinski et al., *Biol Chem.* 270:16775-16780, 1995; and Joshi et al. *Clin Cancer Res.* 8:1948-1956, 2002).

Interleukin-13 Receptor α2 (IL-13Rα2): IL-13Rα2 is a high affinity receptor for the pleiotropic immune regulatory cytokine interleukin-13 (IL-13) and a known tumor antigen. The significance of IL-13Rα2 expression in cancer is not known and the mechanism of upregulation is still unclear, however, it has been shown that IL-13Rα2 is overexpressed in a variety of human cancers, including malignant glioma, head and neck cancer, Kaposi's sarcoma, renal cell carcinoma, and ovarian carcinoma. Further, in a recent study, it has been shown that 71% of pancreatic tumors overexpress IL-13Rα2 (Fujisawa et al. *Journal of Translational Medicine* 9:37, 2011).

Isolated: An "isolated" biological component, such as a nucleic acid, protein (including antibodies) or cell, that has been substantially separated or purified away from other biological components in the environment (such as a cell) in which the component occurs, e.g., other chromosomal and extra-chromosomal DNA and RNA, proteins and cells. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Macrophage: Large, migratory mononuclear phagocytic cells derived from bone marrow precursors that are found in most tissues of the human body. Macrophages express pattern recognition receptors (PRRs), including Toll-like receptors (TLRs), C-type lectin receptors, scavenger receptors, retinoic acid-inducible gene 1 (RIG1)-like helicase receptors (RLRs) and NOD-like receptors, to recognize signals associated with pathogens, foreign substances, and dead or dying cells.

Macrophages are highly heterogenous and include several sub-classes. Classically activated macrophages (M1 macrophages) mediate defense of the host from various pathogens (e.g., bacteria, protozoa, and viruses) and also mediate anti-tumor immune responses. Alternatively activated macrophages (M2 macrophages) have an anti-inflammatory role and regulate wound healing. Regulatory macrophages secrete large amounts of interleukin-10 (IL-10) in response to Fc receptor-γ ligation. Less-well-defined macrophage subsets include tumor-associated macrophages, which suppress anti-tumor immunity, and myeloid-derived suppressor cells (Murray et al. (2011) *Nat Rev Immunol* 11:723-737).

Natural Killer (NK) cells: Cells of the immune system that kill target cells in the absence of a specific antigenic stimulus and without restriction according to MHC class. Target cells can be tumor cells or cells harboring viruses. NK cells are characterized by the presence of CD56 and the absence of CD3 surface markers. NK cells typically comprise approximately 10 to 15% of the mononuclear cell fraction in normal peripheral blood. Historically, NK cells were first identified by their ability to lyse certain tumor cells without prior immunization or activation. NK cells are thought to provide a "back up" protective mechanism against viruses and tumors that might escape the CTL response by down-regulating MHC class I presentation. In addition to being involved in direct cytotoxic killing, NK cells also serve a role in cytokine production, which can be important to control cancer and infection.

In some examples, a "modified NK cell" is a NK cell transduced or transfected with a heterologous nucleic acid (such as one or more of the nucleic acids or vectors disclosed herein) or expressing one or more heterologous proteins. The terms "modified NK cell" and "transduced NK cell" are used interchangeably in some examples herein.

Pharmaceutically Acceptable Carrier: Includes any and all solvents, dispersion media, coatings, antibacterial and antifungal agents, isotonic and absorption delaying agents, and the like, compatible with pharmaceutical administration (see, e.g., *Remington: The Science and Practice of Pharmacy*, Adejare (Ed.), Academic Press, London, United Kingdom, 23$^{rd}$ Edition (2021). Examples of such carriers or diluents include, but are not limited to, water, saline, Ringer's solutions, dextrose solution, balanced salt solutions, and 5% human serum albumin. Liposomes and non-aqueous vehicles such as fixed oils may also be used. Supplementary active compounds can also be incorporated into the compositions. Actual methods for preparing administrable compositions include those provided in *Remington: The Science and Practice of Pharmacy*, Adejare (Ed.), Academic Press, London, United Kingdom, 23$^{rd}$ Edition (2021).

Purified: The term purified does not require absolute purity; rather, it is intended as a relative term. Thus, for example, a purified protein, nucleic acid, or cell preparation is one in which the protein, nucleic acid, or cell is more enriched than the protein, nucleic acid, or cell is in its initial environment. In one embodiment, a preparation is purified such that the protein, nucleic acid, or cell represents at least 50% of the total content of the preparation. A substantially purified protein or nucleic acid is at least 60%, 70%, 80%, 90%, 95% or 98% pure. Thus, in one specific, non-limiting example, a substantially purified protein or nucleic acid is 90% free of other components.

Recombinant: A nucleic acid or protein that has a sequence that is not naturally occurring or has a sequence that is made by an artificial combination of two otherwise separated segments of sequence (e.g., a "chimeric" sequence). This artificial combination can be accomplished by chemical synthesis or by the artificial manipulation of isolated segments of nucleic acids, for example, by genetic engineering techniques.

Subject: Living multi-cellular vertebrate organisms, a category that includes human and non-human mammals, including but not limited to non-human primates, rodents, and the like. In specific examples disclosed herein, the subject is human.

T cell: A white blood cell (lymphocyte) that is an important mediator of the immune response. T cells include, but are not limited to, $CD4^+$ T cells and $CD8^+$ T cells. A $CD4^+$ T cell is an immune cell that carries a marker on its surface known as "cluster of differentiation 4" (CD4). These cells, also known as helper T cells, help orchestrate the immune response, including antibody responses as well as killer T cell responses. $CD8^+$ T cells carry the "cluster of differentiation 8" (CD8) marker. In one embodiment, a $CD8^+$ T cell is a cytotoxic T lymphocyte (CTL). In another embodiment, a $CD8^+$ cell is a suppressor T cell.

Activated T cells can be detected by an increase in cell proliferation and/or expression or secretion of one or more cytokines (such as IL-2, IL-4, IL-6, IFN-γ, or TNFα). Activation of $CD8^+$ T cells can also be detected by an increase in cytolytic activity in response to an antigen.

A natural killer T (NKT) cell is a class of T cell that expresses both T-cell receptors (TCR) characteristic of adaptive immunity, and surface receptors for NK cells, which are part of the innate immune response (e.g., the cell-surface marker NK1.1 normally associated with NK cells along with an α/β T-cell receptor) (Tupin et al. (2007) *Nat Rev Microbiol* 5:405-417).

In some examples, a "modified T cell" is a T cell transduced or transfected with a heterologous nucleic acid (such as one or more of the nucleic acids or vectors disclosed herein) or expressing one or more heterologous proteins. The terms "modified T cell" and "transduced T cell" are used interchangeably in some examples herein. Similarly, a "modified NKT cell" is an NKT cell transduced or transfected with a heterologous nucleic acid (such as one or more of the nucleic acids or vectors disclosed herein) or expressing one or more heterologous proteins.

Transduced or Transformed: A transformed cell is a cell into which a nucleic acid molecule has been introduced by molecular biology techniques. As used herein, the terms transduction and transformation encompass all techniques by which a nucleic acid molecule might be introduced into such a cell, including transduction or transfection with viral vectors, the use of plasmid vectors, and introduction of DNA by electroporation, lipofection, and particle gun acceleration.

Treating or ameliorating a disease: "Treating" refers to a therapeutic intervention that decreases or inhibits a sign or symptom of a disease or pathological condition after it has begun to develop, such as a reduction in tumor size or tumor burden. "Ameliorating" refers to the reduction in the number or severity of signs or symptoms of a disease, such as cancer.

Vector: A nucleic acid molecule that can be introduced into a host cell (for example, by transfection or transduction), thereby producing a transformed host cell. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant nucleic acid vectors having at least some nucleic acid sequences derived from one or more viruses. A replication deficient viral vector is a vector that requires complementation of one or more regions of the viral genome required for replication due to a deficiency in at least one replication-essential gene function.

II. Overview of Several Embodiments

Disclosed herein are interleukin-13 receptor α2 (IL-13Rα2) binding agents, including an scFv. Also disclosed are chimeric antigen receptors (CARs) that include an IL-13Rα2-specific binding agent (such as an IL-13Rα2 scFv disclosed herein) fused to a hinge region, a transmembrane domain and an intracellular domain comprising one or more signaling domains (e.g., one or more co-stimulatory domains). In some examples, the one or more signaling domains are from CD28, 4-1BB and/or CD3ζ. In some examples, the hinge region is from CD8α and the transmembrane region is from CD28. The CAR may also encode a signal peptide, such as a CD8α signal peptide. Also provided are nucleic acids encoding IL-13Rα2-specific binding agents and IL-13Rα2-CARs and vectors including the nucleic acids.

Also provided herein are immune cells (e.g., T cells, NK cells, NKT cells, or macrophages) transformed with a nucleic acid or vector encoding an IL-13Rα2-specific binding agent or an IL-13Rα2-CAR. In some examples the immune cell expresses an IL-13Rα2-CAR. The cells can be obtained from a blood sample, for example, from peripheral blood of a subject, prior to transforming with a nucleic acid or vector.

Also provided are methods of treating a cancer that expresses IL-13Rα2 in a subject. In some embodiments, the method includes administering to the subject an effective amount of immune cells expressing an IL-13Rα2-CAR. In some examples, the immune cells are autologous to the subject. In other examples, the immune cells are allogeneic. In some examples, the subject receives an additional treatment, such as surgery, radiation, chemotherapy, an additional immunotherapy, administration of a histone deacetylase (HDAC) inhibitor, administration of a cell cycle and/or checkpoint inhibitor, administration of adrenomedullin, administration of an IL-13-PE immunotoxin, or any combination of two or more thereof. In some examples, the subject has cancer, for example, pancreatic cancer, glioblastoma, head and neck squamous cell carcinoma, ovarian cancer, uterine cancer, prostate cancer, breast cancer, melanoma, non-small cell lung cancer (NSCLC), renal cell carcinoma, Kaposi sarcoma, or adrenal carcinoma.

III. IL-13Rα2 Specific Binding Agents

Disclosed herein is an interleukin-13 receptor α2 (IL-13Rα2) binding agent, that in some examples is used as the targeting portion of a chimeric antigen receptor (CAR). In some embodiments, the IL-13Rα2 binding agent is a single-chain fragment variable (scFv) that specifically binds IL-13Rα2.

In some embodiments, the IL13-Rα2 binding agent is an antibody or scFv that includes the CDR sequences provided in Table 1. In some examples, the antibody or scFv specifically binds IL-13Rα2 and includes the variable heavy chain (VH) domain complementarity determining region 1 (CDR1), CDR2, and CDR3 amino acid sequences of SEQ ID NO: 1, and variable light chain (VL) domain complementarity determining region 1 (CDR1), CDR2, and CDR3 of SEQ ID NO: 1, respectively. In some examples, the antibody or scFv includes an amino acid sequence having at least 90% sequence identity (for example, at least 91%, at least 92%, at least 93%, at least 94%, at least 95%, at least 96%, at least 97%, at least 98% or at least 99% sequence identity) to the $V_H$ and $V_L$ sequences disclosed herein. In some examples, the $V_H$ domain includes amino acids 1-118 of SEQ ID NO: 1 and the $V_L$ domain includes amino acids 134-239 of SEQ ID NO: 1.

In some embodiments, the binding agent is an scFv that includes the CDR amino acid sequences provided in Table 1, and has at least 90% sequence identity (for example, at least 91%, at least 92%, at least 93%, at least 94%, at least 95%, at least 96%, at least 97%, at least 98% or at least 99% sequence identity) to the amino acid sequence of SEQ ID NO: 1. In other embodiments, the binding agent is an scFv and includes or consists of the amino acid sequence of SEQ ID NO: 1.

sequence identity (for example, at least 91%, at least 92%, at least 93%, at least 94%, at least 95%, at least 96%, at least 97%, at least 98% at least 99% identity) to SEQ ID NO: 1 or including or consisting of the amino acid sequence of SEQ ID NO: 1.

In some embodiments, the hinge domain is a CD8α hinge domain for example including or consisting of the amino acid sequence of SEQ ID NO: 6. Other hinge domains can be used, such as hinge regions from other immunoglobulins (for example, IgG1, IgG4, or IgD) or a hinge region from CD28, or CD40. In some embodiments, the transmembrane domain is a CD28 transmembrane domain, for example including or consisting of the amino acid sequence of SEQ ID NO: 7. The transmembrane domain can also be from other T cell proteins, such as CD8, CD4, CD3ζ, CD40,

TABLE 1

Location of the CDRs in the IL-13Rα2 scFv sequence

| CDR | Amino Acid Sequence (Position in SEQ ID NO: 1) | Nucleic Acid Sequence (Position in SEQ ID NO: 2) |
|---|---|---|
| VH CDR1 | SYAMH (31-35) | TCCTATGCCATGCAC (90-104) |
| VH CDR2 | WINAGNGNTKYSQKFQG (50-66) | TGGATCAACGCCGGCAACGGCAA TACAAAGTACTCTCAGAAGTTTCA GGGC (147-197) |
| VH CDR3 | MNHMIPLKA (99-107) | ATGAATCACATGATCCCACTGAAG GCA (294-320) |
| VL CDR1 | RASQGIRNDLG (157-167) | CGGGCCAGCCAGGGCATCAGAAA CGATCTGGGC (468-500) |
| VL CDR2 | AASSLqS (183-189) | GCAGCAAGCTCCCTGCAGTCT (546-566) |
| VL CDR3 | LQMYNYRT (222-229) | CTGCAGATGTACAATTATAGAACA (663-686) |

In some embodiments, the scFv binds a target cell, such as a cell expressing IL-13Rα2. In some examples, the cell is a cancer cell (including a tumor cell), such as a pancreatic cancer, glioblastoma, head and neck squamous cell carcinoma, ovarian cancer, uterine cancer, prostate cancer, breast cancer, melanoma, non-small cell lung cancer (NSCLC), renal cell carcinoma, Kaposi sarcoma, or adrenal carcinoma cell. scFv binding may be increased or improved when IL-13Rα2 expression is upregulated in the target cell.

IV. IL-13Rα2 Chimeric Antigen Receptors

Provided herein are IL-13Rα2 chimeric antigen receptors (IL-13Rα2-CARs) that include the IL13-Rα2 specific binding agents described in Section III. In some embodiments, the IL-13Rα2 CAR includes (a) an antigen binding domain including an IL-13Rα2-specifc scFv (such as SEQ ID NO: 1); (b) a hinge domain; (c) a transmembrane domain; and (d) an intracellular domain including one or more signaling domains. The CAR may also include a signal peptide, linker(s), and/or sequences for recombinant construction (such as a restriction enzyme site).

In some embodiments, the antigen binding domain is an IL-13Rα2-specifc scFv, such as those described in Section II. In some examples, the CAR includes an IL-13Rα2 scFv including an amino acid sequence with at least 90%

OX40-L, 4-1BB, ICOS, ICOS-L, CD80, CD86, ICAM-1, LFA-1, ICAM-1, CD56, CTLA-4, PD-1, TIM-3, NKP30, NKP44, NKP40, NKP46, B7-H3, PD-L1, PD-2, and CD70.

In some embodiments, the one or more signaling domains include one or more of CD28, 4-1BB (CD137), CD8, CD40, OX40 (CD134), ICOS, CD27, DAP10, DAP12, OX40-L, 4-1BBL, ICOS-L, CD80, CD86, ICAM-1, LFA-1, CD56, CTLA-4, PD-1, PDK, TIM-3, NKP30, NKP44, NKP40, NKP46, B7-H3, PD-L1, PD-2, CD70, CD3ζ, and FcεRIγdomains, or any combination of two or more thereof. In a specific non-limiting example, the one or more signaling domains are CD28, 4-1BB, and CD3ζ signaling domains, for example including or consisting of the amino acid sequences of SEQ ID NOs: 8, 9, and 10, respectively. In some embodiments, the chimeric antigen receptor further includes a signal peptide located N-terminal to the scFv. In some examples, the signal peptide is a CD8α signal peptide, for example including or consisting of the amino acid sequence of SEQ ID NO: 5. Other signal peptides include an IgG signal sequence or a GM-CSF signal sequence.

In a particular example, the IL-13Rα2-CAR includes an amino acid sequence with at least 90% identity (for example, at least 91%, at least 92%, at least 93%, at least 94%, at least 95%, at least 96%, at least 97%, at least 98% at least 99% identity) to the amino acid sequence of SEQ ID NO: 3. In some examples, the IL-13Rα2-CAR includes or consists of the amino acid sequence of SEQ ID NO: 3. In other examples, the IL-13Rα2 CAR does not include the signal peptide, for example, does not include amino acids 1-21 of SEQ ID NO: 3.

In other embodiments, the IL-13Rα2-CAR further includes a domain that increases survival or persistence of an immune cell expressing the CAR. In some examples, the domain is an intracellular domain from a cytokine receptor, for example, an intracellular domain from interleukin (IL)-15 receptor, IL-12 receptor, or IL-18 receptor. In other examples, the domain is an intracellular domain from a growth factor receptor, such as an intracellular domain from CD40, NKG2D, NKP40, or NKP46. In some examples, the domain is located C-terminal to the CD3ζ domain of the CAR. In additional embodiments, the IL-13Rα2-CAR further includes an inducible gene (such as Caspase 9) that can be used to eliminate IL-13Rα2-CAR expressing cells (e.g., a "suicide" gene). The inducible gene can be activated in the event of off target side effects (or on target/off tumor effects), such as cytokine release syndrome ("cytokine storm").

Also provided are functional variants of the IL-13Rα2-CARs or the domains thereof described herein, which retain the biological activity of the CAR of which it is a variant or retains the biological activity of the particular domain. The functional variant can be at least about 80%, about 85%, about 90%, about 91%, about 92%, about 93%, about 94%, about 95%, about 96%, about 97%, about 98%, about 99% or more identical in amino acid sequence to the parent CAR or domain. Substitutions can be made, for example, in one or more of the extracellular targeting domain, hinge domain, transmembrane domain, and intracellular domains.

In some examples, the functional variant includes the amino acid sequence of the parent CAR or domain with at least one conservative amino acid substitution (such as up to 10 conservative amino acid substitutions, for example, 1, 2, 3, 4, 5, 6, 7, 8, 9, or 10 conservative substitutions). In other examples, the functional variant includes the amino acid sequence of the parent CAR or domain with at least one non-conservative amino acid substitution (such as up to 10 non-conservative amino acid substitutions, for example, 1, 2, 3, 4, 5, 6, 7, 8, 9, or 10 non-conservative substitutions). In this case, the non-conservative amino acid substitution does not interfere with or inhibit the biological activity of the functional variant. The non-conservative amino acid substitution may enhance the biological activity of the functional variant, such that the biological activity of the functional variant is increased as compared to the parent CAR or domain.

The CARs or domains thereof can in some examples, include one or more synthetic amino acids in place of one or more naturally occurring amino acids. Such synthetic amino acids include, for example, aminocyclohexane carboxylic acid, norleucine, a-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, -(2-amino-2-norbornane)-carboxylic acid, γ-diaminobutyric acid, α,β-diaminopropionic acid, homophenylalanine, and α-tert-butylglycine. The CARs may be glycosylated, amidated, carboxylated, phosphorylated, esterified, N-acylated, cyclized via, e.g., a disulfide bridge, or converted into an acid addition salt and/or optionally dimerized or polymerized, or conjugated.

V. Nucleic Acids and Vectors

Also provided are nucleic acids encoding the IL13-Rα2 binding agents or IL-13Rα2 chimeric antigen receptors (IL-13Rα2-CAR) disclosed herein.

In some embodiments, the nucleic acid encodes a IL13-Rα2 binding agent. In some examples, the nucleic acid encodes each of the CDR sequences provided in Table 1, for example, the nucleic acid encodes the VH domain CDR1, CDR2, and CDR3 of SEQ ID NO: 1, and encodes the VL domain CDR1, CDR2, and CDR3 of SEQ ID NO: 1, respectively. In some examples, the nucleic acid encodes an amino acid sequence including each of the CDR sequences provided in Table 1, and has at least 90% identity (for example, at least 91%, at least 92%, at least 93%, at least 94%, at least 95%, at least 96%, at least 97%, at least 98% or at least 99% sequence identity) to SEQ ID NO: 1. In some examples, the nucleic acid encodes an amino acid sequence including or consisting of SEQ ID NO: 1. In further examples, the nucleic acid encodes each of the CDR sequences provided in Table 1, and has at least 90% identity (for example, at least 91%, at least 92%, at least 93%, at least 94%, at least 95%, at least 96%, at least 97%, at least 98% or at least 99% sequence identity) to SEQ ID NO: 2. In some examples, the nucleic acid encoding the IL13-Rα2 binding agent includes or consists of SEQ ID NO: 2.

In some embodiments, the nucleic acid encodes the IL-13Rα2-CAR disclosed herein. In some examples, the nucleic acid molecule encodes an amino acid sequence having at least 90% sequence identity (for example, at least 91%, at least 92%, at least 93%, at least 94%, at least 95%, at least 96%, at least 97%, at least 98% or at least 99% sequence identity) to SEQ ID NO: 3. In some examples, the nucleic acid molecule encodes an amino acid sequence that includes each of the CDR sequences provided in Table 1 (the nucleic acid encodes the VH domain CDR1, CDR2, and CDR3 and the VL domain CDR1, CDR2, and CDR3 of SEQ ID NO: 1), and has at least 90% sequence identity (for example, at least 91%, at least 92%, at least 93%, at least 94%, at least 95%, at least 96%, at least 97%, at least 98% or at least 99% sequence identity) to SEQ ID NO: 3. In some examples, the nucleic acid molecule encodes an amino acid sequence including or consisting of SEQ ID NO: 3. In further examples, the nucleic acid molecule encoding the IL-13Rα2-CAR includes a nucleic acid sequence having at least 90% sequence identity (for example, at least 91%, at least 92%, at least 93%, at least 94%, at least 95%, at least 96%, at least 97%, at least 98% or at least 99% sequence identity) to SEQ ID NO: 4. In some examples, the nucleic acid molecule encoding the IL-13Rα2-CAR includes a nucleic acid sequence encoding each of the CDR sequences provided in Table 1, and the nucleic acid has at least 90% sequence identity (for example, at least 91%, at least 92%, at least 93%, at least 94%, at least 95%, at least 96%, at least 97%, at least 98% or at least 99% sequence identity) to SEQ ID NO: 4. In other examples, the nucleic acid molecule encoding the IL-13Rα2-CAR includes or consists of SEQ ID NO: 4.

Also provided are vectors (e.g., plasmids, viral vectors, cosmids, artificial chromosomes) encoding a nucleic acid disclosed herein (e.g., a nucleic acid encoding an IL-13Rα2-specific binding agent or an IL-13Rα2-CAR). Certain vectors are capable of directing the expression of genes to which they are operatively-linked. Such vectors are sometimes referred to as "expression vectors." In some embodiments, a nucleic acid molecule encoding a disclosed IL-13Rα2 scFv or IL-13Rα2-CAR is included in a vector (such as a viral vector) for expression in a host cell, such as an immune cell (e.g., T cell, NK cell, NKT cell, or macrophage).

One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g., retroviruses, replication defective retroviruses, adenoviruses, replication defective adenoviruses, and adeno-associated viruses). A replication deficient viral vector is a vector that requires complementation of one or more regions of the viral genome required for replication due to a deficiency in at least one replication-essential gene function.

In some embodiments, the vector is a viral vector, such as a retrovirus (e.g., MoMLV or lentivirus) or adeno-associated viral (AAV) vector. Other suitable viral vectors include polyoma, SV40, vaccinia virus, herpes viruses including HSV and EBV, Sindbis viruses, alphaviruses and retroviruses of avian, murine, and human origin, baculovirus (*Autographa californica* multinuclear polyhedrosis virus; AcMNPV) vectors, retrovirus vectors, polio vectors, orthopox vectors, avipox vectors, fowlpox vectors, capripox vectors, suipox vectors, adenoviral vectors, herpes virus vectors, alpha virus vectors, baculovirus vectors, Sindbis virus vectors, vaccinia virus vectors and poliovirus vectors. Specific exemplary pox viruses of use include orthopox, suipox, avipox, and capripox virus. Orthopox includes vaccinia, ectromelia, and raccoon pox. One example of an orthopox of use is vaccinia. Avipox includes fowlpox, canary pox and pigeon pox. Capripox includes goatpox and sheeppox. In one example, the suipox is swinepox. In a specific, non-limiting example, the vector is pCDH-MSCV-MCS-EFla-GFP-T2A-Puro lentiviral vector (e.g., Cat #CD713B-1, System Biosciences, Palo Alto, CA 94303).

Vectors can include one or more regulatory elements (e.g., promoter (such as CMV, SV40, EF1α, β-actin, hPGK, or RPBSA); transcription start site (TSS); enhancers; insulators; A/T-rich regions; transcription factor (TF) binding sites; transcription and/or translation terminators; initiation sequences, or other regulatory element), which may be selected on the basis of the host cell to be used for expression, that is operatively-linked to the nucleic acid sequence to be expressed. "Operably linked" means that the nucleotide sequence of interest is linked to the regulatory element(s) in a manner that allows for expression of the nucleotide sequence (e.g., in an in vitro transcription/translation system or in a host cell when the vector is introduced into the host cell). Vector expression can be constitutive (e.g., SV40, CMV, UBC, EFlu, PGK, and CAGG), inducible (e.g., IPTG), or cell/tissue specific (such as T cell specific, e.g., dLck or CD36). In some examples, the promoter is a synthetic promoter that is inducible upon CAR T cell or TCR activation (e.g., "iSynPro" promoters, see, WO 2018/213332). A vector can be introduced into a host cell to express a product encoded by a nucleic acid described herein (e.g., an IL13-Rα2 binding agent or IL-13Rα2-CAR). A vector can also include one or more selectable marker genes, such as an antibiotic (e.g., puromycin, hygromycin), or a detectable marker (e.g., GFP, YFP, RFP, luciferase, X-gal). In some examples, a selectable marker or reporter is not included in the vector.

Vectors can include a safety switch system, such as an inducible proapoptotic molecule (e.g., Fas-associated death domain-containing protein (FADD), Bcl-2-associated death promoter (BAD), or inducible caspase 9 (iCasp9)), or an inducible activation system (e.g., My88/CD40 (iMC)). Further information on safety switch systems can be found, for example, in Gargett and Brown (2014) *Front. Pharmacol.* 5: 235 and Gerken et al. (2017) *Cancer Discov.* 7(11):1306-1319. In some examples, the vector encoding the safety switch is a different vector than the vector encoding an IL-13Rα2-CAR or IL13-Rα2 binding agent disclosed herein. In some examples, the vector encoding the safety switch also encodes the IL-13Rα2-CAR or IL13-Rα2 binding agent.

In some examples, the safety switch is a proapoptotic molecule fused with a FKBP (FK506-binding protein) variant that binds a chemical inducer of dimerization (CID) (e.g., AP1903, AP20187, AP21967). In some examples, a proapoptotic molecule is activated to control growth or eliminate cells transduced or transformed with a vector, such as a vector encoding an IL-13Rα2-CAR or IL13-Rα2 binding agent disclosed herein. In some examples, activation of the inducible proapoptotic molecule eliminates the transduced or transformed cells, for example, by eliminating at least 25%, at least 50%, at least 60%, at least 70%, at least 80%, at least 90%, at least 91%, at least 92%, at least 93%, at least 94%, at least 95%, at least 96%, at least 97%, at least 98% at least 99%, or 100% of the transduced or transformed cells. In some examples, the proapoptotic molecule is activated by contacting a transduced or transformed cell with a CID.

In some examples, the safety switch is an inducible activation system (e.g., My88/CD40 (iMC)). In some examples, the inducible activation system is activated to increase activity of a cell transduced or transformed with a vector, such as a vector encoding an IL-13Rα2-CAR or IL13-Rα2 binding agent disclosed herein. In some examples, activation of the inducible activation system increases activity of transformed cells, for example, by increasing proliferation, cytokine production, or tumor targeting by at least 25%, at least 50%, at least 60%, at least 70%, at least 80%, at least 90%, at least 100%, at least 200%, at least 400%, or more. In some examples, the inducible activation system is activated by contacting a transformed cell with a CID (e.g., AP1903, AP20187, AP21967).

VI. Cells Expressing IL-13Rα2 CARs

Also provided herein are cells (for example, immune cells) that express a disclosed IL-13Rα2-CAR, such as cells that include a nucleic acid disclosed herein (e.g., a nucleic acid encoding an IL13-Rα2 binding agent or IL-13Rα2-CAR disclosed herein), or a vector encoding the nucleic acid. Exemplary immune cells include T cells, NK cells, NKT cells, and/or macrophages. In some examples, the cells are T cells. In some examples, the cells express an IL-13Rα2-CAR having at least 90% identity to SEQ ID NO: 3, or amino acids 22-538 of SEQ ID NO: 3. In some examples, the cells express an IL-13Rα2-CAR including or consisting of SEQ ID NO: 3, or amino acids 22-538 of SEQ ID NO: 3. In some examples, the cells are transduced or transfected with a nucleic acid sequence encoding an amino acid sequence including or consisting of SEQ ID NO: 3, or amino acids 22-538 of SEQ ID NO: 3. In further examples, the cells are transduced or transfected with a nucleic acid sequence having at least 90% identity to SEQ ID NO: 4. In some examples, the nucleic acid sequence includes or consists of SEQ ID NO: 4.

In some embodiments, the cells are isolated immune cells, such as isolated T cells (such as a primary T cell or T cells obtained from a subject), isolated NK cells (such as a primary NK cell or NK cells obtained from a subject), isolated NKT cells, or isolated macrophages. Cell types can be identified based on the presence or absence of expression markers, for example, NK cells are CD56 positive and CD3 negative, T cells can be CD4 or CD8 positive, NKT cells are NK1.1 positive and α/β T-cell receptor positive, and macrophages express a number or receptors, including PRRs, TLRs, C-type lectin receptors, scavenger receptors, RLRs, and NOD-like receptors. In some examples, the cells are isolated T cells. In further examples, the cells are isolated CD8+ T cells. In some examples, the cells are isolated naïve T cells. Naïve T cells express CD45RA, CCR7, CD62L, CD127, and CD132 surface markers, and lack CD25, CD44, CD69, CD45RO, or HLA-DR markers. In some examples, the immune cells are obtained from peripheral blood, lymph node, thymus, bone marrow, tumor tissue, adipose tissue, human embryonic stem cells (hESC), induced pluripotent stem cells (iPSC), or umbilical cord blood, of a subject. In a non-limiting example, the cells are T cells isolated from peripheral blood of a subject. In further examples, the immune cells obtained from the subject are enriched, purified, and/or expanded, for example before and/or after transformation or transduction with a vector or nucleic acid disclosed herein. In some examples, the immune cells (e.g., T cell, NK cell, NKT cell, or macrophage), are harvested and expanded from a subject with cancer. In some examples, the immune cells (e.g., T cell, NK cell, NKT cell, or macrophage), are harvested and expanded from a subject without cancer.

In some embodiments, the cells are a cell type suitable for protein expression and/or production of viruses (e.g., producing retroviruses). Exemplary cell types include microbial (e.g., bacterial or yeast), archea, insect, fungi, plant, or mammalian cells. Non-limiting examples of specific cell lines include *Escherichia coli, Bacillus subtilis, Saccharomyces cerevisiae, Salmonella typhimurium*, SF9 cells, C129 cells, 293 cells, *Neurospora*, and immortalized mammalian myeloid and lymphoid cell lines. Non-limiting examples of commonly used mammalian host cell lines include VERO and HeLa, HEK 293T, CHO, WI38, BHK, and COS cell lines, however, other cell lines may be used, such as cells designed to provide higher expression, or desirable post-translational modifications (e.g., glycosylation patterns), or other features. In some examples, a nucleic acid or vector disclosed herein (e.g., nucleic acids or vectors encoding the IL13-Ra2 binding agent or IL-13Rα2-CAR disclosed herein) is codon optimized for expression in a particular organism, such as a bacterium (e.g., *E. coli*), fungi (e.g., *S. cerevisiae*), plant (e.g., *N. tabacum* NT-1), or animal (e.g., human HEK 293T cells or T cells). Suitable examples of vectors (e.g., expression vectors) are provided above.

In some embodiments, the cells are transduced or transformed (including transfected) with a nucleic acid encoding the IL13-Rα2 binding agent or IL-13Rα2-CAR disclosed herein, or a vector encoding the nucleic acid. Exemplary methods of transforming cells (e.g., immune cells) include chemical transformation (calcium phosphate), electroporation, microinjection, heat shock, lipofection, and particle bombardment. In some examples, the nucleic acid or vector is introduced by contacting the cells with a nanoparticle including the nucleic acid or vector. Transformation can be used for stable or transient expression. Following transformation or transduction, cells expressing the IL-13Rα2-CAR can be detected and/or enriched, for example, by flow cytometry using a labeled antibody that binds to IL-13Rα2. In some examples, transduced or transformed cells (such as T cells, NK cells, NKT cells, or macrophages) are expanded, for example, by cell culture for a period of time following transformation or transduction. In some examples, some or all of the transduced or transformed immune cells are cryopreserved for later use.

VII. Methods of Immunotherapy

Also disclosed herein are methods of treating a subject with cancer, comprising administering an effective amount of cells expressing a disclosed IL-13Rα2-CAR (e.g., immune cells expressing IL-13Rα2-CAR, such as IL-13Rα2-CAR-T cells, IL-13Rα2-CAR-NK cells, IL-13Rα2-CAR-NKT cells, or IL-13Rα2-CAR-macrophage cells). In a specific, non-limiting example, an effective amount of an IL-13Rα2-CAR-T cell is administered to a subject. The cells expressing a disclosed IL-13Rα2-CAR can be generated from immune cells (e.g., T cells, NK cells, NKT cells, or macrophages) isolated from a sample, for example, a peripheral blood sample of a subject, and subsequently transformed or transduced with the IL-13Rα2-CAR. In some examples, the cells are autologous to the subject (from the subject). In other examples, the cells are allogeneic (from a donor). In some examples, the sample is from a subject that has cancer. In some examples, the cells are enriched, purified, and/or expanded after isolation from the sample and/or after transformation or transfection with the IL-13Rα2-CAR.

In some embodiments, the methods include administering to a subject a composition including cells expressing the IL-13Rα2-CAR and a pharmaceutically acceptable carrier. In some examples, the cells include a vector encoding a safety switch system. In some embodiments, the methods include administering to the subject a pharmaceutical composition including a vector encoding the IL-13Rα2-CAR and a pharmaceutically acceptable carrier. In some examples, the vector encodes a safety switch system.

A “pharmaceutically acceptable carrier” includes any and all solvents, dispersion media, coatings, antibacterial and antifungal agents, isotonic and absorption delaying agents, and the like, compatible with pharmaceutical administration (see, e.g., *Remington: The Science and Practice of Pharmacy*, Adejare (Ed.), Academic Press, London, United Kingdom, 23$^{rd}$ Edition (2021). Examples of such carriers or diluents include, but are not limited to, water, saline, Ringer's solutions, dextrose solution, balanced salt solutions, and 5% human serum albumin. Liposomes and non-aqueous vehicles such as fixed oils may also be used. Supplementary active compounds can also be incorporated into the compositions. Actual methods for preparing administrable compositions include those provided in *Remington: The Science and Practice of Pharmacy*, Adejare (Ed.), Academic Press, London, United Kingdom, 23$^{rd}$ Edition (2021).

In some examples, the composition includes about $10^4$ to $10^{12}$ of the IL-13Rα2-CAR cells (for example, about $10^4$-$10^8$ cells, about $10^6$-$10^8$ cells, or about $10^6$-$10^{12}$ cells). In some examples, the composition includes at least about $10^4$, $10^5$, $10^6$, or $10^7$ IL-13Rα2-CAR cells. In other examples, the composition includes no more than about $10^4$, $10^5$, $10^6$, $10^7$ $10^8$, $10^9$, or $10^{10}$ IL-13Rα2-CAR cells. In some examples, the composition may be prepared such that about $10^4$ to $10^{10}$ IL-13Rα2-CAR cells/kg (such as about $10^4$, $10^5$, $10^6$, $10^7$, $10^8$, $10^9$, or $10^{10}$ cells/kg) are administered to a subject. Appropriate doses can be determined through clinical trials.

The population of IL-13Rα2-CAR cells is typically administered parenterally, for example intravenously; however, injection or infusion to a tumor or close to a tumor (e.g., local administration) or administration to the peritoneal cavity can also be used. Appropriate routes of administration can be determined by a skilled clinician based on factors such as the subject, the condition being treated, and other factors.

Multiple doses of the population of IL-13Rα2-CAR cells can be administered to a subject. For example, IL-13Rα2-CAR cells can be administered daily, every other day, twice per week, weekly, every other week, every three weeks, monthly, or less frequently. A skilled clinician can select an administration schedule based on the subject, the condition being treated, the previous treatment history, and other factors.

In some examples, the effective amount of cells expressing a disclosed IL-13Rα2-CAR is an amount sufficient to prevent, treat, reduce, and/or ameliorate one or more signs or symptoms of cancer in the subject. In other examples, the effective amount is an amount sufficient to target and eliminate tumor cells expressing IL-13Rα2. In some examples, the effective amount is an amount sufficient to inhibit or slow cancer growth or metastasis in the subject. In another example, the effective amount is an amount sufficient to reduce tumor load or tumor density in the subject.

In some embodiments, the subject is further administered one or more cytokine(s) (such as one or more of IL-2, IL-7, IL-15, IL-21, and/or IL-12), for example, to support survival and/or growth of the IL-13Rα2-CAR cells. The cytokine(s) can be administered before, after, or substantially simultaneously with the IL-13Rα2-CAR cells. In some examples, about 1 to about 5 cytokines are administered to the subject, for example, about 1 to about 4, about 1 to about 3, about 1 to about 2, about 2 to about 5, about 2 to about 4, about 2 to about 3, about 3 to about 5, about 3 to about 4, or about 4 to about 5 cytokines are administered, before, after, or substantially simultaneously with the IL-13Rα2-CAR cells. In some examples, at least one of IL-2, IL-7, or IL-15 is administered to the subject before, after, or substantially simultaneously with the IL-13Rα2-CAR cells. In some examples, at least one cytokine (e.g., IL-2, IL-7, and/or IL-15) is administered simultaneously, for example, with IL-13Rα2-CAR cells.

In some examples, the cells expressing a disclosed IL-13Rα2-CAR (e.g., IL-13Rα2-CAR-T cells, IL-13Rα2-CAR-NK cells, IL-13Rα2-CAR-NKT cells, or IL-13Rα2-CAR-macrophage cells) are transformed or transfected with a vector encoding a safety switch system. In some examples a therapeutically effective amount of a CID (e.g., AP1903, AP20187, AP21967) is administered to the subject to activate the safety switch system. The safety switch system can be activated at any desired time, for example, at the conclusion of treatment. In some examples, the CID is administered to control growth or to increase activity of the transformed or transfected cells in the subject. In some examples, the safety switch is an inducible proapoptotic molecule, and the inducible proapoptotic molecule is activated by administering a therapeutically effective amount of a CID to the subject. In some examples, administering the CID eliminates the transformed or transfected cells in the subject, for example by eliminating at least 50%, at least 60%, at least 70%, at least 80%, at least 90%, at least 91%, at least 92%, at least 93%, at least 94%, at least 95%, at least 96%, at least 97%, at least 98% at least 99%, or 100% of the transformed or transfected cells in the subject. In other examples, the safety switch is an inducible activation system, and the inducible activation system is activated by administering an effective amount of a CID to the subject. In some examples, administering the CID increases activity of the transformed or transfected cells in a subject as compared to a suitable control. For example, by increasing proliferation, cytokine production, or tumor targeting by at least 50%, at least 60%, at least 70%, at least 80%, at least 90%, at least 100%, at least 200%, at least 400%, or more of the transformed or transfected cells in the subject. Further information on safety switch systems can be found, for example, in Gargett and Brown (2014) *Front. Pharmacol.* 5: 235 and Gerken et al. (2017) *Cancer Discov.* 7(11):1306-1319.

In some examples, the subject has a cancer that expresses IL-13Rα2. Exemplary cancers include sarcomas, carcinomas, fibrosarcoma, myxosarcoma, liposarcoma, chondrosarcoma, osteosarcoma, and other sarcomas, synovioma, mesothelioma, Ewing's tumor, Kaposi sarcoma, leiomyosarcoma, rhabdomyosarcoma, colon carcinoma, lymphoid malignancy, pancreatic cancer, breast cancer, lung cancers, ovarian cancer, uterine cancer, prostate cancer, hepatocellular carcinoma, squamous cell carcinoma, basal cell carcinoma, adenocarcinoma, adrenal carcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, head and neck cancers, neuroblastoma, retinoblastoma and brain metastasis. Cancer also includes hematological (or hematogenous) cancers, such as leukemia, such as lymphoma, Hodgkin's disease, non-Hodgkin's lymphoma (indolent or high grade forms), multiple myeloma, Waldenstrom's macroglobulinemia, heavy chain disease, myelodysplastic syndrome, hairy cell leukemia or myelodysplasia.

In some examples, the subject has a cancer that over-expresses IL-13Rα2, for example, relative to a non-cancerous cell of the same type. In some examples, the subject has a solid tumor. In further examples, the subject has pancreatic cancer, glioblastoma, head and neck squamous cell carcinoma, ovarian cancer, uterine cancer, prostate cancer, breast cancer, melanoma, non-small cell lung cancer (NSCLC), renal cell carcinoma, Kaposi sarcoma, or adrenal carcinoma. In some embodiments, a subject having a cancer that expresses or over-expresses IL-13Rα2 is selected for treatment.

In some embodiments, the subject receives an additional treatment, such as one or more of surgery, radiation, chemotherapy, additional immunotherapy, or other therapeutic. Exemplary chemotherapeutic agents include (but are not limited to) alkylating agents, such as nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine); antimetabolites such as folic acid analogs (such as methotrexate), pyrimidine analogs (such as 5-FU or cytarabine), and purine analogs, such as mercaptopurine or thioguanine; or natural products, for example vinca alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitocycin C), and enzymes (such as L-asparaginase). Additional agents include platinum coordination complexes (such as cis-diamine-dichloroplatinum II, also known as cisplatin), substituted ureas (such as hydroxyurea), methyl hydrazine derivatives (such as procarbazine), and adrenocrotical suppressants (such as mitotane and aminoglutethimide); hormones and antagonists, such as adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testosterone proprionate and fluoxymesterone). Examples of the most commonly used chemotherapy drugs include adriamycin, melphalan (Alkeran®) Ara-C (cytarabine), carmustine, busulfan, lomustine, carboplatinum, cisplatinum, cyclophosphamide (Cytoxan®), daunorubicin, dacarbazine, 5-fluorouracil, fludarabine, hydroxyurea, idarubicin, ifosfamide, methotrexate, mithramycin, mitomycin, mitoxantrone, nitrogen mustard, paclitaxel (or other taxanes, such as docetaxel), vinblastine, vincristine, VP-16, while newer drugs include gemcitabine (Gemzar®), trastuzumab (Herceptin®), irinotecan (CPT-11), leustatin, navelbine, rituximab (Rituxan®) imatinib (STI-571), Topotecan (Hycamtin®), capecitabine, ibritumomab (Zevalin®), and calcitriol. A skilled clinician can select appropriate additional therapies (from those listed here or other current therapies) for the subject, depending on factors such as the subject, the cancer being treated, treatment history, and other factors.

In some examples, the subject is administered an additional therapeutic, such as a checkpoint inhibitor (e.g., anti-CTLA-4, anti-PD1, or anti-PDL1), a histone deacetylase (HDAC) inhibitor, a cell cycle checkpoint inhibitor, adrenomedullin, an IL-13-PE immunotoxin, or any combination of two or more thereof. The administration of an additional therapeutic may be before, after, or substantially simultaneously with the administration of the cell expressing the IL-13Rα2-CAR.

In some examples, the additional therapeutic increases expression of IL-13Rα2 on tumor cells. For example, it has been reported that treatment with HDAC inhibitors dramatically upregulates IL-13Rα2 in pancreatic cancer cell lines expressing little to no IL-13Rα2. These inhibitors also modestly upregulated IL-13Rα2 in cells expressing higher levels of IL-13Rα2. Upregulation of IL-13Rα2 was found to sensitize pancreatic tumor cells to IL-13-PE, an immunotoxin that targets cells expressing IL-13Rα2, resulting in a synergistic anti-tumor effect (see Fujisawa et al. *Journal of Translational Medicine* 9:37, 2011). Thus, in some examples, the subject is administered an HDAC inhibitor, such as one or more of trichostatin A (TSA), suberoylanilide hydroxamic acid (SAHA), sodium butyrate (NaB), SP600125 (Sigma-Aldrich), SRi1302 (Tocris Bioscience), or romidepsin. In further examples, the subject is administered adrenomedullin, which has also been shown to increase IL-13Rα2 expression (Joshi et al., *Cancer Res.* 68:9311-9317, 2008). In some examples, the HDAC inhibitor or adrenomedullin is administered substantially simultaneously with the cells expressing the IL-13Rα2-CAR. In other examples, the HDAC inhibitor or adrenomedullin is administered prior to administering the cells expressing the IL-13Rα2-CAR, for example, at least 1 day, at least 2 days, at least 3 days, at least 4 days, at least 5 days, at least 6 days, at least 7 days, at least 8 days, at least 9 days, at least 12 days, at least 14 days, at least three weeks, at least four weeks, at least one month, or more prior. Multiple doses of the HDAC inhibitor or adrenomedullin can be administered to a subject, for example, administered twice daily, once daily, every other day, twice per week, weekly, every other week, every three weeks, monthly, or less frequently. A skilled clinician can select an administration schedule based on the subject, the condition being treated, the previous treatment history, tumor load and type, clinical stage and grade of the disease, overall health of the subject, and other factors.

In some examples, the subject is administered a checkpoint inhibitor. In some examples, the checkpoint inhibitor targets PD-1, PD-L1, CTLA-4, CDK4, and/or CDK6. Exemplary inhibitors include ipilimumab, nivolumab, pembrolizumab, atezolizumab, avelumab, durvalumab, cemiplimab, palbociclib, ribociclib, and abemaciclib. The checkpoint inhibitor may be administered substantially simultaneously with the cells expressing the IL-13Rα2-CAR. In some examples, the checkpoint inhibitor is administered prior to administering the cells expressing the IL-13Rα2-CAR, for example, at least 1 day, at least 2 days, at least 3 days, at least 4 days, at least 5 days, at least 6 days, at least 7 days, at least 8 days, at least 9 days, at least 12 days, at least 14 days, at least three weeks, at least four weeks, at least one month, or more prior. Multiple doses of the checkpoint inhibitor can be administered to a subject, for example, administered twice daily, once daily, every other day, twice per week, weekly, every other week, every three weeks, monthly, or less frequently. A skilled clinician can select an administration schedule based on the subject, the condition being treated, the previous treatment history, tumor load and type, clinical stage and grade of the disease and overall health of the subject, and other factors.

In some embodiments, the subject is administered an IL-13 PE immunotoxin, such as a recombinant protein including IL-13 conjugated to a truncated *Pseudomonas* exotoxin (see, e.g., Kioi et al., *Mol. Cancer Ther.* 7(6):1579-1587, 2008). The IL-13 PE immunotoxin may be administered substantially simultaneously with the cells expressing the IL-13Rα2-CAR. In some examples, the IL-13 PE immunotoxin is administered prior to administering the cells expressing the IL-13Rα2-CAR, for example, at least 1 day, at least 2 days, at least 3 days, at least 4 days, at least 5 days, at least 6 days, at least 7 days, at least 8 days, at least 9 days, at least 12 days, at least 14 days, at least three weeks, at least four weeks, at least one month, or more prior. Multiple doses of the IL-13 PE immunotoxin can be administered to a subject, for example, administered twice daily, once daily, every other day, twice per week, weekly, every other week, every three weeks, monthly, or less frequently. A skilled clinician can select an administration schedule based on the subject, the condition being treated, the previous treatment history, tumor load and type, clinical stage and grade of the disease and overall health of the subject, and other factors. Without being bound by any particular theory, it is believed that, administering IL-13-PE prior to the administration of the IL-13Rα2-CAR cells reduces density of tumor stroma cells, thereby creating space in the tumor microenvironment for IL-13Rα2-CAR cells to infiltrate the tumor.

EXAMPLES

The following examples are provided to illustrate certain particular features and/or embodiments. These examples should not be construed to limit the disclosure to the particular features or embodiments described.

Example 1

Materials and Methods

Cell Lines:

Human Jurkat-T cells, A172, U87MG and T98G glioma cells lines were obtained from ATCC and grown according to the supplier's instructions. The U251 glioma cell line was obtained from the National Cancer Institute and maintained in RPMI complete medium with 10% FBS. The T98G and U87MG glioma cell lines were maintained in EMEM complete medium supplemented with 10% FBS. These cell lines were previously characterized for IL-13Rα2 expression by RT-PCR of mRNA and immunocytochemistry (ICC) analyses of protein expression (Joshi et al. (2000) *Cancer Res.* 60:1168-1172). Two IL-13Rα2 positive glioma cells lines, U251 and U87MG were used for IL-13Rα2 gene silencing by siRNA technique using SureSilencing® shRNA plasmids (Qiagen (Gaithersburg, MD)) following the manufacturer's instructions. These cell lines served as negative controls in some biological assays.

Design of Lentiviral Vector Encoding scFv-IL-13Rα2-CAR:

A third-generation CAR construct consisting of a single chain Fv (scFv) antibody sequence against IL-13Rα2 (as ectodomain), a CD28 transmembrane domain along with CD3ζ and CD28 and 4-1BB endodomain sequences was designed, codon-optimized, and synthesized by GenScript® (GenScript, NJ) in pUC57 simple subcloning vector. The novel scFv was previously cloned using the Griffin.1 library, a scFv library made from synthetic v-gene segments, and derived by recloning VH and VL human synthetic Fab Lox library vectors into the phagemid vector pHEN2 as previously described (Kioi et al. (2008) *Mol Cancer Ther.* 7:1579-1587). A novel approach to re-panning the segment to improve binding affinity to huIL-13Rα2Fc chimeric protein was used. The CAR-T construct was codon optimized and flanked by Bam HI and NotI sites and placed into pCDH-MSCV-MCS-EF1-copGFP-T2A-Puro lentiviral vector (System Biosciences, MA). This transfer plasmid was packaged into 293T cells by co-transfecting with three helper plasmids (pCD/NL-BHA1, pCEF-VSV-G and pCMV-Rev) to produce self-inactivating (SIN) lentiviral vector expressing CAR-IL13Rα2-CAR pseudo-lentivector, which was further purified by ultracentrifugation.

Analysis of Antigen Binding Residues and Complementary Determining Regions (CDR) in scFv IL-13Rα2:

Standardized numbering methods were used to define CDRs, frameworks and residues from the light and heavy chains that have an impact on the interaction and/or affinity of the antibody for its target antigen. Amino acid sequences were analyzed using common numbering schemes of antibody variable domains to study the statistical variability in amino acid composition using the Kabat numbering scheme (ncbi.nlm.nih.gov/igblast). An analysis of residue distribution for both the heavy and light chains was performed, as well as an analysis of CDR sequences, including their lengths.

These data were further analyzed and compared with a structure-based numbering scheme for antibody variable regions, which formed the CDRs and corrected the position numbers of the points within CDRL1 and CDRH1 per Chothia numbering scheme, Martin numbering scheme, which was used for correction of the insertion point within the framework region of heavy and light chains, and ImMunoGeneTics® (IMGT®, The International ImMunoGeneTics® information system, Montpellier, France) numbering scheme, which highlights protein sequences of the immunoglobin superfamily including variable domains from antibody light and heavy chains as well as T cell receptor chains (imgt.org; github.com/oxpig/ANARCI, academic.oup.com/bioinformatics/article/32/2/298/1743894; abysis.org/abysis/sequence_input/key_annotation/key_annotation.cgi; imgt.org/3Dstructure-DB/cgi/Collier-de-Perles.cgi; and chemogenomix.com).

Manufacturing of CAR-T Cells:

Human PBMCs were isolated from buffy coats of normal healthy blood donors who donated blood at the Division of Transfusion Medicine, NIH. CAR-T cells were generated from CD4 and CD8 positive T cells isolated from the normal human blood donor buffy coat using a StraightFrom® Buffy Coat kit (Miltenyi Biotec, Waltham, MA). For CD4/CD8 T cell activation, the cells were activated with anti-CD3/CD28 antibody coated magnetic Dynabeads™ (Invitrogen, Carlsbad, CA) at a ratio of 3:1 (T cell to bead) and transduced with lentiviral vector at different multiplicity of infection (m.o.i). T cells were maintained in culture at 0.6-1×$10^6$ cells/mL in T cell culture medium (TCM) supplemented with 50 ng/ml IL-2 and 10 ng/ml each IL-7 and IL-15 (Miltenyi Biotec, Waltham, MA). These PBMC derived CAR-T cells are termed as CAR-T throughout the manuscript.

A parallel set of experiments was used for transduction and expansion to confirm the identity of transgene and signaling domains in human Jurkat T cells (termed CAR-Jurkat).

Indirect Immunofluorescence Assay for Transgene in Transduced CAR-Jurkat and CAR-T Cells:

For detection of scFv-IL-13Rα2 expression on transduced Jurkat or T cells, a novel indirect immunofluorescence assay by plating 75,000 either Jurkat-CAR or CAR-T cells in a poly-L-Lysine coated 4-well chamber slide was used. Briefly, biotinylated recombinant human IL-13Rα2Fc chimera protein (R&D Biosystems, Minneapolis, MN) was produced using the EZ-Link™ micro sulfo-NHS-Biotinylation kit (Thermo Scientific, Waltham, MA). Transduced Jurkat and T cells were then incubated with 500 ng/ml purified biotinylated recombinant human IL-13Rα2Fc chimera protein followed by streptavidin-Alexa 594® (0.5 μg/ml) to develop red fluorescence in scFv-IL-13Rα2 expressing cells. The cells expressing ≥2+ fluorescence intensity were counted at 200× magnification using a Nikon® epifluorescence microscope. Each value is mean±SD of quadruple experiments determined in a blinded manner and expressed as % positive cells.

Flow-Cytometry Analysis:

BD® FACSCanto™ or FACSCalibur™ (BD Bioscience, San Jose, CA) instruments were used to acquire immunofluorescence data which were analyzed with CellQuest™ (BD Bioscience) or FlowJo® v.7 (FlowJo, LLC Ashland, OR) software for final data analysis and graphic representation. Isotype control was immunoglobulin IgG1-PE (IgG1-PE, Cell Signaling Technology, Denver, MA). CD28 cytoplasmic and CD3ζ endodomains were immunostained with anti-CD28.2 mouse mAb PE conjugate or CD3ζ monoclonal antibody PE conjugate (Thermofisher eBioscience, Carlsbad, CA). Permeabilized CAR-Jurkat or CAR-T cells were immunostained with anti-CD28 and CD3ζ antibodies. The data were expressed as normalized to mode values.

Assessment of T Cell Activation Marker Expression in CAR-T Cells:

T cell activation of CAR-T cells was evaluated by intracellular expression of CD44, CD25, CD69 and interferon-γ as T cell activation markers after treating the cells with brefeldin A (BioLegend, San Diego, CA), by indirect immunofluorescence assay (IFA, abCAM, Cambridge, MA). Each value is expressed as mean±SD of four independent readings scored in a blinded fashion for % positive cells expressing ≥2+ immunofluorescence intensity.

Cell Viability and Proliferation Analysis of CAR-T Cells:

Cell viability of CAR-T cell cultures was examined during cell expansion by trypan blue exclusion technique. To further assess the health of CAR-T cells, cellular proliferation was assessed by the CellTiter 96R® AQueous one solution kit (Promega, Madison, WI). Fisher, Waltham, MA, USA). A known number of CAR-T cells (2,500 cells/well) were plated in quadruple wells of a 96-well culture plate and maintained at 37° C. in a $CO_2$ incubator. Twenty microliters of MTS reagent was added in each well on day 3, 5, and 7. The number of proliferating cells in each well was determined by measuring the optical density of reduced MTS tetrazolium by measuring the absorbance at 490 nm. The experiments were performed in quadruplicate and the results were expressed as mean±SD.

Analysis of Cell Migration and Invasion Potential of CAR-T Cells

The cell migration and invasion potential of CAR-T cells was assessed in 24-well ChemoTx® plates with a 5-μm pore diameter (abCam, Cambridge, MA) (chemotaxis assay). In the lower chambers, 600 μL of unconditioned Dulbecco's Modified Eagle Medium with 10, 50 and 1000 ng/ml hU-IL-13Rα2Fc (R&D Systems), U251- or T98G tumor cell culture conditioned Dulbecco's Modified Eagle Medium with 1% fetal calf serum or control media were added. The upper chambers were loaded with 500,000 CAR-T cells/200 μl. After 6 and 20 hours at 37° C., residual cells were scraped off the polycarbonate filter, and the plate was centrifuged for 2 min at 400×g. The filter was removed, and cells in the lower chamber were counted by trypan blue exclusion technique. Percentage migration was calculated as the number of cells in the lower chamber divided by the total number of cells plated per well. Each value is expressed as mean±SD of four independent experiments.

Cytotoxic Activity:

To determine the cell killing activity of CAR-T cells, a robust homogeneous fluorescence-based non-isotopic cytotoxicity assay was performed. U251 and U87MG glioma cell lines, which are positive for IL-13Rα2 expression, were tested. In addition, IL-13Rα2 gene was silenced by SureSilencing™ shRNA plasmid technique using following siRNA sequence GCTACCATTTGGTTTCATCTT (SEQ ID NO: 17) for transfection of U251 and U87 MG cell lines as per manufacturer's protocol (cat #336313 KH00597N, QIAGEN, Germantown, MD). The IL-13Rα2 positive and IL-13Rα2-silenced tumor cells were labeled by intracellular Calcein violet-acetoxymethyl ester (Lichtenfels et al. (1994) *J Immunol Methods* 172:227-239; Neri et al. (2001) *Clin Diagn Lab Immunol* 8:1131-1135). Release of Calcein Violet in the supernatants recovered at the end of 6 hour of co-culture of target:effector cells in the ratio of 1:10, 1:20, 1:30, 1:40 and 1:50 was measured quantitatively in a fluorescent plate reader. The data are shown as mean±SD of four independent experiments performed in quadruplicate involving co-cultures of target and effector CAR-T cells.

IFN-γ Release:

IL13Rα2-CAR-T cells (100,000) were co-cultured in equal part to IL-13Rα2 positive, IL-13Rα2 negative, or IL-13Rα2 KO tumor cells for 20 hours in a 96 well round bottom plate. At the end of the incubation period, the cultures were centrifuged at 3,500×g for 10 minutes and supernatants were harvested for quantitative determination of IFN-γ secretion by ELISA assay (BioLegend).

Statistical Analysis:

The data were compared using unpaired Student's t-test analyses. P values were calculated using GraphPad Prism® software (GraphPad Software, La Jolla, CA). P values of <0.05 were considered a significant difference. Two-way analysis of variance was used to compare labeling conditions (n=4) and the Wilcoxon test was used to obtain two-sided global P values for cell survival or proliferation (n=4).

Example 2

Identification and Characterization of scFv-IL-13Rα2

The gene for scFv of IL-13Rα2 was identified using a scFv phase display library of synthetic v-gene segments and improved versions of VH and VL showing a hypervariable amino-acid structural composition from a human synthetic Fab Lox library. A novel conserved scFv fragment that provides optimum antigen binding based on amino acid residue analysis by four different schemes was selected. The analysis revealed structure-based scFv variable regions, defined loop structures that form the CDRs, and insertion points inside CDRs exhibiting a hypervariable amino acid composition. The clone derived protein showed >4-fold higher binding affinity to recombinant IL-13Rα2Fc protein as compared to the previously cloned scFv ECD-IL-13Rα2 (Kioi et al, *Mol Cancer Ther,* 7(6):1579-87, 2008).

The improved scFv-IL-13Rα2 is sequence-specific for higher binding affinity, and codon-optimized for better expression in human cells. Furthermore, since the improved scFv-IL-13Rα2 was generated from a library made from synthetic V-gene segments, its spectrum of binding to IL-13Rα2 is expected to be more specific as compared to scFvs derived from a single monoclonal antibody (e.g., Balyasnikova, et al, *J Biol Chem.,* 287 (36):30215-30227, 2012).

Figure 3B:
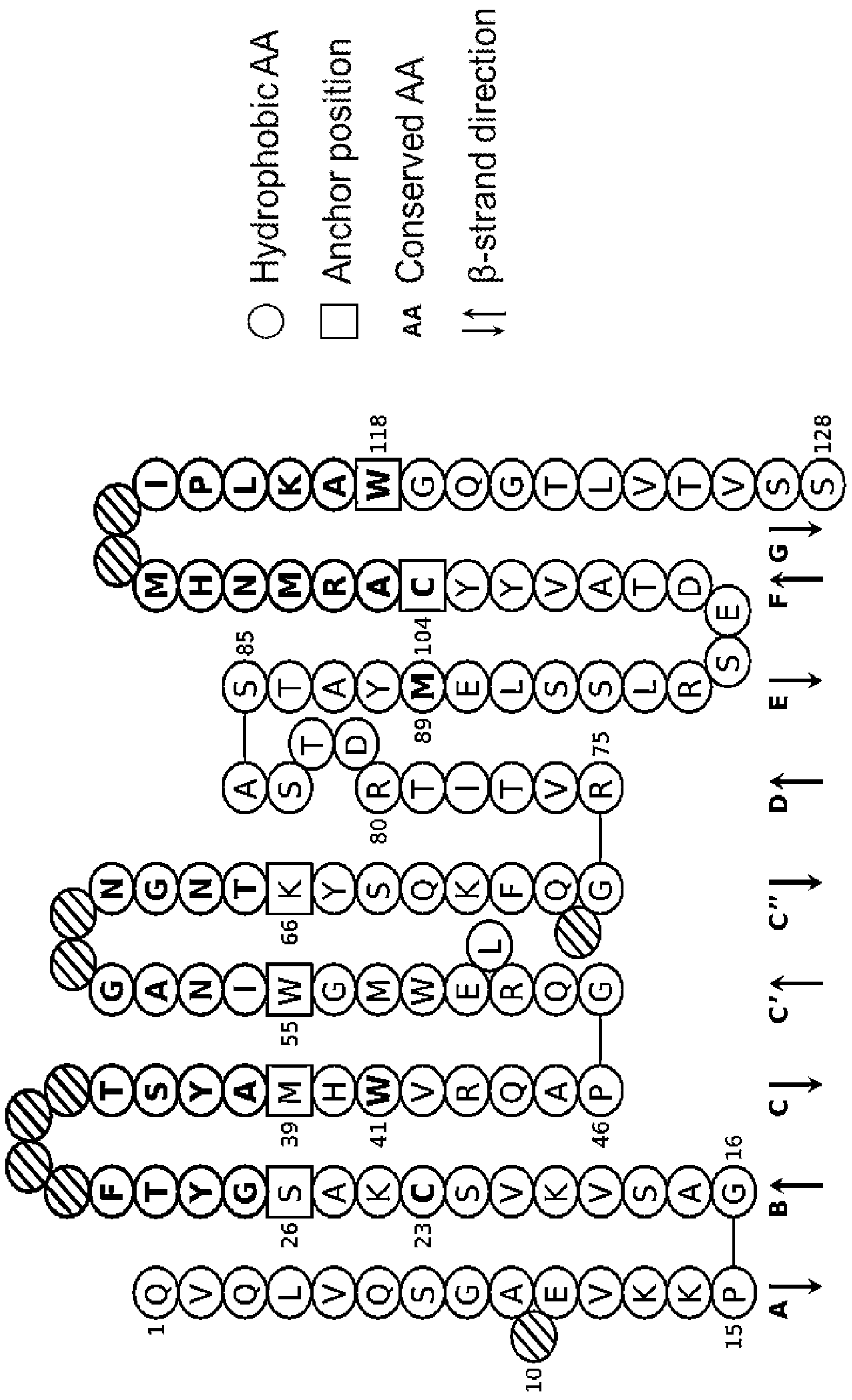

The variable domain of IL-13Rα2 was analyzed by residue numbering schemes to define CDRs, frameworks, and amino acid residues from light and heavy chains, which may have influence on binding affinity and specificity. The analysis revealed 8 different regions with varying numbers of residues and lengths for the heavy chain (FIGS. 2 and 3A). The analyzed sequences exhibited variable lengths of gaps where insertions could only be included at precise positions. The distribution of residues in the heavy chain is shown in FIG. 3A. The data analysis further revealed that the amino acid residues 27-38 in ascending loop B (CDR1), 55-59 in ascending C loop, 62-65 in descending C loop C (CDR2), 105-110 in ascending loop F and 113-117 in descending loop F (CDR3) are structural constituents of heavy chain (FIG. 3B).

Figure 5B:
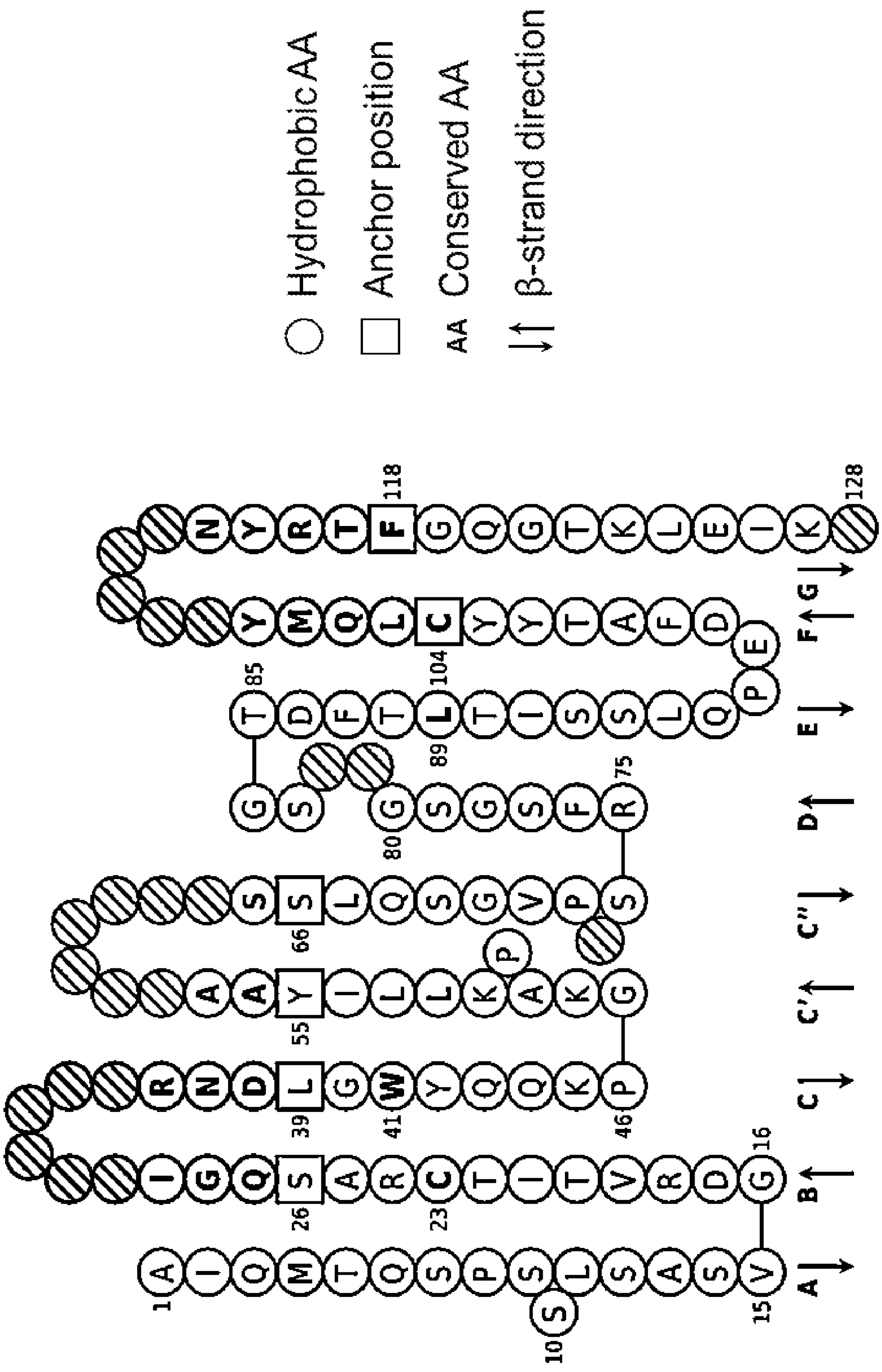
Figure 6:
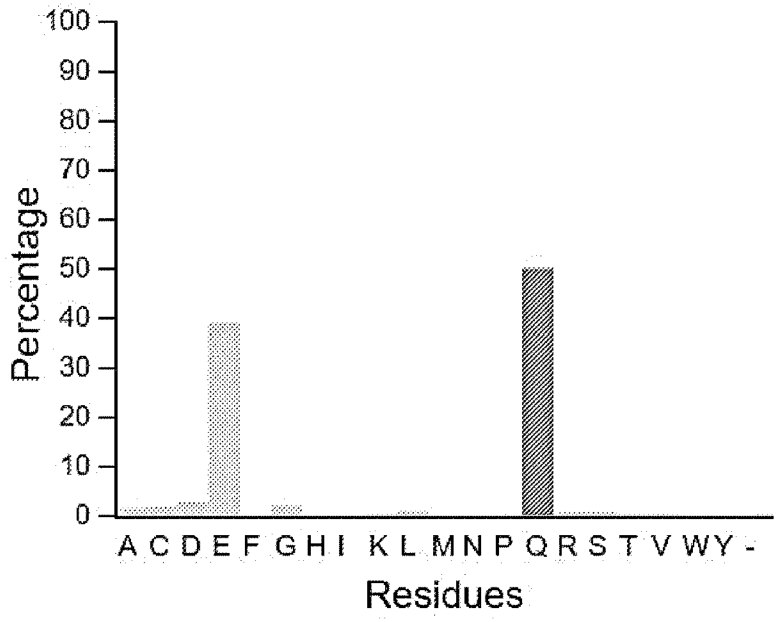
FIG. 6 shows the distribution of heavy chain amino acids of the IL-13Rα2 antibody and their respective frequency.
Figure 7:
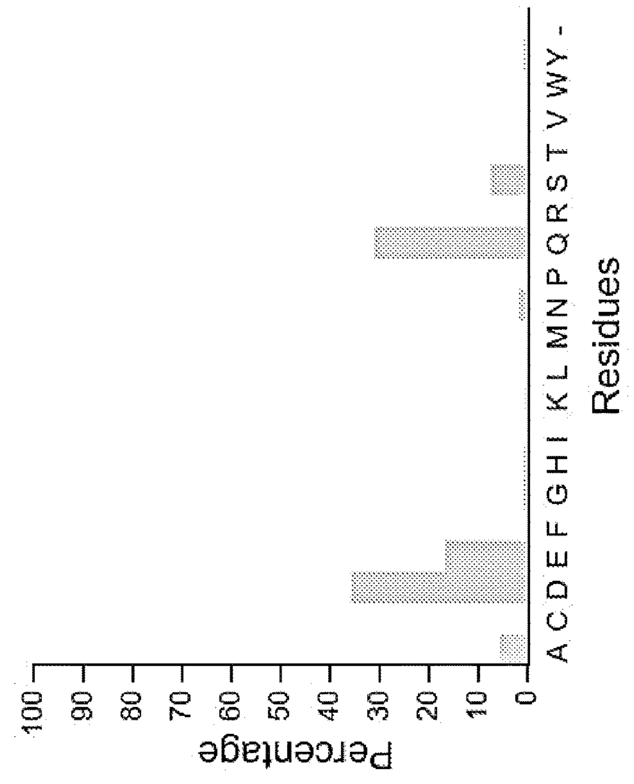
FIG. 7 shows the distribution of light chain amino acids of the IL-13Rα2 antibody and their respective frequency.

Analysis of the light chain showed 9 different regions, including a tail region of 275 amino acids (FIG. 5A). Similar to the heavy chain structural analysis for amino acid residues, light chain amino acids 24-29 in the ascending B loop and 36-39 in descending C loop belong to CDR1-light, 56-57 in the ascending C loop and 65-69 in the descending C loop to CDR2-light, and 105-108 in the ascending F loop and 114-117 descending G loop to CDR3-light, are conserved (FIG. 5B). The distribution of amino acids in heavy chain and light chain after analyzing by Kabat numbering scheme is shown in FIGS. 6 and 7, respectively.

Kabat numbering of scFv residue sequence was also analyzed for a comparative alignment analysis with IMGT, Chothia, and Martin numbering schemes for antibody variable regions, loop structures that form the CDRs, position numbers of the insertion points within CDR-H (heavy) and CDR-L (light) chains, including variable domains from antibody heavy chain (FIG. 8) and light chain (FIG. 9) and amino acid sequence alignment of the germ-line V. These analyses revealed a structural position of amino acids that are involved in antigen binding and displaying hypervariable amino acid composition.

Example 3

Development of the scFv-IL-13Rα2 CAR Construct

Figure 11:
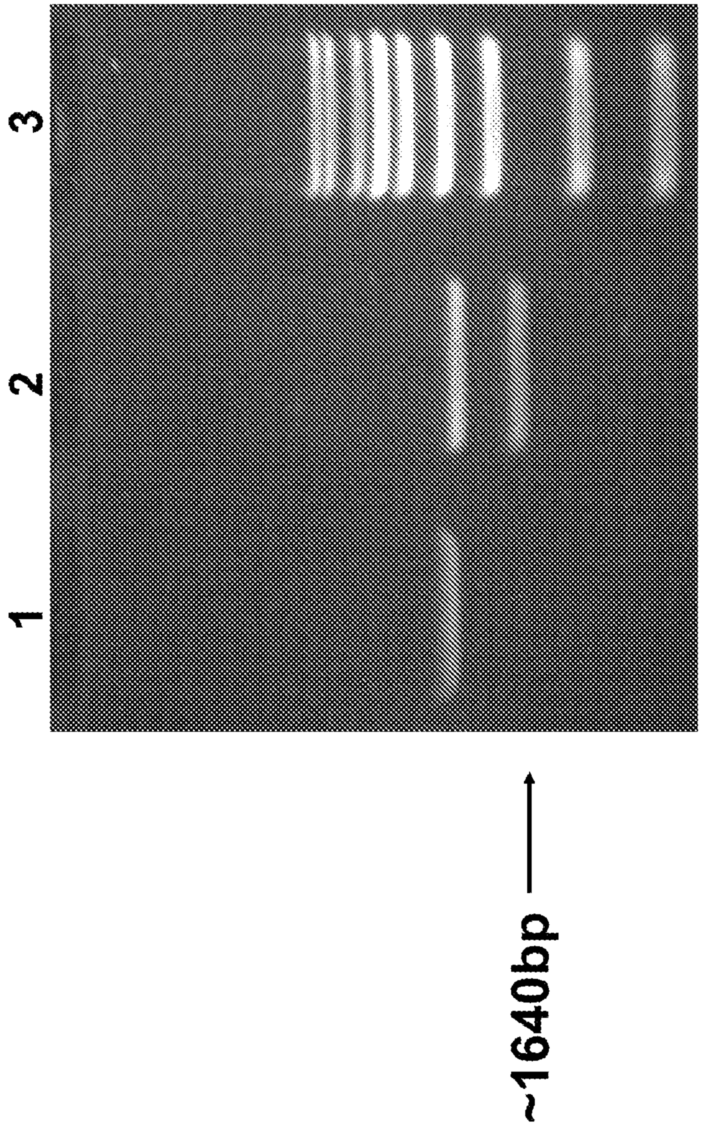
FIG. 11 shows a restriction digest of a vector containing a scFv IL-13Rα2 CAR. Approximately 1.0 μg plasmid DNA was digested with BamH1 and Not1 at 37° C. for 1 hour and electrophoresed in 1% agarose gel then stained. Lane 1 is undigested scFv-IL-13Rα2 CAR construct plasmid, lane 2 is the plasmid DNA digested with BamH1 and Not1, and lane 3 is a KB reference ladder.

The optimized CAR-T construct was placed into pCDH-MSCV-MCS-EF1-copGFP-T2A-Puro lentiviral vector (System Biosciences, MA). Sequencing data confirmed that the CAR construct is 1631 bp long, contains 60.35% GC, and consists of a CD8 signal peptide, the scFv-IL-13Rα2 transgene, a CD8 hinge, a CD28 transmembrane domain, a CD28 cytoplasmic domain, a 4-1BB, and a CD3ζ domain. FIG. 10 shows the corresponding amino acid sequence of the CAR-T construct with a 5' BamH1 restriction site as well as the location and sequence of each feature or domain. Restriction digest of CAR-T plasmid DNA revealed a 1640 bp band insert and a second band of cleaved vector (FIG. 11).

The recombinant lentiviral vector, along with three helper plasmids (pCD/NL-BHA1, pCEF-VSV-G and pCMV-Rev), were packaged to produce the final scFv-CAR-lentivirus in a HEK 293T producer cell line.

Example 4

Generation and Characteristics of IL-13Rα2-CAR-T Cells

The scFv-IL-13Rα2 CAR construct was transduced into Jurkat cells (an immortalized T cell line) to produce IL-13Rα2-CAR-Jurkat cells. Similarly, IL-13Rα2-CAR-T cells were generated from human peripheral blood mononuclear cells (PBMCs) that were activated, transduced with the vector, and expanded in culture.

Figure 12B:
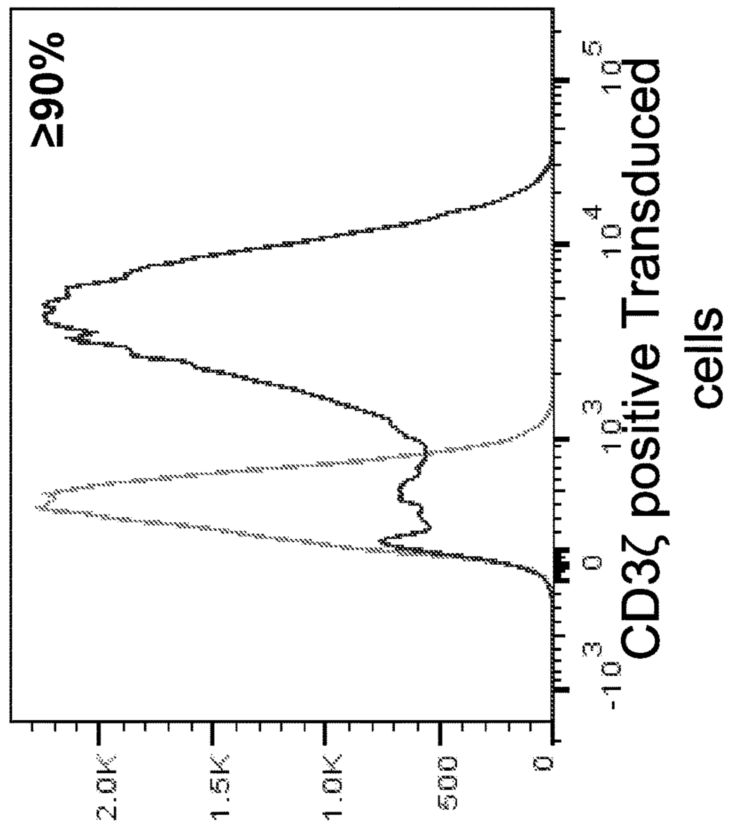
FIGS. 12A-12B show the expression of CD28 (cytoplasmic) (FIG. 12A) and CD3ζ (FIG. 12B) signaling domains in transduced CAR-Jurkat cells. FACS analysis of the CAR-Jurkat cells was performed after permeabilizing transduced Jurkat cells and immunostaining with anti-CD28 (CD28.2) mouse mAb PE conjugate (Cat #27826, Cell Signaling Technology, Danvers, MA) and CD3ζ monoclonal antibody PE conjugate (Cat #12-2479-82, ThermoFisher eBioscience, Carlsbad, CA). The data are expressed as normalized to mode values.
Figure 12A:
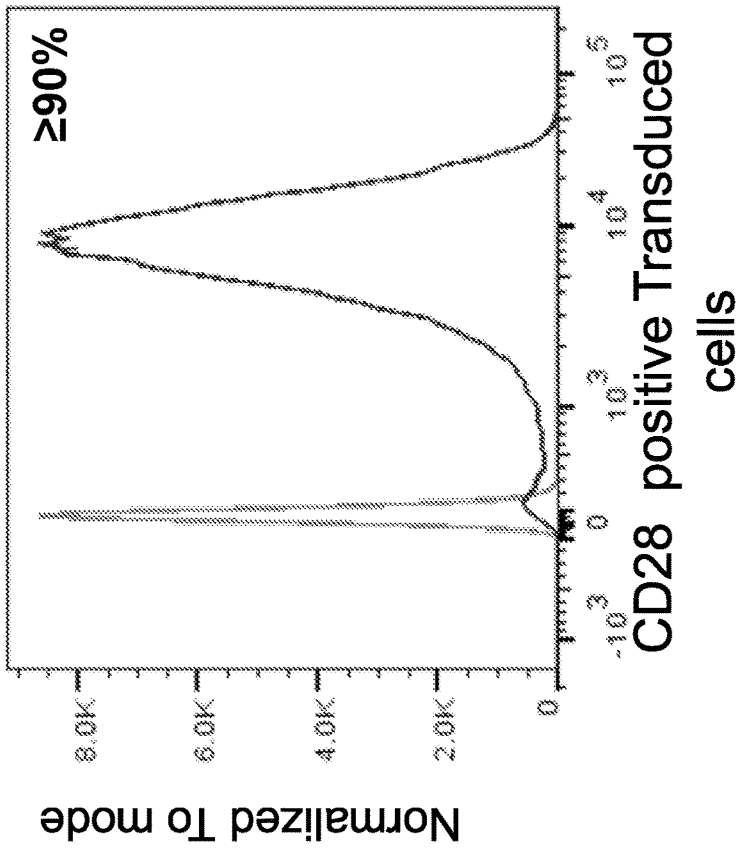

Fluorescence-activated cell sorting (FACS) analysis confirmed expression of CD28 and CD3ζ in transduced CAR-Jurkat cells (FIGS. 12A and 12B). FACS analysis was performed after permeabilizing transduced Jurkat cells and immunostaining with anti-CD28 (CD28.2) mouse mAb PE conjugate (Cat #27826, Cell Signaling Technology, Danvers, MA) and CD3ζ monoclonal antibody PE conjugate (Cat #12-2479-82, ThermoFisher eBioscience, Carlsbad, CA). The data were expressed as normalized to mode values. Both CD28 cytoplasmic and CD3ζ signaling domains were detected.

Figure 13A:
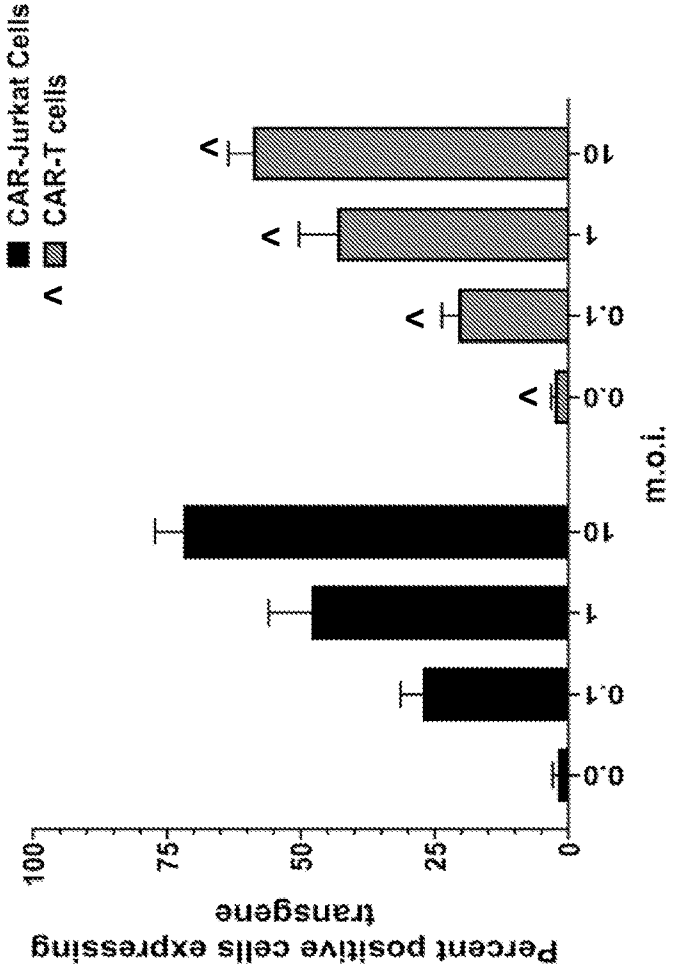
FIGS. 13A-13B show the identification of the scFv IL-13Rα2 CAR transgene in transduced Jurkat cells and T cells by indirect immunofluorescence assay (IFA) analysis. Transduced Jurkat cells and T cells were incubated with 500 ng/ml biotinylated recombinant human IL-13Rα2Fc chimeric protein followed by streptavidin-Alexa 594 to develop fluorescence in scFv-IL-13Rα2 expressing cells. The cells expressing ≥2+ fluorescence intensity were counted at 200× magnification by viewing in NIKON epifluorescence microscope. Each value is mean±SD of quadruple experiments determined in a blinded manner and expressed as % positive cells (FIG. 13A).
Figure 13B:
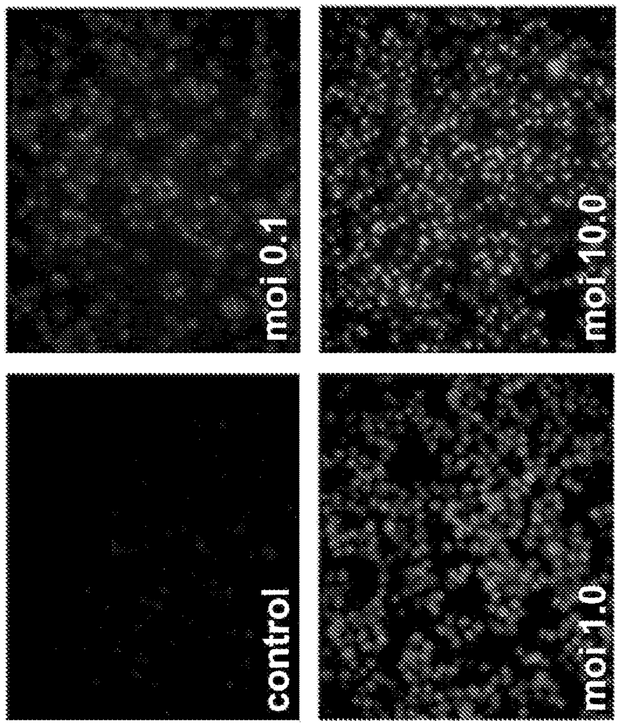

Expression of the scFv-IL-13Rα2-CAR transgene was confirmed by an indirect immunofluorescence assay (IFA) (FIGS. 13A and 13B). The IFA assay was performed on transduced Jurkat and T cells. Cells expressing ≥2+ fluorescence intensity were counted at 200× magnification by viewing in Nikon® epifluorescence microscope. The percent of positive cells with >2+ immunostaining intensity was slightly higher in Jurkat cells than in CAR-T cells. A representative IFA image of transduced Jurkat cells is shown in FIG. 13B. Each value is mean±SD of quadruple experiments determined in a blinded manner and expressed as % positive cells.

Figure 14:
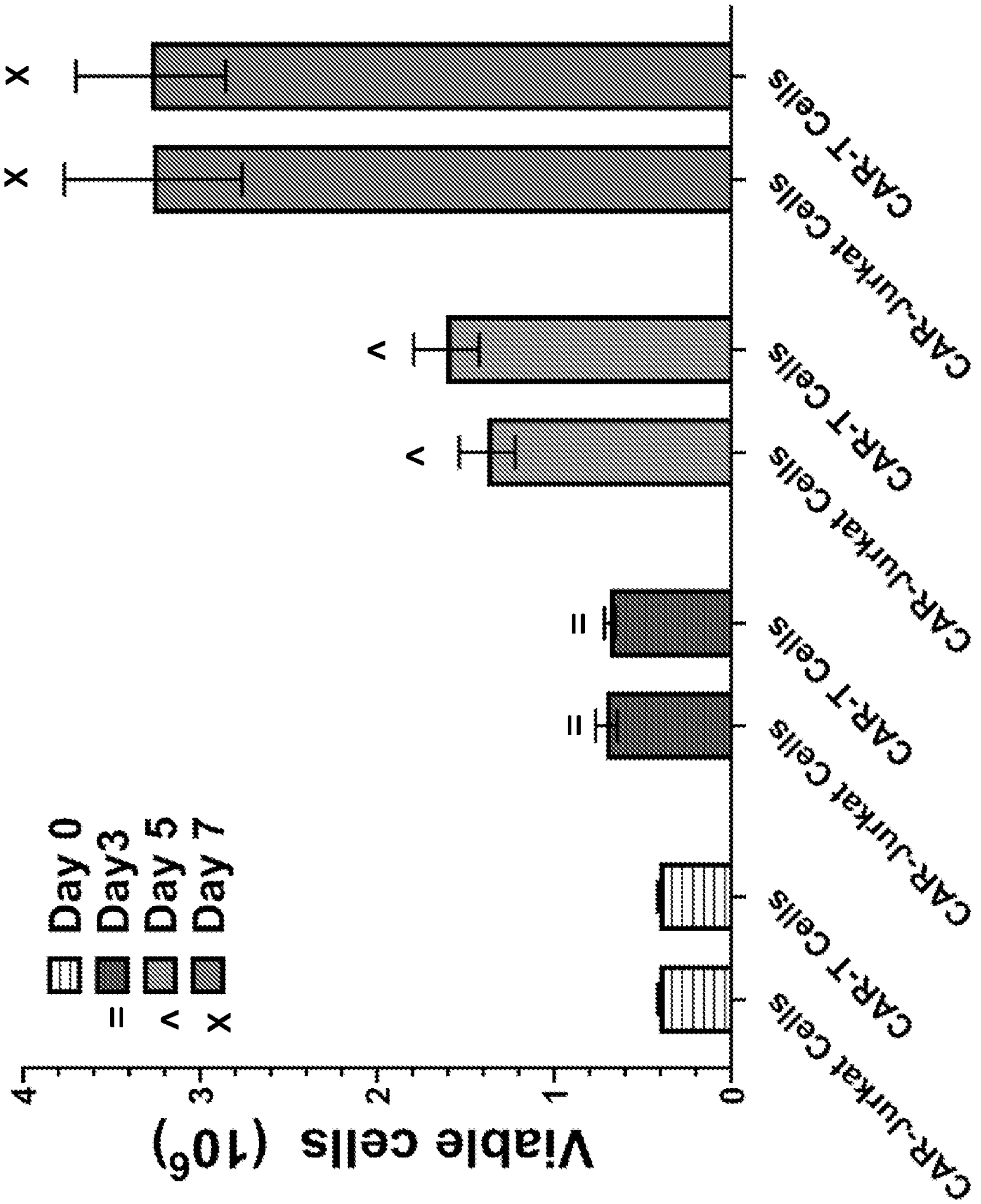
FIG. 14 shows cell viability of scFv IL-13Rα2 CAR-Jurkat and scFv IL-13Rα2 CAR-T cells in cell culture over the course of seven days. Viability was determined by trypan blue exclusion and is expressed as number of viable cells.
Figure 15:
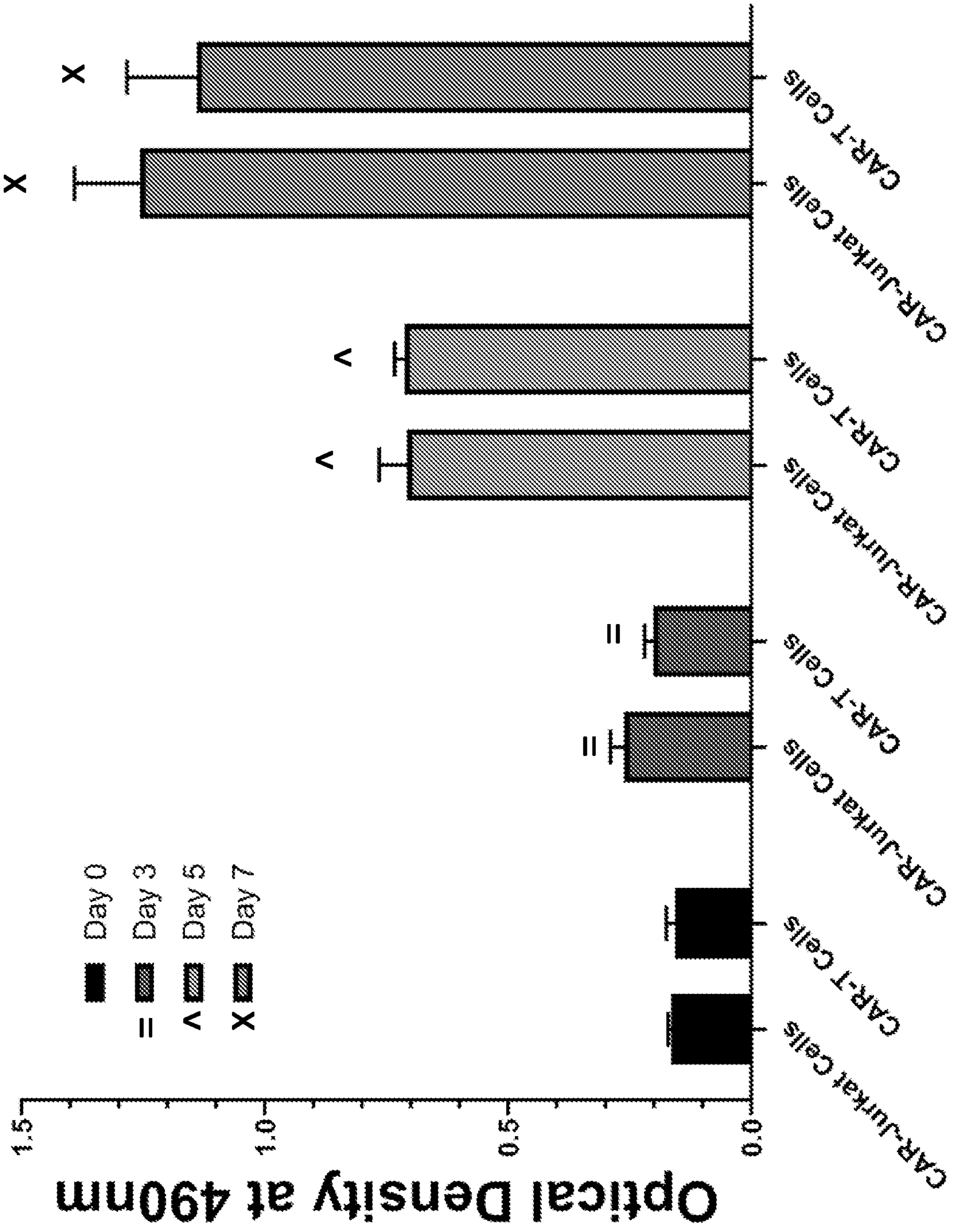
FIG. 15 shows cell proliferation of scFv IL-13Rα2 CAR-T cells in vitro by MTS assay. Transduced Jurkat cells and T cells were monitored for cell proliferation up to 7 days in appropriate culture medium. The proliferative activity of transduced cells was assessed by measuring the optical density of reduced MTS tetrazolium by proliferating cells at 490 nm at specified time points. Each value is a mean±SD of four independent experiments

The viability of IL-13Rα2-CAR-Jurkat and CAR-T cells in cell culture was evaluated over the course of seven days by trypan blue exclusion technique. As shown in FIG. 14, both CAR-Jurkat and CAR-T cells continued to grow for 7 days and maintained cell viability. Similarly, both CAR-Jurkat and CAR-T maintained metabolic and proliferative activity for 7 days as determined by MTS assay (FIG. 15).

Figure 16:
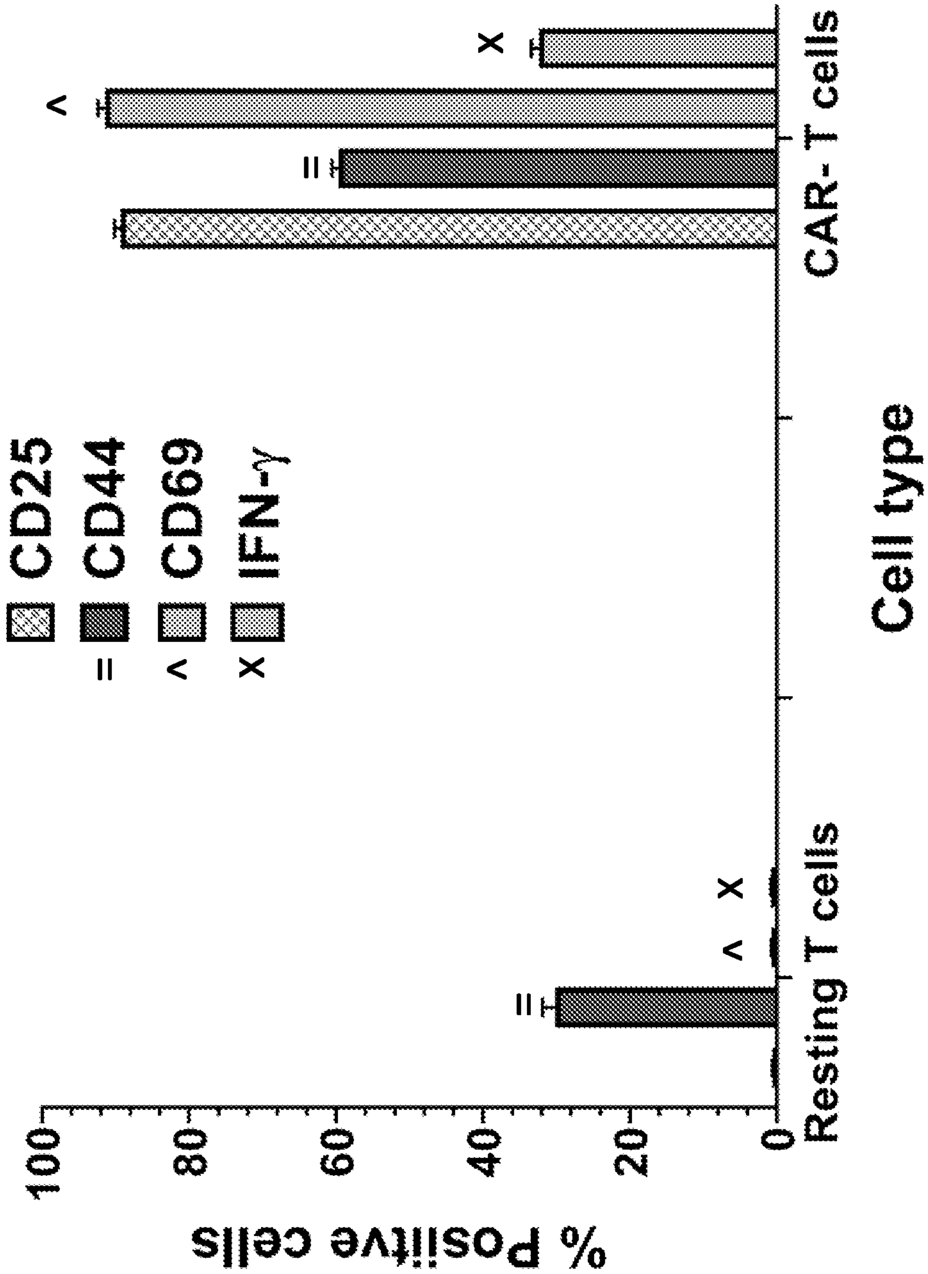
FIG. 16 shows expression of T cell activation markers in CAR-T cells. Expression of T cell activation markers (CD25, CD44, CD69) and intracellular IFN-γ expression was measured on day 7.

The cell phenotype and function of CAR-T cells was assessed by FACS analysis of cell surface and intracellular markers and compared with resting T cells. The CAR-T cells expressed CD25, CD44 and CD69 cell surface markers indicative of T cell activation and expression of all three markers was preserved during the expansion phase of CAR-T cell cultures as measured on day 7 (FIG. 16). Similarly, CAR-T cells expressed intracellular interferon-γ while resting T cells did not show any expression of IFN-γ (FIG. 16).

Example 5

CAR-T Cells are Cytotoxic to IL-13Rα2+ Glioma Tumor Cells In Vitro

Figure 17:
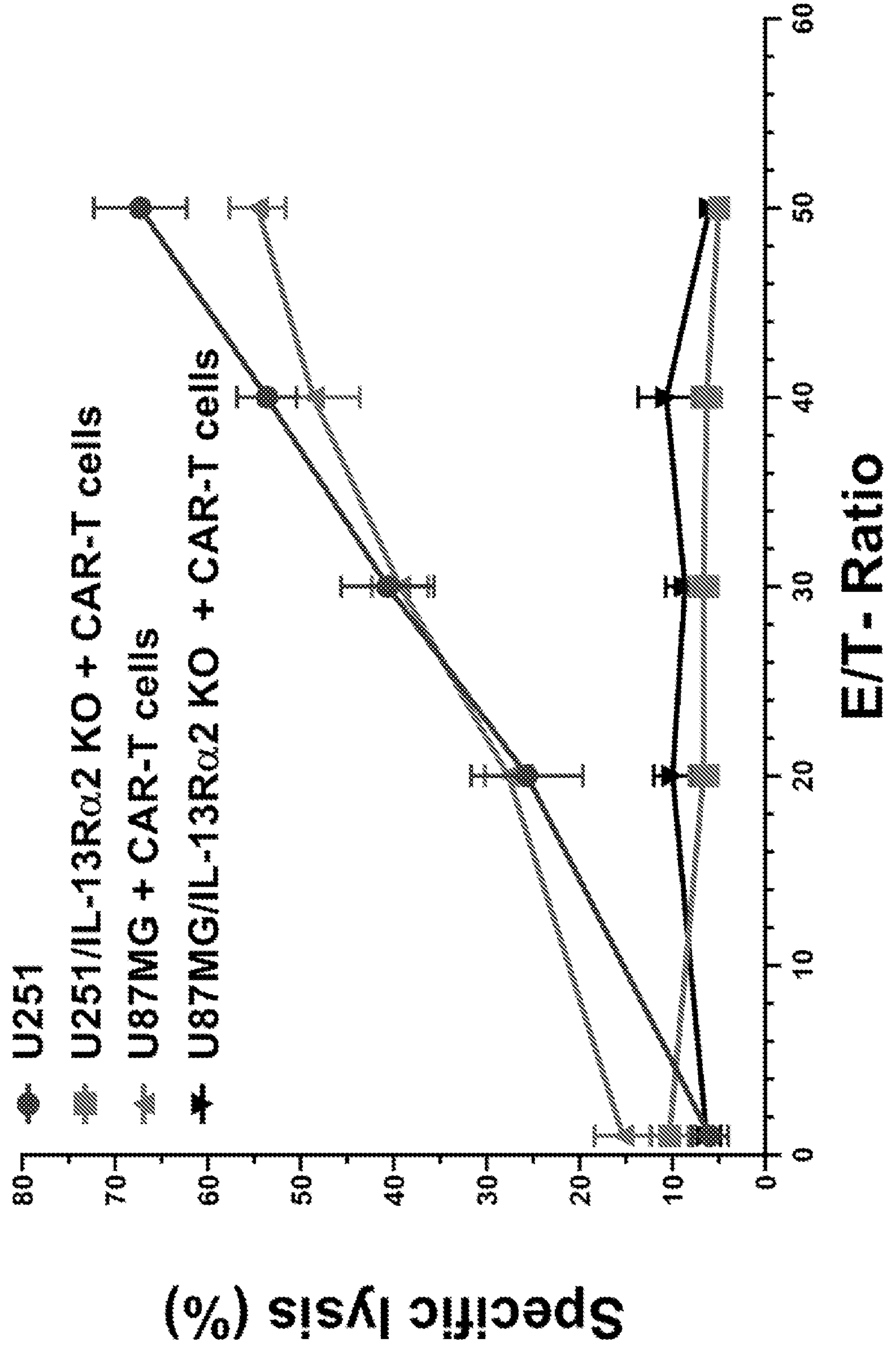
FIG. 17 shows scFv IL-13Rα2 CAR-T cell specificity and cytotoxicity to IL-13Rα2+ glioma tumor cells in co-culture. After 6 hour co-culture with a fixed number of calcein-violet loaded tumor cells (5000) as target cells at various effector to target (E:T) ratios, release of fluorescent dye was measured to determine cell lytic activity of the CAR-T cells. IL-13Rα2 knock-out (KO) tumor cells were used as negative controls. Each value is a mean±SD of three independent experiments performed in quadruplicate.
Figure 18:
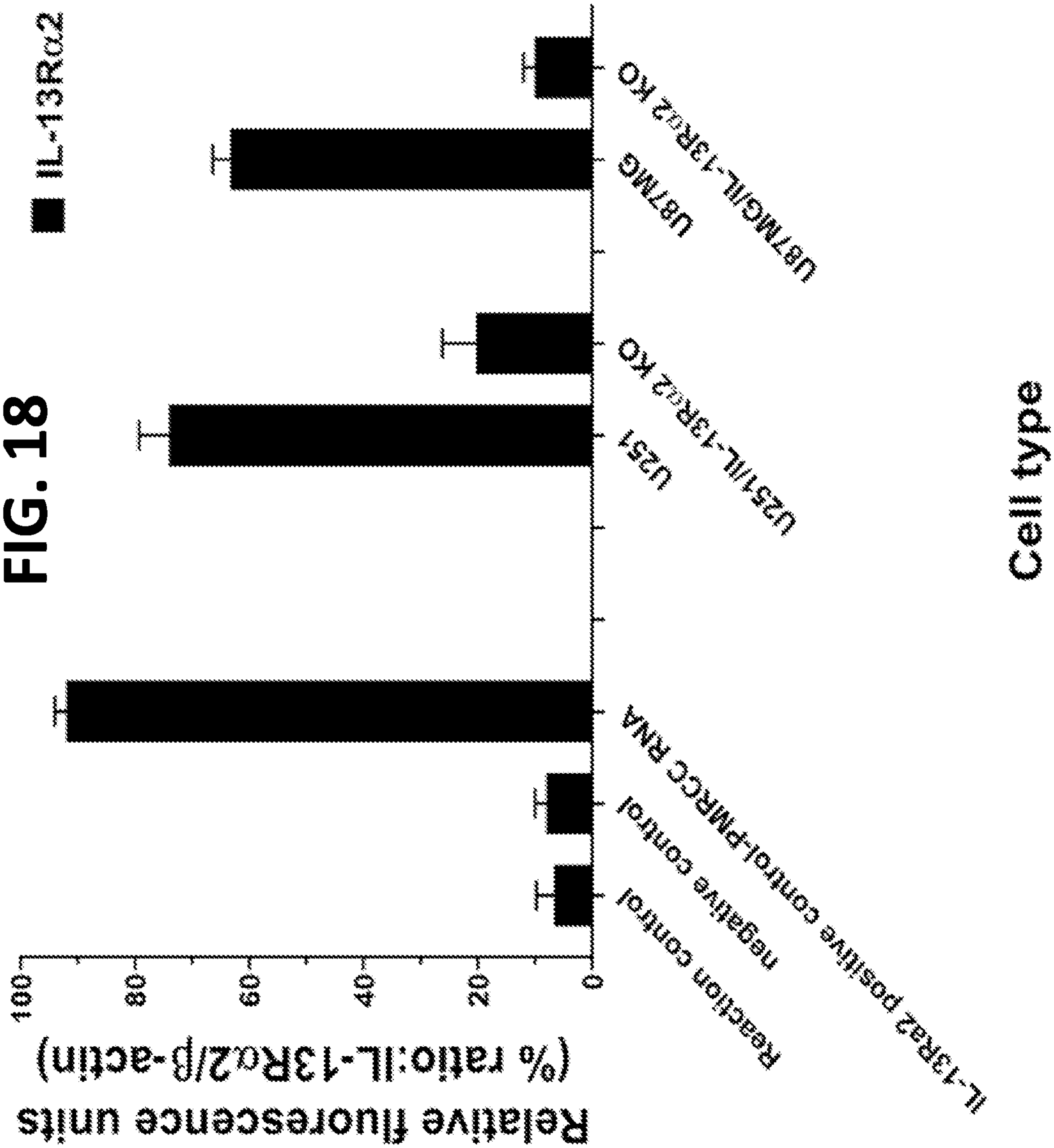
FIG. 18 shows siRNA silencing of IL-13Rα2 in U251 and U87MG glioma cell lines. Relative fluorescence units of IL-13Rα2/β-actin were measured by RT-qPCR assay. Each value denotes mean±SD of quadruple runs performed independently in triplicate.

Potency of the IL-13Rα2-CAR-T cells was investigated by measuring their cytotoxicity against two IL-13Rα2 positive malignant glioma tumor cell lines known to express high levels of IL-13Rα2 (U251 and U87MG). The IL-13Rα2-CAR-T cells were found to specifically kill IL-13Rα2 expressing tumor cells (IL-13Rα2+) in an effector cell number dependent manner (FIG. 17). The killing of tumor cells was highly specific to IL-13Rα2 expression on target tumor cells as gene silencing of IL-13Rα2 on target tumor cells nearly eliminated all cytotoxic activity of CAR-T cells.

Figure 19:
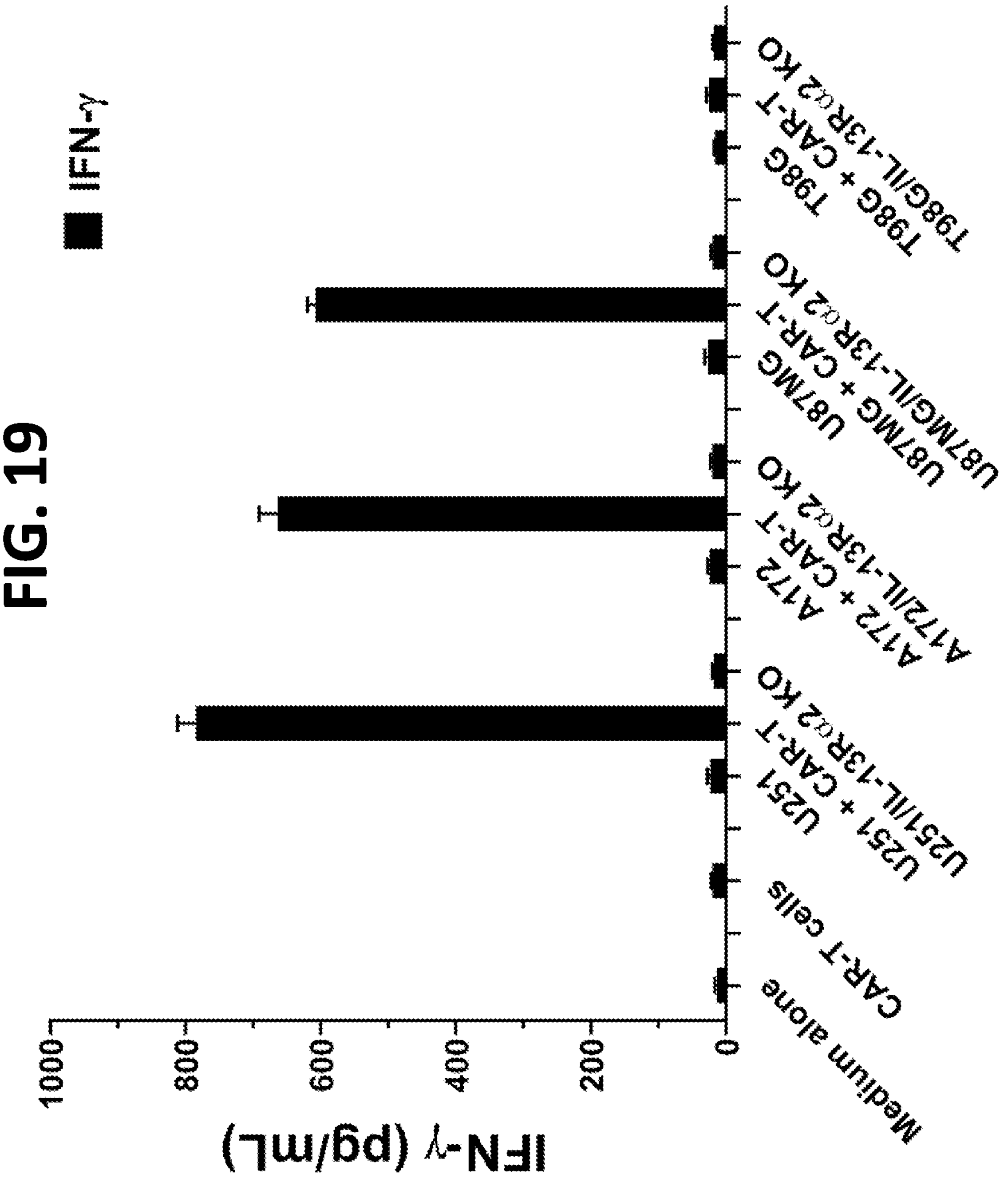
FIG. 19 shows IFN-γ release by scFv IL-13Rα2 CAR-T cells when co-cultured with tumor cells. When the scFv IL-13Rα2 CAR-T were exposed to IL-13Rα2 positive tumors, the CAR-T cells made a large quantity of IFN-γ. However, when exposed to IL-13Rα2 negative T98G or IL-13Rα2 KO tumor cells, they secreted only a basal amount of IFN-γ. Representative data of 3 independent experiments performed in quadruplicate is shown.

IL-13Rα2-CAR-T cell potency and specificity was also evaluated based on the release of IFN-γ upon exposure to IL-13Rα2 expressing tumor cells. As shown in FIG. 19, the CAR-T cells produced large and approximately equal amount of IFN-γ in the supernatant when co-cultured with three IL-13Rα2 positive glioma cell lines (U251, A172, and U87MG). In contrast, the CAR-T cells only secreted a basal amount of IFN-γ when co-cultured with IL-13Rα2 negative or IL-13Rα2 KO tumor cell line, indicating a specific response to IL-13Rα2 positive tumor cells.

Figure 20:
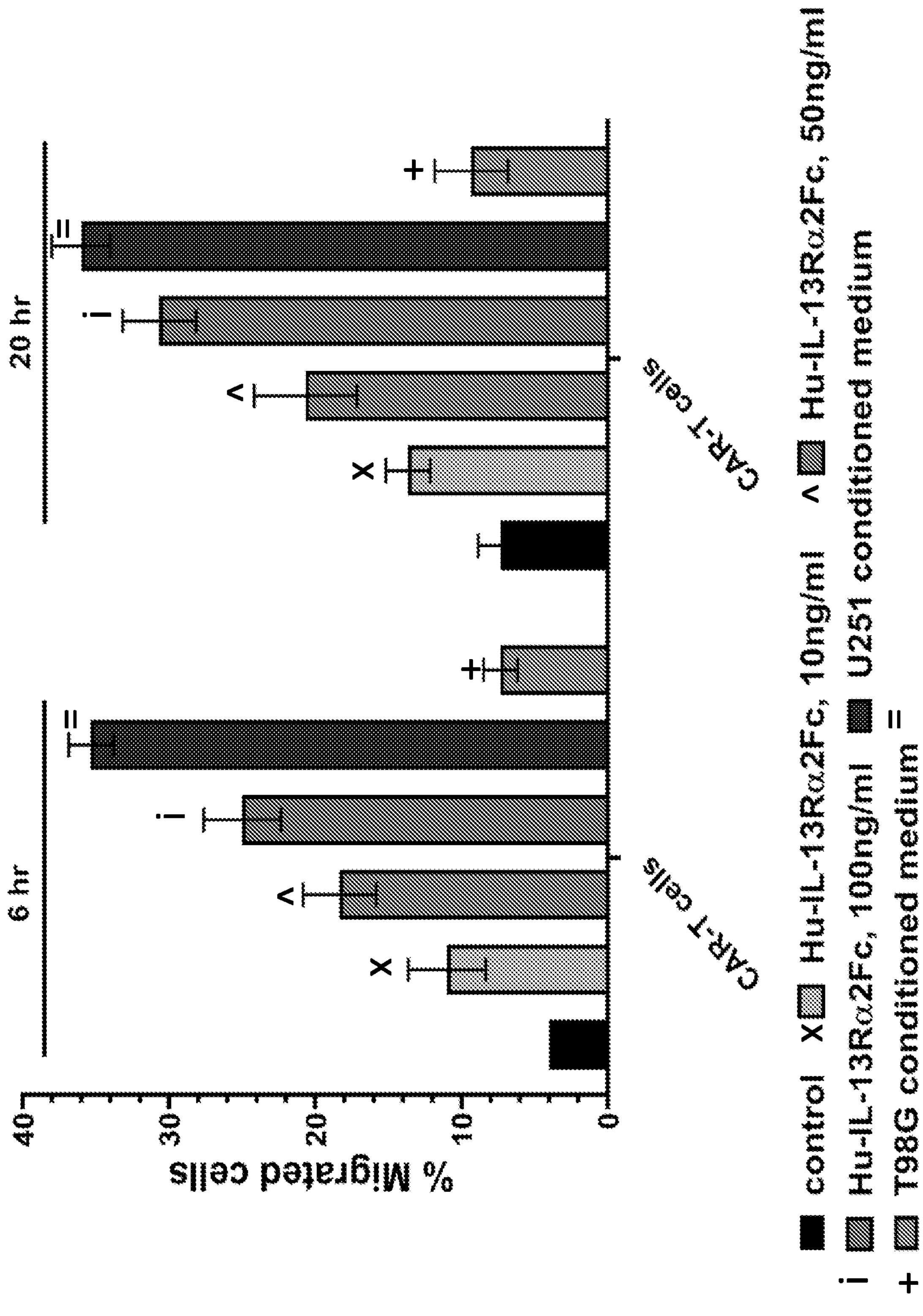
FIG. 20 shows a Boyden chamber assay. The in vitro migration assay demonstrates that scFv-IL-13Rα2 CAR-T cells can migrate from the upper chamber to the lower chamber in a concentration dependent manner in medium containing different concentrations of HuIL-13Rα2Fc or conditioned medium from IL-13Rα2 positive U251 tumor cell culture. No migration was observed in the control or conditioned medium from IL-13Rα2 negative T98G tumor cell cultures. Each value is a mean±SD of four independent experiments performed in triplicate.

Finally, IL-13Rα2-CAR-T cell migration and invasion was investigated using a Boyden chamber assay. CAR-T cells were exposed to three different concentrations of recombinant IL-13Rα2Fc chimeric protein or conditioned medium obtained from IL-13Rα2 positive and IL-13Rα2 negative gene silenced human glioma cell lines. As shown in FIG. 20, CAR-T cell cultures from day 8 of expansion phase invaded and migrated to human IL-13Rα2Fc in a concentration dependent manner at 6 and 20 hr time points. Similarly, CAR-T cells invaded and migrated to conditioned medium from IL-13Rα2 positive glioma cells, but not to conditioned medium from IL-13Rα2 negative glioma cells.

Example 6

Testing In Vivo Efficacy of IL-13Rα2-CAR-T Cells

This example describes methods that can be used to test efficacy of IL-13Rα2-CAR cells in vivo. While particular methods are provided, one of skill in the art will recognize that methods that deviate from these specific methods can also be used, including addition or omission of one or more steps.

A mouse solid cancer model can be used to evaluate efficacy of IL-13Rα2-CAR-T cells. In this model, immunodeficient mice are subcutaneously or orthotopically implanted with human tumor cells derived from brain cancer, pancreatic cancer, prostate cancer, or other tumors.

In one example, athymic nude mice are implanted with human brain tumor cells (U251 and U87MG glioma). In another example, NOD/Shi-scid/IL-2R$\gamma^{null}$ (NOG) mice are implanted with tumor cells. NOG mice lack mature T cells, B cells, and mononuclear cells due to NOD (nonobese diabetic) background and SCID mutation. In addition to the immunodeficiency, interleukin-2 receptor gamma deficiency in NOG mice allows engrafted human-T cells to subsequently differentiate.

In one example, humanized PBMC reconstituted NOG mice are used. NOG mice reconstituted with human PBMC develop mature human immune cells in peripheral blood and the spleen (Brady et al. (2014) *Clin Transl Immunology* 19: 3(12). These mice are implanted subcutaneously or orthotopically with tumor cells, such as U251 and U87 glioma tumor cells, or HS766, MiaPaca2, BXPC-3, Panc-1, HPAF-II or ASPC-1 pancreatic tumor cells. Mice are then administered IL-13-Rα2-CAR-T cells. A dose titration study is used to determine optimal cell dose for each tumor model. An additional group of NOG mice may be included that are injected with IL-13Rα2 gene knock out (KO) tumor cells to delineate the role of IL-13Rα2 as a tumor target.

The animals are followed for the regression of established tumors, metastasis and survival of control alongside CAR-T cell treated animals. Immune response of the animals is evaluated by measuring a number of parameters, such as $CD4^+$ and $CD8^+$ cells, regulatory cells (T regulatory cells (Tregs), myeloid derived suppressor cells (MDSC), antibody levels, and serum cytokine levels. The overall health of each animal is assessed at various time points by measuring body weight and through histological studies of vital organs at the time of sacrifice.

The efficacy of the IL-13Rα2-CAR-T cell therapy is also evaluated in combination with various tumor pre-treatments. The methods are similar, except tumor-bearing animals are pre-treated with a HDAC inhibitor (e.g., Trichostatin A (TSA), sodium butyrate (NaB), SP600125, SR11302, or Suberoylanilide Hydroxamic Acid (SAHA)), adrenomedullin (AM), or IL-13-PE prior to CAR-T cell administration and compared to suitable control treatments (e.g., animals not receiving CAR-T therapy, not receiving the combination therapy, and/or animals with IL-13Rα2 knocked-down tumor cells).

Example 7

Testing In Vivo Efficacy of IL-13Rα2-CAR-T Cell in Combination with HDAC Inhibitor Treatment This example describes methods that can be used to test efficacy of IL-13Rα2-CAR cells in combination with HDAC inhibitors in vivo. While particular methods are provided, one of skill in the art will recognize that methods that deviate from these specific methods can also be used, including addition or omission of one or more steps.

The effectiveness of IL-13Rα2-CAR-T cell therapy in combination with HDAC inhibitor can be evaluated in a cancer model using subcutaneous and orthotopic tumor implantation in immunodeficient mice. In this example, a pancreatic cancer cell line (such as Panc-1 or ASPC-1) is used to develop subcutaneous tumor implants in the flank of female athymic nude or NOG mice. About 4-6 days after tumor implantation, TSA or SAHA is administered. About 5 days after the start of TSA or SAHA administration, IL13Rα2-CAR-T cells or a control is also administered.

Mice body weight and tumor size is monitored and periodically measured. $CD4^+$, $CD8^+$, and T reg cell numbers, and cytokine profile in the blood are also periodically measured. Measurements continue until tumor size reaches 20 $mm^2$ in diameter. Animals are monitored during the course of the entire experiment for adverse toxic effects. An additional group of animals implanted with IL-13Rα2 knocked-down tumor cells and treated with the IL-13Rα2-CAR-T cell therapy may also be included as a control.

Example 8

Testing In Vivo Efficacy of IL-13Rα2-CAR-T Cell Therapy in Combination with Adrenomedullin This example describes methods that can be used to test efficacy of IL-13Rα2-CAR cells in combination with adrenomedullin treatment in vivo. While particular methods are provided, one of skill in the art will recognize that methods that deviate from these specific methods can also be used, including addition or omission of one or more steps.

In one example, PC-3 prostate cancer cells transfected with AM, or mock-transfected, or a non-transfected control are injected subcutaneously in immunodeficient mice, such as male athymic nude mice. When the tumor size reaches approximately 20 $mm^2$ (in approximately one week), mice are administered CAR-T cells and subsequently monitored for response to treatment.

In another example, mice are injected with PC-3 tumor cells, and when the tumor size reaches approximately 20 $mm^2$, AM peptide (or control) is periodically injected intratumorally. About forty-eight hours after the last AM treatment, the sensitivity of PC-3 tumors to CAR-T cells is examined. Animals injected with PC-3 cells may be included as additional controls.

The mice will be followed over several weeks to assess effectiveness of CAR-T therapy, for example, tumor shrinkage, general health of the animals, CD4+, CD8+, T regs, and blood cytokine levels.

Example 9

Testing In Vivo Efficacy of IL-13Rα2-CAR-T Cell Therapy in Combination with IL-13-PE This example describes methods that can be used to test efficacy of IL-13Rα2-CAR cells I combination with IL-13PE treatment in vivo. While particular methods are provided, one of skill in the art will recognize that methods that deviate from these specific methods can also be used, including addition or omission of one or more steps.

In this example, mice are treated with TGFβRI and PTEN in the oral epithelium and develop spontaneous squamous cell carcinoma of the head and neck. The mice are then treated with IL-13-PE. About one week later, the mice are treated with IL-13Rα2-CAR-T cells.

The mice are examined for antitumor activity and immunological changes in response to treatment. Some animals are sacrificed about three days after the last dose of CAR-T cell therapy to perform FACS analysis on splenocytes. MDSCs are analyzed by FACS analysis using the monocyte/macrophage markers CD11b+ and the granulocyte antigen Gr-1+.

In view of the many possible embodiments to which the principles of the disclosure may be applied, it should be recognized that illustrated embodiments are only examples and should not be taken as limiting the scope of the invention. Rather, the scope of the invention is defined by the following claims. We therefore claim as our invention all that comes within the scope and spirit of these claims.

We claim:

1. A single-chain fragment variable (scFv) that specifically binds interleukin-13 receptor α2 (IL-13Rα2), wherein the scFv comprises an amino acid sequence comprising variable heavy chain (VH) domain complementarity determining region 1 (CDR1), CDR2, and CDR3 amino acid sequences of amino acid positions 31-35, 50-66, and 99-107 of SEQ ID NO: 1, respectively, and variable light chain (VL)

domain complementarity determining region 1 (CDR1), CDR2, and CDR3 amino acid sequences of amino acid positions 157-167, 183-189, and 222-229 of SEQ ID NO: 1, respectively.

2. The scFv of claim 1, wherein the amino acid sequence comprises SEQ ID NO: 1 or has at least 90% identity to SEQ ID NO: 1.

3. A nucleic acid molecule encoding the scFv of claim 1.

4. The nucleic acid molecule of claim 3, comprising a nucleic acid sequence having at least 90% identity to SEQ ID NO: 2 or comprising SEQ ID NO: 2.

5. A vector comprising the nucleic acid molecule of claim 3.

6. A chimeric antigen receptor comprising:

(a) an antigen binding domain comprising the scFv of claim 1;

(b) a hinge domain;

(c) a transmembrane domain; and (d) an intracellular domain comprising one or more signaling domains.

7. The chimeric antigen receptor of claim 6, further comprising a signal peptide.

8. The chimeric antigen receptor of claim 6, wherein:

(a) the one or more signaling domains comprise a CD28 domain, a 4-1BB domain, a CD3ζ domain, or any combination of two or more thereof;

(b) the hinge domain comprises a CD8a hinge domain; and/or (c) the transmembrane domain is a CD28 transmembrane domain.

9. The chimeric antigen receptor of claim 6, comprising: an amino acid sequence having at least 90% identity to SEQ ID NO: 3 or amino acids 22-538 of SEQ ID NO: 3; or SEQ ID NO: 3 or amino acids 22-538 of SEQ ID NO: 3.

10. A nucleic acid molecule encoding the chimeric antigen receptor of claim 6.

11. The nucleic acid molecule of claim 10, comprising a nucleic acid sequence having at least 90% identity to SEQ ID NO: 4 or comprising SEQ ID NO: 4.

12. A vector comprising the nucleic acid molecule of claim 10.

13. An immune cell expressing the chimeric antigen receptor of claim 6.

14. The immune cell of claim 13, wherein the immune cell is a T cell, an NK cell, an NKT cell, or a macrophage.

15. A method of producing IL-13Rα2-CAR cells, comprising transforming or transfecting a population of immune cells with the vector of claim 12.

16. A method of treating a subject with cancer, comprising administering an effective amount of the immune cell of claim 13 to the subject.

17. The method of claim 16, wherein the immune cell is autologous or allogeneic to the subject with cancer.

18. The method of claim 16, wherein the subject has a cancer that expresses IL-13Rα2.

19. The method of claim 16, wherein the subject has pancreatic cancer, glioblastoma, head and neck squamous cell carcinoma, ovarian cancer, renal cell carcinoma, uterine cancer, prostate cancer, breast cancer, melanoma, non-small cell lung cancer (NSCLC), Kaposi sarcoma, or adrenal carcinoma.

20. The method of claim 16, further comprising:

(a) treating the subject with one or more of surgery, radiation, chemotherapy, or an additional immunotherapy; and/or (b) administering to the subject a histone deacetylase (HDAC) inhibitor, a cell cycle or checkpoint inhibitor, adrenomedullin, an IL-13-PE immunotoxin, or any combination of two or more thereof.

* * * * *